(12) United States Patent
Tearney et al.

(10) Patent No.: US 8,174,702 B2
(45) Date of Patent: *May 8, 2012

(54) SPECKLE REDUCTION IN OPTICAL COHERENCE TOMOGRAPHY BY PATH LENGTH ENCODED ANGULAR COMPOUNDING

(75) Inventors: Guillermo J. Tearney, Cambridge, MA (US); Nicusor Iftimia, North Chelmsford, MA (US); Brett E. Bouma, Quincy, MA (US)

(73) Assignee: The General Hospital Corporation, Boston, MA (US)

( * ) Notice: Subject to any disclaimer, the term of this patent is extended or adjusted under 35 U.S.C. 154(b) by 158 days.

This patent is subject to a terminal disclaimer.

(21) Appl. No.: 12/510,047

(22) Filed: Jul. 27, 2009

(65) Prior Publication Data

US 2010/0157309 A1    Jun. 24, 2010

Related U.S. Application Data

(63) Continuation of application No. 10/551,735, filed on Sep. 29, 2005, now Pat. No. 7,567,349.

(51) Int. Cl.
*G01B 9/02* (2006.01)
*G01B 11/02* (2006.01)

(52) U.S. Cl. ........................ 356/479; 356/497

(58) Field of Classification Search .................. 356/479, 356/497

See application file for complete search history.

(56) References Cited

U.S. PATENT DOCUMENTS

| | | | |
|---|---|---|---|
| 2,339,754 | A | 1/1944 | Brace |
| 3,090,753 | A | 5/1963 | Matuszak et al. |
| 3,601,480 | A | 8/1971 | Randall |
| 3,856,000 | A | 12/1974 | Chikama |

(Continued)

FOREIGN PATENT DOCUMENTS

CN        1550203        12/2004

(Continued)

OTHER PUBLICATIONS

Fujimoto et al., "High Resolution in Vivo Intra-Arterial Imaging with Optical Coherence Tomography," *Official Journal of the British Cardiac Society*, vol. 82, pp. 128-133 Heart, 1999.

(Continued)

*Primary Examiner* — Michael A Lyons
(74) *Attorney, Agent, or Firm* — Dorsey & Whitney LLP

(57) ABSTRACT

Speckle, a factor reducing image quality in optical coherence tomography ("OCT"), can limit the ability to identify cellular structures that are important for the diagnosis of a variety of diseases. Exemplary embodiments of the present invention can facilitate an implementation of an angular compounding, angular compounding by path length encoding ("ACPE") for reducing speckle in OCT images. By averaging images obtained at different incident angles, with each image encoded by path length, ACPE maintains high-speed image acquisition and implements minimal modifications to OCT probe optics. ACPE images obtained from tissue phantoms and human skin in vivo demonstrate a qualitative improvement over traditional OCT and an increased signal-to-noise ratio ("SNR"). Accordingly, exemplary embodiments of an apparatus probe catheter and method can be provided for irradiating a structure. In particular, an interferometer may forward forwarding an electromagnetic radiation. In addition, a sample arm may receive the electromagnetic radiation, and can include an arrangement which facilitates a production of at least two radiations from the electromagnetic radiation so as to irradiate the structure. Such exemplary arrangement can be configured to delay a first radiation of the at least two radiations with respect to a second radiation of the at least two radiations.

22 Claims, 3 Drawing Sheets

U.S. PATENT DOCUMENTS

| | | | |
|---|---|---|---|
| 3,872,407 A | 3/1975 | Hughes | |
| 3,941,121 A | 3/1976 | Olinger | |
| 3,973,219 A | 8/1976 | Tang et al. | |
| 3,983,507 A | 9/1976 | Tang et al. | |
| 4,030,827 A | 6/1977 | Delhaye et al. | |
| 4,030,831 A | 6/1977 | Gowrinathan | |
| 4,140,364 A | 2/1979 | Yamashita et al. | |
| 4,141,362 A | 2/1979 | Wurster | |
| 4,224,929 A | 9/1980 | Furihata | |
| 4,295,738 A | 10/1981 | Meltz et al. | |
| 4,300,816 A | 11/1981 | Snitzer et al. | |
| 4,303,300 A | 12/1981 | Pressiat et al. | |
| 4,428,643 A | 1/1984 | Kay | |
| 4,479,499 A | 10/1984 | Alfano | |
| 4,533,247 A | 8/1985 | Epworth | |
| 4,585,349 A | 4/1986 | Gross et al. | |
| 4,601,036 A | 7/1986 | Faxvog et al. | |
| 4,607,622 A | 8/1986 | Fritch et al. | |
| 4,631,498 A | 12/1986 | Cutler | |
| 4,639,999 A | 2/1987 | Daniele | |
| 4,650,327 A | 3/1987 | Ogi | |
| 4,734,578 A | 3/1988 | Horikawa | |
| 4,744,656 A | 5/1988 | Moran et al. | |
| 4,751,706 A | 6/1988 | Rohde et al. | |
| 4,763,977 A | 8/1988 | Kawasaki et al. | |
| 4,770,492 A | 9/1988 | Levin et al. | |
| 4,827,907 A | 5/1989 | Tashiro et al. | |
| 4,834,111 A | 5/1989 | Khanna et al. | |
| 4,868,834 A | 9/1989 | Fox et al. | |
| 4,890,901 A * | 1/1990 | Cross, Jr. | 349/194 |
| 4,892,406 A | 1/1990 | Waters | |
| 4,905,169 A | 2/1990 | Buican et al. | |
| 4,909,631 A * | 3/1990 | Tan et al. | 356/632 |
| 4,925,302 A | 5/1990 | Cutler | |
| 4,928,005 A | 5/1990 | Lefèvre et al. | |
| 4,940,328 A | 7/1990 | Hartman | |
| 4,965,441 A | 10/1990 | Picard | |
| 4,965,599 A | 10/1990 | Roddy et al. | |
| 4,966,589 A | 10/1990 | Kaufman | |
| 4,984,888 A | 1/1991 | Tobias et al. | |
| 4,993,834 A | 2/1991 | Carlhoff et al. | |
| 4,998,972 A | 3/1991 | Chin et al. | |
| 5,039,193 A | 8/1991 | Snow et al. | |
| 5,040,889 A | 8/1991 | Keane | |
| 5,045,936 A | 9/1991 | Lobb et al. | |
| 5,046,501 A | 9/1991 | Crilly | |
| 5,065,331 A | 11/1991 | Vachon et al. | |
| 5,085,496 A * | 2/1992 | Yoshida et al. | 359/569 |
| 5,120,953 A | 6/1992 | Harris | |
| 5,121,983 A * | 6/1992 | Lee | 353/8 |
| 5,127,730 A | 7/1992 | Brelje et al. | |
| 5,197,470 A | 3/1993 | Helfer et al. | |
| 5,202,745 A | 4/1993 | Sorin et al. | |
| 5,202,931 A | 4/1993 | Bacus et al. | |
| 5,208,651 A | 5/1993 | Buican | |
| 5,212,667 A | 5/1993 | Tomlinson et al. | |
| 5,214,538 A | 5/1993 | Lobb | |
| 5,217,456 A | 6/1993 | Narciso, Jr. | |
| 5,228,001 A | 7/1993 | Birge et al. | |
| 5,241,364 A | 8/1993 | Kimura et al. | |
| 5,248,876 A | 9/1993 | Kerstens et al. | |
| 5,250,186 A | 10/1993 | Dollinger et al. | |
| 5,251,009 A | 10/1993 | Bruno | |
| 5,262,644 A | 11/1993 | Maguire | |
| 5,275,594 A | 1/1994 | Baker | |
| 5,281,811 A | 1/1994 | Lewis | |
| 5,283,795 A | 2/1994 | Fink | |
| 5,291,885 A | 3/1994 | Taniji et al. | |
| 5,293,872 A | 3/1994 | Alfano et al. | |
| 5,293,873 A | 3/1994 | Fang | |
| 5,302,025 A | 4/1994 | Kleinerman | |
| 5,304,173 A | 4/1994 | Kittrell et al. | |
| 5,304,810 A | 4/1994 | Amos | |
| 5,305,759 A | 4/1994 | Kaneko et al. | |
| 5,317,389 A | 5/1994 | Hochberg et al. | |
| 5,318,024 A | 6/1994 | Kittrell et al. | |
| 5,321,501 A | 6/1994 | Swanson et al. | |
| 5,348,003 A | 9/1994 | Caro | |
| 5,353,790 A | 10/1994 | Jacques et al. | |
| 5,383,467 A | 1/1995 | Auer et al. | |
| 5,394,235 A | 2/1995 | Takeuchi et al. | |
| 5,404,415 A | 4/1995 | Mori et al. | |
| 5,411,016 A | 5/1995 | Kume et al. | |
| 5,419,323 A | 5/1995 | Kittrell et al. | |
| 5,424,827 A | 6/1995 | Horwitz et al. | |
| 5,439,000 A | 8/1995 | Gunderson et al. | |
| 5,441,053 A | 8/1995 | Lodder et al. | |
| 5,450,203 A | 9/1995 | Penkethman | |
| 5,454,807 A | 10/1995 | Lennox et al. | |
| 5,459,325 A | 10/1995 | Hueton et al. | |
| 5,459,570 A | 10/1995 | Swanson et al. | |
| 5,465,147 A | 11/1995 | Swanson | |
| 5,486,701 A | 1/1996 | Norton et al. | |
| 5,491,524 A | 2/1996 | Hellmuth et al. | |
| 5,491,552 A | 2/1996 | Knuttel | |
| 5,522,004 A | 5/1996 | Djupsjobacka et al. | |
| 5,526,338 A | 6/1996 | Hasman et al. | |
| 5,555,087 A | 9/1996 | Miyagawa et al. | |
| 5,562,100 A | 10/1996 | Kittrell et al. | |
| 5,565,983 A | 10/1996 | Barnard et al. | |
| 5,565,986 A | 10/1996 | Knüttel | |
| 5,566,267 A | 10/1996 | Neuberger | |
| 5,583,342 A | 12/1996 | Ichie | |
| 5,590,660 A | 1/1997 | MacAulay et al. | |
| 5,600,486 A | 2/1997 | Gal et al. | |
| 5,601,087 A | 2/1997 | Gunderson et al. | |
| 5,621,830 A | 4/1997 | Lucey et al. | |
| 5,623,336 A | 4/1997 | Raab et al. | |
| 5,635,830 A * | 6/1997 | Itoh | 324/96 |
| 5,649,924 A | 7/1997 | Everett et al. | |
| 5,697,373 A | 12/1997 | Richards-Kortum et al. | |
| 5,698,397 A | 12/1997 | Zarling et al. | |
| 5,710,630 A | 1/1998 | Essenpreis et al. | |
| 5,716,324 A | 2/1998 | Toida | |
| 5,719,399 A | 2/1998 | Alfano et al. | |
| 5,730,731 A | 3/1998 | Mollenauer et al. | |
| 5,735,276 A | 4/1998 | Lemelson | |
| 5,740,808 A | 4/1998 | Panescu et al. | |
| 5,748,318 A | 5/1998 | Maris et al. | |
| 5,748,598 A | 5/1998 | Swanson et al. | |
| 5,752,518 A | 5/1998 | McGee et al. | |
| 5,784,352 A | 7/1998 | Swanson et al. | |
| 5,785,651 A | 7/1998 | Kuhn et al. | |
| 5,795,295 A | 8/1998 | Hellmuth et al. | |
| 5,801,826 A | 9/1998 | Williams | |
| 5,801,831 A | 9/1998 | Sargoytchev et al. | |
| 5,803,082 A | 9/1998 | Stapleton et al. | |
| 5,807,261 A | 9/1998 | Benaron et al. | |
| 5,810,719 A | 9/1998 | Toida | |
| 5,817,144 A | 10/1998 | Gregory | |
| 5,836,877 A | 11/1998 | Zavislan et al. | |
| 5,840,023 A | 11/1998 | Oraevsky et al. | |
| 5,840,075 A | 11/1998 | Mueller et al. | |
| 5,842,995 A | 12/1998 | Mahadevan-Jansen et al. | |
| 5,843,000 A | 12/1998 | Nishioka et al. | |
| 5,843,052 A | 12/1998 | Benja-Athon | |
| 5,847,827 A | 12/1998 | Fercher | |
| 5,862,273 A | 1/1999 | Pelletier | |
| 5,865,754 A | 2/1999 | Sevick-Muraca et al. | |
| 5,867,268 A | 2/1999 | Gelikonov et al. | |
| 5,871,449 A | 2/1999 | Brown | |
| 5,872,879 A | 2/1999 | Hamm | |
| 5,877,856 A | 3/1999 | Fercher | |
| 5,887,009 A | 3/1999 | Mandella et al. | |
| 5,892,583 A | 4/1999 | Li | |
| 5,910,839 A | 6/1999 | Erskine et al. | |
| 5,912,764 A | 6/1999 | Togino | |
| 5,920,373 A | 7/1999 | Bille | |
| 5,920,390 A | 7/1999 | Farahi et al. | |
| 5,921,926 A | 7/1999 | Rolland et al. | |
| 5,926,592 A | 7/1999 | Harris et al. | |
| 5,949,929 A | 9/1999 | Hamm | |
| 5,951,482 A | 9/1999 | Winston et al. | |
| 5,955,737 A | 9/1999 | Hallidy et al. | |
| 5,956,355 A | 9/1999 | Swanson et al. | |
| 5,968,064 A | 10/1999 | Selmon et al. | |
| 5,975,697 A | 11/1999 | Podoleanu et al. | |

| Patent No. | Date | Inventor |
|---|---|---|
| 5,983,125 A | 11/1999 | Alfano et al. |
| 5,987,346 A | 11/1999 | Benaron et al. |
| 5,991,697 A | 11/1999 | Nelson et al. |
| 5,994,690 A | 11/1999 | Kulkarni et al. |
| 5,995,223 A | 11/1999 | Power |
| 6,002,480 A | 12/1999 | Izatt et al. |
| 6,004,314 A | 12/1999 | Wei et al. |
| 6,006,128 A | 12/1999 | Izatt et al. |
| 6,007,996 A | 12/1999 | McNamara et al. |
| 6,010,449 A | 1/2000 | Selmon et al. |
| 6,014,214 A * | 1/2000 | Li .................................... 356/511 |
| 6,016,197 A | 1/2000 | Krivoshlykov |
| 6,020,963 A | 2/2000 | Dimarzio et al. |
| 6,025,956 A | 2/2000 | Nagano et al. |
| 6,033,721 A | 3/2000 | Nassuphis |
| 6,037,579 A | 3/2000 | Chan et al. |
| 6,044,288 A | 3/2000 | Wake et al. |
| 6,045,511 A | 4/2000 | Ott et al. |
| 6,048,742 A | 4/2000 | Weyburne et al. |
| 6,053,613 A | 4/2000 | Wei et al. |
| 6,069,698 A | 5/2000 | Ozawa et al. |
| 6,078,047 A | 6/2000 | Mittleman et al. |
| 6,091,496 A | 7/2000 | Hill |
| 6,091,984 A | 7/2000 | Perelman et al. |
| 6,094,274 A | 7/2000 | Yokoi |
| 6,107,048 A | 8/2000 | Goldenring et al. |
| 6,111,645 A | 8/2000 | Tearney et al. |
| 6,117,128 A | 9/2000 | Gregory |
| 6,120,516 A | 9/2000 | Selmon et al. |
| 6,134,003 A | 10/2000 | Tearney et al. |
| 6,134,010 A | 10/2000 | Zavislan |
| 6,134,033 A | 10/2000 | Bergano et al. |
| 6,141,577 A | 10/2000 | Rolland et al. |
| 6,151,522 A | 11/2000 | Alfano et al. |
| 6,159,445 A | 12/2000 | Klaveness et al. |
| 6,160,826 A | 12/2000 | Swanson et al. |
| 6,161,031 A | 12/2000 | Hochmann et al. |
| 6,166,373 A | 12/2000 | Mao |
| 6,174,291 B1 | 1/2001 | McMahon et al. |
| 6,175,669 B1 | 1/2001 | Colston et al. |
| 6,185,271 B1 | 2/2001 | Kinsinger |
| 6,191,862 B1 | 2/2001 | Swanson et al. |
| 6,193,676 B1 | 2/2001 | Winston et al. |
| 6,198,956 B1 | 3/2001 | Dunne |
| 6,201,989 B1 | 3/2001 | Whitehead et al. |
| 6,208,415 B1 | 3/2001 | De Boer et al. |
| 6,208,887 B1 | 3/2001 | Clarke |
| 6,245,026 B1 | 6/2001 | Campbell et al. |
| 6,249,349 B1 | 6/2001 | Lauer |
| 6,249,381 B1 | 6/2001 | Suganuma |
| 6,249,630 B1 | 6/2001 | Stock et al. |
| 6,263,234 B1 | 7/2001 | Engelhardt et al. |
| 6,264,610 B1 | 7/2001 | Zhu |
| 6,272,376 B1 | 8/2001 | Marcu et al. |
| 6,274,871 B1 | 8/2001 | Dukor et al. |
| 6,282,011 B1 | 8/2001 | Tearney et al. |
| 6,297,018 B1 | 10/2001 | French et al. |
| 6,301,048 B1 | 10/2001 | Cao et al. |
| 6,308,092 B1 | 10/2001 | Hoyns |
| 6,324,419 B1 | 11/2001 | Guzelsu et al. |
| 6,341,036 B1 | 1/2002 | Tearney et al. |
| 6,353,693 B1 | 3/2002 | Kano et al. |
| 6,359,692 B1 | 3/2002 | Groot |
| 6,374,128 B1 | 4/2002 | Toida et al. |
| 6,377,349 B1 | 4/2002 | Fercher |
| 6,384,915 B1 | 5/2002 | Everett et al. |
| 6,393,312 B1 | 5/2002 | Hoyns |
| 6,394,964 B1 | 5/2002 | Sievert, Jr. et al. |
| 6,396,941 B1 | 5/2002 | Bacus et al. |
| 6,421,164 B2 | 7/2002 | Tearney et al. |
| 6,437,867 B2 | 8/2002 | Zeylikovich et al. |
| 6,441,892 B2 | 8/2002 | Xiao et al. |
| 6,441,959 B1 | 8/2002 | Yang et al. |
| 6,445,485 B1 * | 9/2002 | Frigo et al. .................... 359/246 |
| 6,445,939 B1 | 9/2002 | Swanson et al. |
| 6,445,944 B1 | 9/2002 | Ostrovsky |
| 6,459,487 B1 | 10/2002 | Chen et al. |
| 6,463,313 B1 | 10/2002 | Winston et al. |
| 6,469,846 B2 | 10/2002 | Ebizuka et al. |
| 6,475,159 B1 | 11/2002 | Casscells et al. |
| 6,475,210 B1 | 11/2002 | Phelps et al. |
| 6,477,403 B1 | 11/2002 | Eguchi et al. |
| 6,485,413 B1 | 11/2002 | Boppart et al. |
| 6,485,482 B1 | 11/2002 | Belef |
| 6,501,551 B1 | 12/2002 | Tearney et al. |
| 6,501,878 B2 | 12/2002 | Hughes et al. |
| 6,516,014 B1 | 2/2003 | Sellin et al. |
| 6,517,532 B1 | 2/2003 | Altshuler et al. |
| 6,538,817 B1 | 3/2003 | Farmer et al. |
| 6,540,391 B2 | 4/2003 | Lanzetta et al. |
| 6,549,801 B1 | 4/2003 | Chen et al. |
| 6,552,796 B2 | 4/2003 | Magnin et al. |
| 6,556,305 B1 | 4/2003 | Aziz et al. |
| 6,556,853 B1 | 4/2003 | Cabib et al. |
| 6,558,324 B1 | 5/2003 | Von Behren et al. |
| 6,564,087 B1 | 5/2003 | Pitris et al. |
| 6,564,089 B2 | 5/2003 | Izatt et al. |
| 6,567,585 B2 | 5/2003 | Harris |
| 6,593,101 B2 | 7/2003 | Richards-Kortum et al. |
| 6,611,833 B1 | 8/2003 | Johnson et al. |
| 6,615,071 B1 | 9/2003 | Casscells, III et al. |
| 6,622,732 B2 | 9/2003 | Constantz |
| 6,654,127 B2 | 11/2003 | Everett et al. |
| 6,657,730 B2 | 12/2003 | Pfau et al. |
| 6,658,278 B2 | 12/2003 | Gruhl |
| 6,680,780 B1 | 1/2004 | Fee |
| 6,685,885 B2 | 2/2004 | Nolte et al. |
| 6,687,007 B1 | 2/2004 | Meigs |
| 6,687,010 B1 | 2/2004 | Horii et al. |
| 6,687,036 B2 | 2/2004 | Riza |
| 6,692,430 B2 | 2/2004 | Adler |
| 6,701,181 B2 | 3/2004 | Tang et al. |
| 6,721,094 B1 | 4/2004 | Sinclair et al. |
| 6,738,144 B1 | 5/2004 | Dogariu et al. |
| 6,741,355 B2 | 5/2004 | Drabarek |
| 6,757,467 B1 | 6/2004 | Rogers |
| 6,790,175 B1 | 9/2004 | Furusawa et al. |
| 6,806,963 B1 | 10/2004 | Wälti et al. |
| 6,816,743 B2 | 11/2004 | Moreno et al. |
| 6,831,781 B2 | 12/2004 | Tearney et al. |
| 6,839,496 B1 | 1/2005 | Mills et al. |
| 6,882,432 B2 | 4/2005 | Deck |
| 6,900,899 B2 | 5/2005 | Nevis |
| 6,903,820 B2 | 6/2005 | Wang |
| 6,909,105 B1 | 6/2005 | Heintzmann et al. |
| 6,949,072 B2 | 9/2005 | Furnish et al. |
| 6,961,123 B1 | 11/2005 | Wang et al. |
| 6,980,299 B1 | 12/2005 | de Boer |
| 6,996,549 B2 | 2/2006 | Zhang et al. |
| 7,006,231 B2 | 2/2006 | Ostrovsky et al. |
| 7,006,232 B2 | 2/2006 | Rollins et al. |
| 7,019,838 B2 | 3/2006 | Izatt et al. |
| 7,027,633 B2 | 4/2006 | Foran et al. |
| 7,061,622 B2 | 6/2006 | Rollins et al. |
| 7,072,047 B2 | 7/2006 | Westphal et al. |
| 7,075,658 B2 | 7/2006 | Izatt et al. |
| 7,099,358 B1 | 8/2006 | Chong et al. |
| 7,113,288 B2 | 9/2006 | Fercher |
| 7,113,625 B2 | 9/2006 | Watson et al. |
| 7,130,320 B2 | 10/2006 | Tobiason et al. |
| 7,139,598 B2 | 11/2006 | Hull et al. |
| 7,142,835 B2 | 11/2006 | Paulus |
| 7,148,970 B2 | 12/2006 | De Boer |
| 7,177,027 B2 | 2/2007 | Hirasawa et al. |
| 7,190,464 B2 | 3/2007 | Alphonse |
| 7,230,708 B2 | 6/2007 | Lapotko et al. |
| 7,231,243 B2 | 6/2007 | Tearney et al. |
| 7,236,637 B2 | 6/2007 | Sirohey et al. |
| 7,242,480 B2 | 7/2007 | Alphonse |
| 7,267,494 B2 | 9/2007 | Deng et al. |
| 7,272,252 B2 | 9/2007 | De La Torre-Bueno et al. |
| 7,304,798 B2 | 12/2007 | Izumi et al. |
| 7,330,270 B2 | 2/2008 | O'Hara et al. |
| 7,336,366 B2 | 2/2008 | Choma et al. |
| 7,342,659 B2 | 3/2008 | Horn et al. |
| 7,355,716 B2 | 4/2008 | De Boer et al. |
| 7,355,721 B2 | 4/2008 | Quadling et al. |
| 7,359,062 B2 | 4/2008 | Chen et al. |

| Patent/Pub. No. | Date | Inventors |
|---|---|---|
| 7,366,376 B2 | 4/2008 | Shishkov et al. |
| 7,382,809 B2 | 6/2008 | Chong et al. |
| 7,391,520 B2 | 6/2008 | Zhou et al. |
| 7,458,683 B2 | 12/2008 | Chernyak et al. |
| 7,530,948 B2 | 5/2009 | Seibel et al. |
| 7,539,530 B2 | 5/2009 | Caplan et al. |
| 7,609,391 B2 | 10/2009 | Betzig |
| 7,630,083 B2 | 12/2009 | de Boer et al. |
| 7,643,152 B2 | 1/2010 | de Boer et al. |
| 7,643,153 B2 | 1/2010 | de Boer et al. |
| 7,646,905 B2 | 1/2010 | Guittet et al. |
| 7,649,160 B2 | 1/2010 | Colomb et al. |
| 7,664,300 B2 | 2/2010 | Lange et al. |
| 7,733,497 B2 | 6/2010 | Yun et al. |
| 7,782,464 B2 | 8/2010 | Mujat et al. |
| 7,805,034 B2 | 9/2010 | Kato et al. |
| 2001/0036002 A1 | 11/2001 | Tearney et al. |
| 2001/0047137 A1 | 11/2001 | Moreno et al. |
| 2002/0016533 A1 | 2/2002 | Marchitto et al. |
| 2002/0024015 A1 | 2/2002 | Hoffmann et al. |
| 2002/0048025 A1 | 4/2002 | Takaoka |
| 2002/0048026 A1 | 4/2002 | Isshiki et al. |
| 2002/0052547 A1 | 5/2002 | Toida |
| 2002/0057431 A1 | 5/2002 | Fateley et al. |
| 2002/0064341 A1 | 5/2002 | Fauver et al. |
| 2002/0076152 A1 | 6/2002 | Hughes et al. |
| 2002/0085209 A1 | 7/2002 | Mittleman et al. |
| 2002/0086347 A1 | 7/2002 | Johnson et al. |
| 2002/0091322 A1 | 7/2002 | Chaiken et al. |
| 2002/0093662 A1 | 7/2002 | Chen et al. |
| 2002/0109851 A1 | 8/2002 | Deck |
| 2002/0122182 A1 | 9/2002 | Everett et al. |
| 2002/0122246 A1 | 9/2002 | Tearney et al. |
| 2002/0140942 A1 | 10/2002 | Fee et al. |
| 2002/0158211 A1 | 10/2002 | Gillispie |
| 2002/0161357 A1 | 10/2002 | Anderson et al. |
| 2002/0163622 A1 | 11/2002 | Magnin et al. |
| 2002/0168158 A1 | 11/2002 | Furusawa et al. |
| 2002/0172485 A1 | 11/2002 | Keaton et al. |
| 2002/0183623 A1 | 12/2002 | Tang et al. |
| 2002/0188204 A1 | 12/2002 | McNamara et al. |
| 2002/0196446 A1 | 12/2002 | Roth et al. |
| 2002/0198457 A1 | 12/2002 | Tearney et al. |
| 2003/0001071 A1 | 1/2003 | Mandella et al. |
| 2003/0013973 A1 | 1/2003 | Georgakoudi et al. |
| 2003/0023153 A1 | 1/2003 | Izatt et al. |
| 2003/0026735 A1 | 2/2003 | Nolte et al. |
| 2003/0028114 A1 | 2/2003 | Casscells, III et al. |
| 2003/0030816 A1 | 2/2003 | Eom et al. |
| 2003/0043381 A1 | 3/2003 | Fercher |
| 2003/0053673 A1 | 3/2003 | Dewaele et al. |
| 2003/0067607 A1 | 4/2003 | Wolleschensky et al. |
| 2003/0082105 A1 | 5/2003 | Fischman et al. |
| 2003/0097048 A1 | 5/2003 | Ryan et al. |
| 2003/0108911 A1 | 6/2003 | Klimant et al. |
| 2003/0120137 A1 | 6/2003 | Pawluczyk et al. |
| 2003/0135101 A1 | 7/2003 | Webler |
| 2003/0137669 A1 | 7/2003 | Rollins et al. |
| 2003/0164952 A1 | 9/2003 | Deichmann et al. |
| 2003/0165263 A1 | 9/2003 | Hamer et al. |
| 2003/0171691 A1 | 9/2003 | Casscells, III et al. |
| 2003/0174339 A1 | 9/2003 | Feldchtein et al. |
| 2003/0199769 A1 | 10/2003 | Podoleanu et al. |
| 2003/0216719 A1 | 11/2003 | Debenedictis et al. |
| 2003/0220749 A1 | 11/2003 | Chen et al. |
| 2003/0236443 A1 | 12/2003 | Cespedes et al. |
| 2004/0002650 A1 | 1/2004 | Mandrusov et al. |
| 2004/0039298 A1 | 2/2004 | Abreu |
| 2004/0054268 A1 | 3/2004 | Esenaliev et al. |
| 2004/0072200 A1 | 4/2004 | Rigler et al. |
| 2004/0075841 A1 | 4/2004 | Van Neste et al. |
| 2004/0076940 A1 | 4/2004 | Alexander et al. |
| 2004/0077949 A1 | 4/2004 | Blofgett et al. |
| 2004/0085540 A1 | 5/2004 | Lapotko et al. |
| 2004/0086245 A1 | 5/2004 | Farroni et al. |
| 2004/0100631 A1 | 5/2004 | Bashkansky et al. |
| 2004/0100681 A1 | 5/2004 | Bjarklev et al. |
| 2004/0110206 A1 | 6/2004 | Wong et al. |
| 2004/0126048 A1 | 7/2004 | Dave et al. |
| 2004/0126120 A1 | 7/2004 | Cohen et al. |
| 2004/0133191 A1 | 7/2004 | Momiuchi et al. |
| 2004/0150829 A1 | 8/2004 | Koch et al. |
| 2004/0150830 A1 | 8/2004 | Chan |
| 2004/0152989 A1 | 8/2004 | Puttappa et al. |
| 2004/0165184 A1 | 8/2004 | Mizuno |
| 2004/0166593 A1 | 8/2004 | Nolte et al. |
| 2004/0189999 A1 | 9/2004 | De Groot et al. |
| 2004/0212808 A1 | 10/2004 | Okawa et al. |
| 2004/0239938 A1 | 12/2004 | Izatt et al. |
| 2004/0246490 A1 | 12/2004 | Wang |
| 2004/0246583 A1 | 12/2004 | Mueller et al. |
| 2004/0254474 A1 | 12/2004 | Seibel et al. |
| 2004/0263843 A1 | 12/2004 | Knopp et al. |
| 2005/0004453 A1 | 1/2005 | Tearney et al. |
| 2005/0018133 A1 | 1/2005 | Huang et al. |
| 2005/0018201 A1 | 1/2005 | De Boer |
| 2005/0035295 A1 | 2/2005 | Bouma et al. |
| 2005/0036150 A1 | 2/2005 | Izatt et al. |
| 2005/0046837 A1 | 3/2005 | Izumi et al. |
| 2005/0057680 A1 | 3/2005 | Agan |
| 2005/0057756 A1 | 3/2005 | Fang-Yen et al. |
| 2005/0059894 A1 | 3/2005 | Zeng et al. |
| 2005/0065421 A1 | 3/2005 | Burckhardt et al. |
| 2005/0075547 A1 | 4/2005 | Wang |
| 2005/0083534 A1 | 4/2005 | Riza et al. |
| 2005/0119567 A1 | 6/2005 | Choi et al. |
| 2005/0128488 A1 | 6/2005 | Yelin et al. |
| 2005/0165303 A1 | 7/2005 | Kleen et al. |
| 2005/0171438 A1 | 8/2005 | Chen et al. |
| 2005/0190372 A1 | 9/2005 | Dogariu et al. |
| 2005/0254061 A1 | 11/2005 | Alphonse et al. |
| 2006/0033923 A1 | 2/2006 | Hirasawa et al. |
| 2006/0093276 A1 | 5/2006 | Bouma et al. |
| 2006/0103850 A1 | 5/2006 | Alphonse et al. |
| 2006/0146339 A1 | 7/2006 | Fujita et al. |
| 2006/0155193 A1 | 7/2006 | Leonardi et al. |
| 2006/0164639 A1 | 7/2006 | Horn et al. |
| 2006/0171503 A1 | 8/2006 | O'Hara et al. |
| 2006/0184048 A1 | 8/2006 | Saadat et al. |
| 2006/0193352 A1 | 8/2006 | Chong et al. |
| 2006/0244973 A1 | 11/2006 | Yun et al. |
| 2006/0279742 A1 | 12/2006 | Tearney |
| 2007/0019208 A1 | 1/2007 | Toida et al. |
| 2007/0038040 A1 | 2/2007 | Cense et al. |
| 2007/0070496 A1 | 3/2007 | Gweon et al. |
| 2007/0076217 A1 | 4/2007 | Baker et al. |
| 2007/0086013 A1 | 4/2007 | De Lega et al. |
| 2007/0086017 A1 | 4/2007 | Buckland et al. |
| 2007/0091317 A1 | 4/2007 | Freischlad et al. |
| 2007/0133002 A1 | 6/2007 | Wax et al. |
| 2007/0188855 A1 | 8/2007 | Shishkov et al. |
| 2007/0223006 A1 | 9/2007 | Tearney et al. |
| 2007/0236700 A1 | 10/2007 | Yun et al. |
| 2007/0258094 A1 | 11/2007 | Izatt et al. |
| 2007/0291277 A1 | 12/2007 | Everett et al. |
| 2008/0002197 A1 | 1/2008 | Sun et al. |
| 2008/0007734 A1 | 1/2008 | Park et al. |
| 2008/0049220 A1 | 2/2008 | Izzia et al. |
| 2008/0094613 A1 | 4/2008 | de Boer et al. |
| 2008/0094637 A1 | 4/2008 | de Boer et al. |
| 2008/0097225 A1 | 4/2008 | Tearney et al. |
| 2008/0097709 A1 | 4/2008 | de Boer et al. |
| 2008/0100837 A1 | 5/2008 | de Boer et al. |
| 2008/0152353 A1 | 6/2008 | de Boer et al. |
| 2008/0154090 A1 | 6/2008 | Hashimshony |
| 2008/0204762 A1 | 8/2008 | Izatt et al. |
| 2008/0228086 A1 | 9/2008 | Ilegbusi |
| 2008/0265130 A1 | 10/2008 | Colomb et al. |
| 2008/0308730 A1 | 12/2008 | Vizi et al. |
| 2009/0005691 A1 | 1/2009 | Huang |
| 2009/0011948 A1 | 1/2009 | Uniu et al. |
| 2009/0196477 A1 | 8/2009 | Cense et al. |
| 2009/0273777 A1 | 11/2009 | Yun et al. |
| 2009/0290156 A1 | 11/2009 | Popescu et al. |
| 2010/0086251 A1 | 4/2010 | Xu et al. |
| 2010/0094576 A1 | 4/2010 | de Boer et al. |
| 2010/0150467 A1 | 6/2010 | Zhao et al. |

FOREIGN PATENT DOCUMENTS

| | | |
|---|---|---|
| DE | 4105221 | 9/1991 |
| DE | 4309056 | 9/1994 |
| DE | 19542955 | 5/1997 |
| DE | 10351319 | 6/2005 |
| EP | 0110201 | 6/1984 |
| EP | 0251062 | 1/1988 |
| EP | 0617286 | 2/1994 |
| EP | 0590268 | 4/1994 |
| EP | 0728440 | 8/1996 |
| EP | 0933096 | 8/1999 |
| EP | 1324051 | 7/2003 |
| EP | 1426799 | 6/2004 |
| FR | 2738343 | 8/1995 |
| GB | 1257778 | 12/1971 |
| GB | 2030313 | 4/1980 |
| GB | 2209221 | 5/1989 |
| GB | 2298054 | 8/1996 |
| JP | 6073405 | 4/1985 |
| JP | 20040056907 | 2/1992 |
| JP | 4135550 | 5/1992 |
| JP | 4135551 | 5/1992 |
| JP | 5509417 | 11/1993 |
| JP | 2002214127 | 7/2002 |
| JP | 20030035659 | 2/2003 |
| JP | 2007271761 | 10/2007 |
| WO | 7900841 | 10/1979 |
| WO | 9201966 | 2/1992 |
| WO | 9216865 | 10/1992 |
| WO | 9219930 | 11/1992 |
| WO | 9303672 | 3/1993 |
| WO | 9533971 | 12/1995 |
| WO | 9628212 | 9/1996 |
| WO | 9732182 | 9/1997 |
| WO | 9800057 | 1/1998 |
| WO | 9801074 | 1/1998 |
| WO | 9814132 | 4/1998 |
| WO | 9835203 | 8/1998 |
| WO | 9838907 | 9/1998 |
| WO | 9846123 | 10/1998 |
| WO | 9848811 | 11/1998 |
| WO | 9848846 | 11/1998 |
| WO | 9905487 | 2/1999 |
| WO | 9944089 | 2/1999 |
| WO | 9944089 | 9/1999 |
| WO | 9957507 | 11/1999 |
| WO | 0058766 | 10/2000 |
| WO | 0101111 | 1/2001 |
| WO | 0108579 | 2/2001 |
| WO | 0127679 | 4/2001 |
| WO | 0138820 | 5/2001 |
| WO | 0142735 | 6/2001 |
| WO | 0236015 | 5/2002 |
| WO | 0237075 | 5/2002 |
| WO | 0238040 | 5/2002 |
| WO | 02053050 | 7/2002 |
| WO | 02054027 | 7/2002 |
| WO | 02084263 | 10/2002 |
| WO | 03013624 | 2/2003 |
| WO | 03020119 | 3/2003 |
| WO | 03046495 | 6/2003 |
| WO | 03046636 | 6/2003 |
| WO | 03052478 | 6/2003 |
| WO | 03053226 | 7/2003 |
| WO | 03062802 | 7/2003 |
| WO | 03105678 | 12/2003 |
| WO | 2004034869 | 4/2004 |
| WO | 2004057266 | 7/2004 |
| WO | 2004066824 | 8/2004 |
| WO | 2004088361 | 10/2004 |
| WO | 2004105598 | 12/2004 |
| WO | 2005000115 | 1/2005 |
| WO | 2005047813 | 5/2005 |
| WO | 2005054780 | 6/2005 |
| WO | 2005082225 | 9/2005 |
| WO | 2006004743 | 1/2006 |
| WO | 2006014392 | 2/2006 |
| WO | 2006038876 | 4/2006 |
| WO | 2006039091 | 4/2006 |
| WO | 2006059109 | 6/2006 |
| WO | 2006124860 | 11/2006 |
| WO | 2006130797 | 12/2006 |
| WO | 2007028531 | 3/2007 |
| WO | 2007038787 | 4/2007 |
| WO | 2007083138 | 7/2007 |
| WO | 2007084995 | 7/2007 |

OTHER PUBLICATIONS

D. Huang et al., "Optical Coherence Tomography," *Science*, vol. 254, pp. 1178-1181, Nov. 1991.

Tearney et al., "High-Speed Phase—and Group Delay Scanning with a Grating Based Phase Control Delay Line," *Optics Letters*, vol. 22, pp. 1811-1813, Dec. 1997.

Rollins, et al., "In Vivo Video Rate Optical Coherence Tomography," *Optics Express*, vol. 3, pp. 219-229, Sep. 1998.

Saxer, et al., High Speed Fiber-Based Polarization-Sensitive Optical Coherence Tomogrphy of in Vivo Human Skin, *Optical Society of America*, vol. 25, pp. 1355-1357, Sep. 2000.

Oscar Eduardo Martinez, "3000 Times Grating Compress or with Positive Group Velocity Dispersion," *IEEE*, vol. QE-23, pp. 59-64, Jan. 1987.

Kulkarni, et al., "Image Enhancement in Optical Coherence Tomography Using Deconvolution," *Electronics Letters*, vol. 33, pp. 1365-1367, Jul. 1997.

Bashkansky, et al., "Signal Processing for Improving Field Cross-Correlation Function in Optical Coherence Tomography," *Optics & Photonics News*, vol. 9, pp. 8137-8138, May 1998.

Yung et al., "Phase-Domain Processing of Optical Coherence Tomography Images," *Journal of Biomedical Optics*, vol. 4, pp. 125-136, Jan. 1999.

Tearney, et al., "In Vivo Endoscopic Optical Biopsy with Optical Coherence Tomography," *Science*, vol. 276, Jun. 1997.

W. Drexler et al., "In Vivo Ultrahigh-Resolution Optical Coherence Tomography," *Optics Letters* vol. 24, pp. 1221-1223, Sep. 1999.

Nicusor V. Iftimia et al., (2005) "A Portable, Low Coherence Interferometry Based Instrument for Fine Needle Aspiration Biopsy Guidance," Accepted to Review of Scientific Instruments, published May 23, 2005.

Abbas, G.L., V.W.S. Chan et al., "Local-Oscillator Excess-Noise Suppression for Homodyne and Heterodyne-Detection," *Optics Letters*, vol. 8, pp. 419-421, Aug. 1983 issue.

Agrawal, G.P., "Population Pulsations and Nondegenerate 4-Wave Mixing in Semiconductor-Lasers and Amplifiers," *Journal of the Optical Society of America B-Optical Physics*, vol. 5, pp. 147-159, Jan. 1998.

Andretzky, P. et al., "Optical Coherence Tomography by Spectral Radar: Improvement of Signal-to-Noise Ratio," *The International Society for Optical Engineering*, USA, vol. 3915, 2000.

Ballif, J. et al., "Rapid and Scalable Scans at 21 m/s in optical Low-Coherence Reflectometry," *Optics Letters*, vol. 22, pp. 757-759, Jun. 1997.

Barfuss H. et al., "Modified Optical Frequency-Domain Reflectometry with High Spatial-Resolution for Components of Integrated Optic Systems," *Journal of Lightwave Technology*, vol. 7, pp. 3-10, Jan. 1989.

Beaud, P. et al., "Optical Reflectometry with Micrometer Resolution for the Investigation of Integrated Optical-Devices," *Ieee Journal of Quantum Electronics*, vol. 25, pp. 755-759, Apr. 1989.

Bouma, Brett et al., "Power-Efficient Nonreciprocal Interferometer and Linear-Scanning Fiber-Optic Catheter for Optical Coherence Tomography," *Optics Letters*, vol. 24, pp. 531-533, Apr. 1999.

Brinkmeyer, E. et al., "Efficient Algorithm for Non-Equidistant Interpolation of Sampled Data," *Electronics Letters*, vol. 28, p. 693, Mar. 1992.

Brinkmeyer, E. et al., "High-Resolution OCDR in Dispersive Wave-Guides," *Electronics Letters*, vol. 26, pp. 413-414, Mar. 1990.

Chinn, S.R. et al., "Optical Coherence Tomography Using a Frequency-Tunable Optical Source," *Optics Letters*, vol. 22, pp. 340-342, Mar. 1997.

Danielson, B.L. et al., "Absolute Optical Ranging Using Low Coherence Interferometry," *Applied Optics*, vol. 30, p. 2975, Jul. 1991.

Dorrer, C. et al., "Spectral Resolution and Sampling Issues in Fourier-Transform Spectral Interferometry," *Journal of the Optical Society of America B-Optical Physics*, vol. 17, pp. 1795-1802, Oct. 2000.

Dudley, J.M. et al., "Cross-Correlation Frequency Resolved Optical Gating Analysis of Broadband Continuum Generation in Photonic Crystal Fiber: Simulations and Experiments," *Optics Express*, vol. 10, p. 1215, Oct. 2002.

Eickhoff, W. et al., "Optical Frequency-Domain Reflectometry in Single-Mode Fiber," *Applied Physics Letters*, vol. 39, pp. 693-695, 1981.

Fercher, Adolf "Optical Coherence Tomography," *Journal of Biomedical Optics*, vol. 1, pp. 157-173, Apr. 1996.

Ferreira, L.A. et al., "Polarization-Insensitive Fiberoptic White-Light Interferometry," *Optics Communications*, vol. 114, pp. 386-392, Feb. 1995.

Fujii, Yohji, "High-Isolation Polarization-Independent Optical Circulator", *Journal of Lightwave Technology*, vol. 9, pp. 1239-1243, Oct. 1991.

Glance, B., "Polarization Independent Coherent Optical Receiver," *Journal of Lightwave Technology*, vol. LT-5, p. 274, Feb. 1987.

Glombitza, U., "Coherent Frequency-Domain Reflectometry for Characterization of Single-Mode Integrated-Optical Wave-Guides," *Journal of Lightwave Technology*, vol. 11, pp. 1377-1384, Aug. 1993.

Golubovic, B. et al., "Optical Frequency-Domain Reflectometry Using Rapid Wavelength Tuning of a Cr4+:Forsterite Laser," *Optics Letters*, vol. 11, pp. 1704-1706, Nov. 1997.

Haberland, U. H. P. et al., "Chirp Optical Coherence Tomography of Layered Scattering Media," *Journal of Biomedical Optics*, vol. 3, pp. 259-266, Jul. 1998.

Hammer, Daniel X. et al., "Spectrally Resolved White-Light Interferometry for Measurement of Ocular Dispersion," *Journal of the Optical Society of America A-Optics Image Science and Vision*, vol. 16, pp. 2092-2102, Sep. 1999.

Harvey, K. C. et al., "External-Cavity Diode-Laser Using a Grazing-Incidence Diffraction Grating," *Optics Letters*, vol. 16, pp. 910-912, Jun. 1991.

Hausler, Gerd et al., "'Coherence Radar' and 'Spectral Radar' New Tools for Dermatological Diagnosis," *Journal of Biomedical Optics*, vol. 3, pp. 21-31, Jan. 1998.

Hee, Michael R. et al., "Polarization-Sensitive Low-Coherence Reflectometer for Birefringence Characterization and Ranging," *Journal of the Optical Society of America B (Optical Physics)*, vol. 9, p. 903-908, Jun. 1992.

Hotate Kazuo et al., "Optical Coherence Domain Reflectometry by Synthesis of Coherence Function," *Journal of Lightwave Technology*, vol. 11, pp. 1701-1710, Oct. 1993.

Inoue, Kyo et al., "Nearly Degenerate 4-Wave-Mixing in a Traveling-Wave Semiconductor-Laser Amplifier," *Applied Physics Letters*, vol. 51, pp. 1051-5053, 1987.

Ivanov, A. P. et al., "New Method for High-Range Resolution Measurements of Light Scattering in Optically Dense Inhomogeneous Media," *Optics Letters*, vol. 1, pp. 226-228, Dec. 1977.

Ivanov, A. P. et al., "Interferometric Study of the Spatial Structure of a Light-Scattering Medium," *Journal of Applied Spectroscopy*, vol. 28, pp. 518-525, 1978.

Kazovsky, L. G. et al., "Heterodyne Detection Through Rain, Snow, and Turbid Media: Effective Receiver Size at Optical Through Millimeter Wavelenghths," *Applied Optics*, vol. 22, pp. 206-710, Mar. 1982.

Kersey, A. D. et al., "Adaptive Polarization Diversity Receiver Configuration for Coherent Optical Fiber Communications," *Electronics Letters*, vol. 25, pp. 275-277, Feb. 1989.

Kohlhaas, Andreas et al., "High-Resolution OCDR for Testing Integrated-Optical Waveguides: Dispersion-Corrupted Experimental Data Corrected by a Numerical Algorithm," *Journal of Lightwave Technology*, vol. 9, pp. 1493-1502, Nov. 1991.

Larkin, Kieran G., "Efficient Nonlinear Algorithm for Envelope Detection in White Light Interferometry," *Journal of the Optical Society of America A-Optics Image Science and Vision*, vol. 13, pp. 832-843, Apr. 1996.

Leitgeb, R. et al., "Spectral measurement of Absorption by Spectroscopic Frequency-Domain Optical Coherence Tomography," *Optics Letters*, vol. 25, pp. 820-822, Jun. 2000.

Lexer, F. et al., "Wavelength-Tuning Interferometry of Intraocular Distances," *Applied Optics*, vol. 36, pp. 6548-6553, Sep. 1997.

Mitsui, Takahisa, "Dynamic Range of Optical Reflectometry with Spectral Interferometry," *Japanese Journal of Applied Physics Part 1—Regular Papers Short Notes & Review Papers*, vol. 38, pp. 6133-6137, 1999.

Naganuma, Kazunori et al., "Group-Delay Measurement Using the Fourier-Transform of an Interferometric Cross-Correlation Generated by White Light," *Optics Letters*, vol. 15, pp. 393-395, Apr. 1990.

Okoshi,Takanori, "Polarization-State Control Schemes for Heterodyne or Homodyne Optical Fiber Communications," *Journal of Lightwave Technology*, vol. LT-3, pp. 1232-1237, Dec. 1995.

Passy, R. et al., "Experimental and Theoretical Investigations of Coherent OFDR with Semiconductor-Laser Sources," *Journal of Lightwave Technology*, vol. 12, pp. 1622-1630, Sep. 1994.

Podoleanu, Adrian G., "Unbalanced Versus Balanced Operation in an Optical Coherence Tomography System," *Applied Optics*, vol. 39, pp. 173-182, Jan. 2000.

Price, J. H. V. et al., "Tunable, Femtosecond Pulse Source Operating in the Range 1.06-1.33 mu m Based on an Yb3+-doped Holey Fiber Amplifier," *Journal of the Optical Society of America B-Optical Physics*, vol. 19, pp. 1286-1294, Jun. 2002.

Schmitt, J. M. et al, "Measurement of Optical-Properties of Biological Tissues By Low-Coherence Reflectometry," *Applied Optics*, vol. 32, pp. 6032-6042, Oct. 1993.

Silberberg, Y. et al., "Passive-Mode Locking of a Semiconductor Diode-Laser," *Optics Letters*, vol. 9, pp. 507-509, Nov. 1984.

Smith, L. Montgomery et al., "Absolute Displacement Measurements Using Modulation of the Spectrum of White-Light in a Michelson Interferometer," *Applied Optics*, vol. 28, pp. 3339-3342, Aug. 1989.

Sonnenschein, C. M. et al., "Signal-To-Noise Relationships for Coaxial Systems that Heterodyne Backscatter from Atmosphere," *Applied Optics*, vol. 10, pp. 1600-1604, Jul. 1971.

Sorin, W. V. et al., "Measurement of Rayleigh Backscattering at 1.55 mu m with 32 mu m Spatial Resolution," *IEEE Photonics Technology Letters*, vol. 4, pp. 374-376, Apr. 1992.

Sorin, W. V. et al., "A Simple Intensity Noise-Reduction Technique for Optical Low-Coherence Reflectometry," *IEEE Photonics Technology Letters*, vol. 4, pp. 1404-1406, Dec. 1992.

Swanson, E. A. et al., "High-Speed Optical Coherence Domain Reflectometry," *Optics Letters*, vol. 17, pp. 151-153, Jan. 1992.

Takada, K. et al., "High-Resolution OFDR with Incorporated Fiberoptic Frequency Encoder," *IEEE Photonics Technology Letters*, vol. 4, pp. 1069-1072, Sep. 1992.

Takada, Kazumasa et al., "Narrow-Band light Source with Acoustooptic Tunable Filter for Optical Low-Coherence Reflectometry," *IEEE Photonics Technology Letters*, vol. 8, pp. 658-660, May 1996.

Takada, Kazumasa et al., "New Measurement System for Fault Location in Optical Wave-Guide Devices Based on an Interometric-Technique," *Applied Optics*, vol. 26, pp. 1603-1606, May 1987.

Tateda, Mitsuhiro et al., "Interferometric Method for Chromatic Dispersion Measurement in a Single-Mode Optical Fiber," *IEEE Journal of Quantum Electronics*, vol. 17, pp. 404-407, Mar. 1981.

Toide, M. et al., "Two-Dimensional Coherent Detection Imaging in Multiple Scattering Media Based the Directional Resolution Capability of the Optical Heterodyne Method," *Applied Physics B (Photophysics and Laser Chemistry)*, vol. B52, pp. 391-394, 1991.

Trutna, W. R. et al., "Continuously Tuned External-Cavity Semiconductor-Laser," *Journal of Lightwave Technology*, vol. 11, pp. 1279-1286, Aug. 1993.

Uttam, Deepak et al., "Precision Time Domain Reflectometry in Optical Fiber Systems Using a Frequency Modulated Continuous Wave Ranging Technique," *Journal of Lightwave Technology*, vol. 3, pp. 971-977, Oct. 1985.

Von Der Weid, J. P. et al., "On the Characterization of Optical Fiber Network Components with Optical Frequency Domain Reflectometry," *Journal of Lightwave Technology*, vol. 15, pp. 1131-1141, Jul. 1997.

Wysocki, P.F. et al., "Broad-Spectrum, Wavelength-Swept, Erbium-Doped Fiber Laser at 1.55-Mu-M," *Optics Letters*, vol. 15, pp. 879-881, Aug. 1990.

Youngquist, Robert C. et al., "Optical Coherence-Domain Reflectometry—A New Optical Evaluation Technique," *Optics Letters*, vol. 12, pp. 158-160, Mar. 1987.

Yun, S. H. et al., "Wavelength-Swept Fiber Laser with Frequency Shifted Feedback and Resonantly Swept Intra-Cavity Acoustooptic Tunable Filter," *IEEE Journal of Selected Topics in Quantum Electronics*, vol. 3, pp. 1087-1096, Aug. 1997.

Yun, S. H. et al., "Interrogation of Fiber Grating Sensor Arrays with a Wavelength-Swept Fiber Laser," *Optics Letters*, vol. 23, pp. 843-845, Jun. 1998.

Yung, K. M., "Phase-Domain Processing of Optical Coherence Tomography Images," *Journal of Biomedical Optics*, vol. 4, pp. 125-136, Jan. 1999.

Zhou, Xiao-Qun et al., "Extended-Range FMCW Reflectometry Using an optical Loop with a Frequency Shifter," *IEEE Photonics Technology Letters*, vol. 8, pp. 248-250, Feb. 1996.

Zorabedian, Paul et al., "Tuning Fidelity of Acoustooptically Controlled External Cavity Semiconductor-Lasers," *Journal of Lightwave Technology*, vol. 13, pp. 62-66, Jan. 1995.

Victor S. Y. Lin et al., "A Porous Silicon-Based Optical Interferometric Biosensor," *Science Magazine*, vol. 278, pp. 840-843, Oct. 31, 1997.

De Boer, Johannes F. et al., "Review of Polarization Sensitive Optical Coherence Tomography and Stokes Vector Determination," *Journal of Biomedical Optics*, vol. 7, No. 3, Jul. 2002, pp. 359-371.

Jiao, Shuliang et al., "Depth-Resolved Two-Dimensional Stokes Vectors of Backscattered Light and Mueller Matrices of Biological Tissue Measured with Optical Coherence Tomography," *Applied Optics*, vol. 39, No. 34, Dec. 1, 2000, pp. 6318-6324.

Park, B. Hyle et al., "In Vivo Burn Depth Determination by High-Speed Fiber-Based Polarization Sensitive Optical Coherence Tomography," *Journal of Biomedical Optics*, vol. 6 No. 4, Oct. 2001, pp. 474-479.

Roth, Jonathan E. et al., "Simplified Method for Polarization-Sensitive Optical Coherence Tomography," *Optics Letters*, vol. 26, No. 14, Jul. 15, 2001, pp. 1069-1071.

Hitzenberger, Christopher K. et al., "Measurement and Imaging of Birefringence and Optic Axis Orientation by Phase Resolved Polarization Sensitive Optical Coherence Tomography," *Optics Express*, vol. 9, No. 13, Dec. 17, 2001, pp. 780-790.

Wang, Xuedong et al., (2001) "Propagation of Polarized Light in Birefringent Turbid Media: Time-Resolved Simulations," Optical Imaging Laboratory, Biomedical Engineering Program, Texas A&M University, Aug. 27, 2001, pp. 254-259.

Wong, Brian J.F. et al., "Optical Coherence Tomography of the Rat Cochlea," *Journal of Biomedical Optics*, vol. 5, No. 4, Oct. 2000, pp. 367-370.

Yao, Gang et al., "Propagation of Polarized Light in Turbid Media: Simulated Animation Sequences," *Optics Express*, vol. 7, No. 5, Aug. 28, 2000, pp. 198-203.

Wang, Xiao-Jun et al., "Characterization of Dentin and Enamel by Use of Optical Coherence Tomography," *Applied Optics*, vol. 38, No. 10, Apr. 1, 1999, pp. 2092-2096.

De Boer, Johannes F. et al., "Determination of the Depth-Resolved Stokes Parameters of Light Backscattered from Turbid Media by use of Polarization-Sensitive Optical Coherence Tomography," *Optics Letters*, vol. 24, No. 5, Mar. 1, 1999, pp. 300-302.

Ducros, Mathieu G. et al., "Polarization Sensitive Optical Coherence Tomography of the Rabbit Eye," *IEEE Journal of Selected Topics in Quantum Electronics*, vol. 5, No. 4, Jul./Aug. 1999, pp. 1159-1167.

Groner, Warren et al., "Orthogonal Polarization Spectral Imaging: A New Method for Study of the Microcirculation," *Nature Medicine Inc.*, vol. 5 No. 10, Oct. 1999, pp. 1209-1213.

De Boer, Johannes F. et al., "Polarization Effects in Optical Coherence Tomography of Various Viological Tissues," *IEEE Journal of Selected Topics in Quantum Electronics*, vol. 5, No. 4, Jul./Aug. 1999, pp. 1200-1204.

Yao, Gang et al., "Two-Dimensional Depth-Resolved Mueller Matrix Characterization of Biological Tissue by Optical Coherence Tomography," *Optics Letters*, Apr. 15, 1999, vol. 24, No. 8, pp. 537-539.

Lu, Shih-Yau et al., "Homogeneous and Inhomogeneous Jones Matrices," *J. Opt. Soc. Am. A.*, vol. 11, No. 2, Feb. 1994, pp. 766-773.

Bickel, S. William et al., "Stokes Vectors, Mueller Matrices, and Polarized Scattered Light," *Am. J. Phys.*, vol. 53, No. 5, May 1985 pp. 468-478.

Bréhonnet, F. Le Roy et al., "Optical Media and Target Characterization by Mueller Matrix Decomposition," *J. Phys. D: Appl. Phys.* 29, 1996, pp. 34-38.

Cameron, Brent D. et al., "Measurement and Calculation of the Two-Dimensional Backscattering Mueller Matrix of a Turbid Medium," *Optics Letters*, vol. 23, No. 7, Apr. 1, 1998, pp. 485-487.

De Boer, Johannes F. et al., "Two-Dimensional Birefringence Imaging in Biological Tissue by Polarization-Sensitive Optical Coherence Tomography," *Optics Letters*, vol. 22, No. 12, Jun. 15, 1997, pp. 934-936.

De Boer, Johannes F. et al., "Imaging Thermally Damaged Tissue by Polarization Sensitive Optical Coherence Tomography," *Optics Express*, vol. 3, No. 6, Sep. 14, 1998, pp. 212-218.

Everett, M.J. et al., "Birefringence Characterization of Biological Tissue by Use of Optical Coherence Tomography," *Optics Letters*, vol. 23, No. 3, Feb. 1, 1998, pp. 228-230.

Hee, Michael R. et al., "Polarization-Sensitive Low-Coherence Reflectometer for Birefringence Characterization and Ranging," *J. Opt. Soc. Am. B.*, vol. 9, No. 6, Jun. 1992, pp. 903-908.

Barakat, Richard, "Statistics of the Stokes Parameters," *J. Opt. Soc. Am. B.*, vol. 4, No. 7, Jul. 1987, pp. 1256-1263.

Schmitt, J.M. et al., "Cross-Polarized Backscatter in Optical Coherence Tomography of Biological Tissue," *Optics Letters*, vol. 23, No. 13, Jul. 1, 1998, pp. 1060-1062.

Schoenenberger, Klaus et al., "Mapping of Birefringence and Thermal Damage in Tissue by use of Polarization-Sensitive Optical Coherence Tomography," *Applied Optics*, vol. 37, No. 25, Sep. 1, 1998, pp. 6026-6036.

Pierce, Mark C. et al., "Simultaneous Intensity, Birefringence, and Flow Measurements with High-Speed Fiber-Based Optical Coherence Tomography," *Optics Letters*, vol. 27, No. 17, Sep. 1, 2002, pp. 1534-1536.

De Boer, Johannes F. et al., "Review of Polarization Sensitive Optical Coherence Tomography and Stokes Vector Determination," *Journal of Biomedical Optics*, Jul. 2002, vol. 7, No. 3, pp. 359-371.

Fried, Daniel et al., "Imaging Caries Lesions and Lesion Progression with Polarization Sensitive Optical Coherence Tomography," *Journal of Biomedical Optics*, vol. 7, No. 4, Oct. 2002, pp. 618-627.

Jiao, Shuliang et al., "Two-Dimensional Depth-Resolved Mueller Matrix of Biological Tissue Measured with Double-Beam Polarization-Sensitive Optical Coherence Tomography," *Optics Letters*, vol. 27, No. 2, Jan. 15, 2002, pp. 101-103.

Jiao, Shuliang et al., "Jones-Matrix Imaging of Biological Tissues with Quadruple-Channel Optical Coherence Tomography," *Journal of Biomedical Optics*, vol. 7, No. 3, Jul. 2002, pp. 350-358.

Kuranov, R.V. et al., "Complementary Use of Cross-Polarization and Standard OCT for Differential Diagnosis of Pathological Tissues," *Optics Express*, vol. 10, No. 15, Jul. 29, 2002, pp. 707-713.

Cense, Barry et al., "In Vivo Depth-Resolved Birefringence Measurements of the Human Retinal Nerve Fiber Layer by Polarization-Sensitive Optical Coherence Tomography," *Optics Letters*, vol. 27, No. 18, Sep. 15, 2002, pp. 1610-1612.

Ren, Hongwu et al., "Phase-Resolved Functional Optical Coherence Tomography: Simultaneous Imaging of In Situ Tissue Structure, Blood Flow Velocity, Standard Deviation, Birefringence, and Stokes Vectors in Human Skin," *Optics Letters*, vol. 27, No. 19, Oct. 1, 2002, pp. 1702-1704.

Tripathi, Renu et al., "Spectral Shaping for Non-Gaussian Source Spectra in Optical Coherence Tomography," *Optics Letters*, vol. 27, No. 6, Mar. 15, 2002, pp. 406-408.

Yasuno, Y. et al., "Birefringence Imaging of Human Skin by Polarization-Sensitive Spectral Interferometric Optical Coherence Tomography," *Optics Letters*, vol. 27, No. 20, Oct. 15, 2002 pp. 1803-1805.

White, Brian R. et al., "In Vivo Dynamic Human Retinal Blood Flow Imaging Using Ultra-High-Speed Spectral Domain Optical Doppler Tomography," *Optics Express*, vol. 11, No. 25, Dec. 15, 2003, pp. 3490-3497.

De Boer, Johannes F. et al., "Improved Signal-to-Noise Ratio in Spectral-Domain Compared with Time-Domain Optical Coherence Tomography," *Optics Letters*, vol. 28, No. 21, Nov. 1, 2003, pp. 2067-2069.

Jiao, Shuliang et al., "Optical-Fiber-Based Mueller Optical Coherence Tomography," *Optics Letters*, vol. 28, No. 14, Jul. 15, 2003, pp. 1206-1208.

Jiao, Shuliang et al., "Contrast Mechanisms In Polarization-Sensitive Mueller-Matrix Optical Coherence Tomography and Application in Burn Imaging," *Applied Optics*, vol. 42, No. 25, Sep. 1, 2003, pp. 5191-5197.

Moreau, Julien et al., "Full-Field Birefringence Imaging by Thermal-Light Polarization-Sensitive Optical Coherence Tomography. I. Theory," *Applied Optics*, vol. 42, No. 19, Jul. 1, 2003, pp. 3800-3810.

Moreau, Julien et al., "Full-Field Birefringence Imaging by Thermal-Light Polarization-Sensitive Optical Coherence Tomography. II. Instrument and Results," *Applied Optics*, vol. 42, No. 19, Jul. 1, 2003, pp. 3811-3818.

Morgan, Stephen P. et al., "Surface-Reflection Elimination in Polarization Imaging of Superficial Tissue," *Optics Letters*, vol. 28, No. 2, Jan. 15, 2003, pp. 114-116.

Oh, Jung-Taek et al., "Polarization-Sensitive Optical Coherence Tomography for Photoelasticity Testing of Glass/Epoxy Composites," *Optics Express*, vol. 11, No. 14, Jul. 14, 2003, pp. 1669-1676.

Park, B. Hyle et al., "Real-Time Multi-Functional Optical Coherence Tomography," *Optics Express*, vol. 11, No. 7, Apr. 7, 2003, pp. 782-793.

Shribak, Michael et al., "Techniques for Fast and Sensitive Measurements of Two-Dimensional Birefringence Distributions," *Applied Optics*, vol. 42, No. 16, Jun. 1, 2003, pp. 3009-3017.

Somervell, A.R.D. et al., "Direct Measurement of Fringe Amplitude and Phase Using a Heterodyne Interferometer Operating in Broadband Light," *Elsevier, Optics Communications*, Oct. 2003.

Stifter, D. et al., "Polarisation-Sensitive Optical Coherence Tomography for Material Characterisation and Strain-Field Mapping," Applied Physics A 76, Materials Science & Processing, Jan. 2003, pp. 947-951.

Davé, Digant P. et al., "Polarization-Maintaining Fiber-Based Optical Low-Coherence Reflectometer for Characterization and Ranging of Birefringence," *Optics Letters*, vol. 28, No. 19, Oct. 1, 2003, pp. 1775-1777.

Yang, Ying et al., "Observations of Birefringence in Tissues from Optic-Fibre-Based Optical Coherence Tomography," *Measurement Science and Technology*, Nov. 2002, pp. 41-46.

Yun, S.H. et al., "High-Speed Optical Frequency-Domain Imaging," *Optics Express*, vol. 11, No. 22, Nov. 3, 2003, pp. 2953-2963.

Yun, S.H. et al., "High-Speed Spectral-Domain Optical Coherence Tomography at 1.3 μm Wavelength," *Optics Express*, vol. 11, No. 26, Dec. 29, 2003, pp. 3598-3604.

Zhang, Jun et al., "Determination of Birefringence and Absolute Optic Axis Orientation Using Polarization-Sensitive Optical Coherence Tomography with PM Fibers," *Optics Express*, vol. 11, No. 24, Dec. 1, 2003, pp. 3262-3270.

Pircher, Michael et al., "Three Dimensional Polarization Sensitive OCT of Human Skin In Vivo," 2004, *Optical Society of America*.

Götzinger, Erich et al., "Measurement and Imaging of Birefringent Properties of the Human Cornea with Phase-Resolved, Polarization-Sensitive Optical Coherence Tomography," *Journal of Biomedical Optics*, vol. 9, No. 1, Jan./Feb. 2004, pp. 94-102.

Guo, Shuguang et al., "Depth-Resolved Birefringence and Differential Optical Axis Orientation Measurements with Finer-based Polarization-Sensitive Optical Coherence Tomography," *Optics Letters*, vol. 29, No. 17, Sep. 1, 2004, pp. 2025-2027.

Huang, Xiang-Run et al.,"Variation of Peripapillary Retinal Nerve Fiber Layer Birefringence in Normal Human Subjects," *Investigative Ophthalmology & Visual Science*, vol. 45, No. 9, Sep. 2004, pp. 3073-3080.

Matcher, Stephen J. et al., "The Collagen Structure of Bovine Intervertebral Disc Studied Using Polarization-Sensitive Optical Coherence Tomography," *Physics in Medicine and Biology*, 2004, pp. 1295-1306.

Nassif, Nader et al., "In Vivo Human Retinal Imaging by Ultrahigh-Speed Spectral Domain Optical Coherence Tomography," *Optics Letters*, vol. 29, No. 5, Mar. 1, 2004, pp. 480-482.

Nassif, N.A. et al., "In Vivo High-Resolution Video-Rate Spectral-Domain Optical Coherence Tomography of the Human Retina and Optic Nerve," *Optics Express*, vol. 12, No. 3, Feb. 9, 2004, pp. 367-376.

Park, B. Hyle et al., Comment on "Optical-Fiber-Based Mueller Optical Coherence Tomography," *Optics Letters*, vol. 29, No. 24, Dec. 15, 2004, pp. 2873-2874.

Park, B. Hyle et al., "Jones Matrix Analysis for a Polarization-Sensitive Optical Coherence Tomography System Using Fiber-Optic Components," *Optics Letters*, vol. 29, No. 21, Nov. 1, 2004, pp. 2512-2514.

Pierce, Mark C. et al., "Collagen Denaturation can be Quantified in Burned Human Skin Using Polarization-Sensitive Optical Coherence Tomography," *Elsevier, Burns*, 2004, pp. 511-517.

Pierce, Mark C. et al., "Advances in Optical Coherence Tomography Imaging for Dermatology," *The Society for Investigative Dermatology, Inc.* 2004, pp. 458-463.

Pierce, Mark C. et al., "Birefringence Measurements in Human Skin Using Polarization-Sensitive Optical Coherence Tomography," *Journal of Biomedical Optics*, vol. 9, No. 2, Mar./Apr. 2004, pp. 287-291.

Cense, Barry et al., "In Vivo Birefringence and Thickness Measurements of the Human Retinal Nerve Fiber Layer Using Polarization-Sensitive Optical Coherence Tomography," *Journal of Biomedical Optics*, vol. 9, No. 1, Jan./Feb. 2004, pp. 121-125.

Pircher, Michael et al., "Imaging of Polarization Properties of Human Retina in Vivo with Phase Resolved Transversal PS-OCT," *Optics Express*, vol. 12, No. 24, Nov. 29, 2004 pp. 5940-5951.

Pircher, Michael et al., "Transversal Phase Resolved Polarization Sensitive Optical Coherence Tomography," *Physics in Medicine & Biology*, 2004, pp. 1257-1263.

Srinivas, Shyam M. et al., "Determination of Burn Depth by Polarization-Sensitive Optical Coherence Tomography," *Journal of Biomedical Optics*, vol. 9, No. 1, Jan./Feb. 2004, pp. 207-212.

Strasswimmer, John et al., "Polarization-Sensitive Optical Coherence Tomography of Invasive Basal Cell Carcinoma," *Journal of Biomedical Optics*, vol. 9, No. 2, Mar./Apr. 2004, pp. 292-298.

Todorovič, Miloš et al., "Determination of Local Polarization Properties of Biological Samples in the Presence of Diattenuation by use of Mueller Optical Coherence Tomography," *Optics Letters*, vol. 29, No. 20, Oct. 15, 2004, pp. 2402-2404.

Yasuno, Yoshiaki et al., "Polarization-Sensitive Complex Fourier Domain Optical Coherence Tomography for Jones Matrix Imaging of Biological Samples," Applied Physics Letters, vol. 85, No. 15, Oct. 11, 2004, pp. 3023-3025.

Acioli, L. H., M. Ulman, et al. (1991). "Femtosecond Temporal Encoding in Barium-Titanate." *Optics Letters* 16(24): 1984-1986.

Aigouy, L., A. Lahrech, et al. (1999). "Polarization effects in apertureless scanning near-field optical microscopy: an experimental study." *Optics Letters* 24(4): 187-189.

Akiba, M., K. P. Chan, et al. (2003). "Full-field optical coherence tomography by two-dimensional heterodyne detection with a pair of CCD camers." *Optics Letters* 28(10): 816-818.

Akkin, T., D. P. Dave, et al. (2004). "Detection of neural activity using phase-sensitive optical low-coherence reflectometry." *Optics Express* 12(11): 2377-2386.

Akkin, T., D. P. Dave, et al. (2003). "Surface analysis using phase sensitive optical low coherence reflectometry." *Lasers in Surgery and Medicine*: 4-4.

Akkin, T., D. P. Dave, et al. (2003). "Imaging tissue response to electrical and photothermal stimulation with nanometer sensitivity." *Lasers in Surgery and Medicine* 33(4): 219-225.

Akkin, T., T. E. Milner, et al. (2002). "Phase-sensitive measurement of birefringence change as an indication of neural functionality and diseases." *Lasers in Surgery and Medicine*: 6-6.

Andretzky, P., Lindner, M.W., Herrmann, J.M., Schultz, A., Konzog, M., Kiesewetter, F., Haeusler, G. (1999). "Optical coherence tomography by 'spectral radar': Dynamic range estimation and in vivo measurements of skin." *Proceedings of SPIE—The International Society for Optical Engineering* 3567: pp. 78-87.

Antcliff, R. J., T. J. ffytche, et al. (2000). "Optical coherence tomography of melanocytoma." *American Journal of Ophthalmology* 130(6): 845-7.

Antcliff, R. J., M. R. Stanford, et al. (2000). "Comparison between optical coherence tomography and fundus fluorescein angiography for the detection of cystoid macular edema in patients with uveitis." *Ophthalmology* 107(3): 593-9.

Anvari, B., T. E. Milner, et al. (1995). "Selective Cooling of Biological Tissues—Application for Thermally Mediated Therapeutic Procedures." *Physics in Medicine and Biology* 40(2): 241-252.

Anvari, B., B. S. Tanenbaum, et al. (1995). "A Theoretical-Study of the Thermal Response of Skin to Cryogen Spray Cooling and Pulsed-Laser Irradiation—Implications for Treatment of Port-Wine Stain Birthmarks." *Physics in Medicine and Biology* 40(9): 1451-1465.

Arend, O., M. Ruffer, et al. (2000). "Macular circulation in patients with diabetes mellitus with and without arterial hypertension." *British Journal of Ophthalmology* 84(12): 1392-1396.

Arimoto, H. and Y. Ohtsuka (1997). "Measurements of the complex degree of spectral coherence by use of a wave-front-folded interferometer." *Optics Letters* 22(13): 958-960.

Azzolini, C., F. Patelli, et al. (2001). "Correlation between optical coherence tomography data and biomicroscopic interpretation of idiopathic macular hole." *American Journal of Ophthalmology* 132(3): 348-55.

Baba, T., K. Ohno-Matsui, et al. (2002). "Optical coherence tomography of choroidal neovascularization in high myopia." *Acta Ophthalmoloqica Scandinavica* 80(1): 82-7.

Bail, M. A. H., Gerd; Herrmann, Juergen M.; Lindner, Michael W.; Ringler, R. (1996). "Optical coherence tomography with the "spectral radar": fast optical analysis in volume scatterers by short-coherence interferometry." *Proc. SPIE*, 2925: p. 298-303.

Baney, D. M. and W. V. Sorin (1993). "Extended-Range Optical Low-Coherence Reflectometry Using a Recirculating Delay Technique." *Ieee Photonics Technology Letters* 5(9): 1109-1112.

Baney, D. M., B. Szafraniec, et al. (2002). "Coherent optical spectrum analyzer." *Ieee Photonics Technology Letters* 14(3): 355-357.

Barakat, R. (1981). "Bilinear Constraints between Elements of the 4by4 Mueller-Jones Transfer-Matrix of Polarization Theory." *Optics Communications* 38(3): 159-161.

Barakat, R. (1993). "Analytic Proofs of the Arago-Fresnel Laws for the Interference of Polarized-Light." *Journal of the Optical Society of America a-Optics Image Science and Vision* 10(1): 180-185.

Barbastathis, G. and D. J. Brady (1999). "Multidimensional tomographic imaging using volume holography." *Proceedings of the Ieee* 87(12): 2098-2120.

Bardal, S., A. Kamal, et al. (1992). "Photoinduced Birefringence in Optical Fibers—a Comparative-Study of Low-Birefringence and High-Birefringence Fibers." *Optics Letters* 17(6): 411-413.

Barsky, S. H., S. Rosen, et al. (1980). "Nature and Evolution of Port Wine Stains—Computer-Assisted Study." *Journal of Investigative Dermatology* 74(3): 154-157.

Barton, J. K., J. A. Izatt, et al. (1999). "Three-dimensional reconstruction of blood vessels from in vivo color Doppler optical coherence tomography images." *Dermatology* 198(4): 355-361.

Barton, J. K., A. Rollins, et al. (2001). "Photothermal coagulation of blood vessels: A comparison of high-speed optical coherence tomography and numerical modelling." *Physics in Medicine and Biology* 46.

Barton, J. K., A. J. Welch, et al. (1998). "Investigating pulsed dye laser-blood vessel interaction with color Doppler optical coherence tomography." *Optics Express* 3.

Bashkansky, M., M. D. Duncan, et al. (1997). "Subsurface defect detection in ceramics by high-speed high-resolution optical coherent tomography." *Optics Letters* 22 (1): 61-63.

Bashkansky, M. and J. Reintjes (2000). "Statistics and reduction of speckle in optical coherence tomography." *Optics Letters* 25(8): 545-547.

Baumgartner, A., S. Dichtl, et al. (2000). "Polarization-sensitive optical coherence tomography of dental structures." *Caries Research* 34(1): 59-69.

Baumgartner, A., C. K. Hitzenberger, et al. (2000). "Resolution-improved dual-beam and standard optical coherence tomography: a comparison." *Graefes Archive for Clinical and Experimental Ophthalmology* 238(5): 385-392.

Baumgartner, A., C. K. Hitzenberger, et al. (1998). "Signal and resolution enhancements in dual beam optical coherence tomography of the human eye." *Journal of Biomedical Optics* 3(1): 45-54.

Beaurepaire, E., P. Gleyzes, et at. (1998). *Optical coherence microscopy for the in-depth study of biological structures: System based on a parallel detection scheme*, Proceedings of SPIE—The International Society for Optical Engineering.

Beaurepaire, E., L. Moreaux, et al. (1999). "Combined scanning optical coherence and two-photon-excited fluorescence microscopy." *Optics Letters* 24(14): 969-971.

Bechara, F. G., T. Gambichler, et al. (2004). "Histomorphologic correlation with routine histology and optical coherence tomography." *Skin Research and Technology* 10 (3): 169-173.

Bechmann, M., M. J. Thiel, et al. (2000). "Central corneal thickness determined with optical coherence tomography in various types of glaucoma. [see comments]." *British Journal of Ophthalmology* 84(11): 1233-7.

Bek, T. and M. Kandi (2000). "Quantitative anomaloscopy and optical coherence tomography scanning in central serous chorioretinopathy." *Acta Ophthalmologica Scandinavica* 78(6): 632-7.

Benoit, A. M., K. Naoun, et al. (2001). "Linear dichroism of the retinal nerve fiber layer expressed with Mueller matrices." *Applied Optics* 40(4): 565-569.

Bicout, D., C. Brosseau, et al. (1994). "Depolarization of Multiply Scattered Waves by Spherical Diffusers—Influence of the Size Parameter." *Physical Review* E 49(2): 1767-1770.

Blanchot, L., M. Lebec, et al. (1997). *Low-coherence in depth microscopy for biological tissues imaging: Design of a real time control system*. Proceedings of SPIE—The International Society for Optical Engineering.

Blumenthal, E. Z. and R. N. Weinreb (2001). "Assessment of the retinal nerve fiber layer in clinical trials of glaucoma neuroprotection. [Review] [36 refs]." *Survey of Ophthalmology* 45(Suppl 3): S305-12; discussion S332-4.

Blumenthal, E. Z., J. M. Williams, et al. (2000). "Reproducibility of nerve fiber layer thickness measurements by use of optical coherence tomography." *Ophthalmology* 107(12): 2278-82.

Boppart, S. A., B. E. Bouma, et al. (1996). "Imaging developing neural morphology using optical coherence tomography." *Journal of Neuroscience Methods* 70.

Boppart, S. A., B. E. Bouma, et al. (1997). "Forward-imaging instruments for optical coherence tomography." *Optics Letters* 22.

Boppart, S. A., B. E. Bouma, et al. (1998). "Intraoperative assessment of microsurgery with three-dimensional optical coherence tomography." *Radiology* 208: 81-86.

Boppart, S. A., J. Herrmann, et al. (1999). "High-resolution optical coherence tomography-guided laser ablation of surgical tissue." *Journal of Surgical Research* 82(2): 275-84.

Bouma, B. E. and J. G. Fujimoto (1996). "Compact Kerr-lens mode-locked resonators." *Optics Letters* 21. 134-136.

Bouma, B. E., L. E. Nelson, et al. (1998). "Optical coherence tomographic imaging of human tissue at 1.55 mu m and 1.81 mu m using Er and Tm-doped fiber sources." *Journal of Biomedical Optics* 3. 76-79.

Bouma, B. E., M. Ramaswamy-Paye, et al. (1997). "Compact resonator designs for mode-locked solid-state lasers." *Applied Physics B (Lasers and Optics)* B65. 213-220.

Bouma, B. E. and G. J. Tearney (2002). "Clinical imaging with optical coherence tomography." *Academic Radiology* 9(8): 942-953.

Bouma, B. E., G. J. Tearney, et al. (1996). "Self-phase-modulated Kerr-lens mode-locked Cr:forsterite laser source for optical coherence tomography." *Optics Letters* 21(22): 1839.

Bouma, B. E., G. J. Tearney, et al. (2000). "High-resolution imaging of the human esophagus and stomach in vivo using optical coherence tomography." *Gastrointestinal Endoscopy* 51(4): 467-474.

Bouma, B. E., G. J. Tearney, et al. (2003). "Evaluation of intracoronary stenting by intravascular optical coherence tomography." *Hear* 89(3): 317-320.

Bourquin, S., V. Monterosso, et al. (2000). "Video-rate optical low-coherence reflectometry based on a linear smart detector array." *Optics Letters* 25(2): 102-104.

Bourquin, S., P. Seitz, et al. (2001). "Optical coherence topography based on a two-dimensional smart detector array." *Optics Letters* 26(8): 512-514.

Bouzid, A., M. A. G. Abushagur, et al. "Fiber-optic four-detector polarimeter." *Optics Communications* 118(3-4): 329-334.

Bowd, C., R. N. Weinreb, et al. (2000). "The retinal nerve fiber layer thickness in ocular hypertensive, normal, and glaucomatous eyes with optical coherence tomography." *Archives of Ophthalmology* 118(1): 22-6.

Bowd, C., L. M. Zangwill, et al. (2001). "Detecting early glaucoma by assessment of retinal nerve fiber layer thickness and visual fuction." *Investigative Ophthalmology & Visual Science* 42(9): 1993-2003.

Bowd, C., L. M. Zangwill, et al. (2002). "Imaging of the optic disc and retinal nerve fiber layer: the effects of age, optic disc area, refractive error, and gender." *Journal of the Optical Society of America, A, Optics, Image Science, & Vision* 19(1): 197-207.

Brand, S., J. M. Poneros, et al. (2000). "Optical coherence tomography in the gastrointestinal tract." *Endoscopy* 32(10): 796-803.

Brezinski, M. E. and J. G. Fujimoto (1999). "Optical coherence tomography: high-resolution imaging in nontransparent tissue." *IEEE Journal of Selected Topics in Quantum Electronics* 5(4): 1185-1192.

Brezinski, M. E., G. J. Tearney, et al. (1996). "Imaging of coronary artery microstructure (in vitro) with optical coherence tomography." *American Journal of Cardiology* 77 (1): 92-93.

Brezinski, M. E., G. J. Tearney, et al. (1996). "Optical coherence tomography for optical biopsy—Properties and demonstration of vascular pathology." *Circulation* 93(6): 1206-1213.

Brezinski, M. E., G. J. Tearney, et al. (1997). "Assessing atherosclerotic plaque morphology: Comparison of optical coherence tomography and high frequency intravascular ultrasound." *Heart* 77(5): 397-403.

Brink, H. B. K. and G. J. Vanblokland (1988). "Birefringence of the Human Foveal Area Assessed Invivo with Mueller-Matrix Ellipsometry." *Journal of the Optical Society of America a-Optics Image Science and Vision* 5(1): 49-57.

Brosseau, C. and D. Bicout (1994). "Entropy Production in Multiple-Scattering of Light by a Spatially Random Medium." *Physical Review E* 50(6): 4997-5005.

Burgoyne, C. F., D. E. Mercante, et al. (2002). "Change detection in regional and volumetric disc parameters using longitudinal confocal scanning laser tomography." *Ophthalmology* 109(3): 455-66.

Candido, R. and T. J. Allen (2002). "Haemodynamics in microvascular complications in type 1 diabetes." *Diabetes-Metabolism Research and Reviews* 18(4): 286-304.

Cense, B., T. C. Chen, et al. (2004). "Thickness and birefringence of healthy retinal nerve fiber layer tissue measured with polarization-sensitive optical coherence tomography." *Investigative Ophthalmology & Visual Science* 45(8): 2606-2612.

Cense, B., N. Nassif, et al. (2004). "Ultrahigh-Resolution High-speed Retinal Imaging Using Spectral-Domain Optical Coherence Tomography." *Optics Express* 12(11): 2435-2447.

Chance, B., J. S. Leigh, et al. (1988). "Comparison of Time-Resolved and Time-Unresolved Measurements of Deoxyhemoglobin in Brain." *Proceedings of the National Academy of Sciences of the United States of America* 85(14): 4971-4975.

Chang, E. P., D. A. Keedy, et al. (1974). "Ultrastructures of Rabbit Corneal Stroma—Mapping of Optical and Morphological Anisotropies." *Biochimica Et Biophysica Acta* 343(3): 615-626.

Chartier, T., A. Hideur, et al. (2001). "Measurement of the elliptical birefringence of single-mode optical fibers." *Applied Optics* 40(30): 5343-5353.

Chauhan, B. C., J. W. Blanchard, et al. (2000). "Technique for Detecting Serial Topographic Changes in the Optics Disc and Peripapillary Retina Using Scanning Laser Tomograph." *Invest Ophthalmol Vis Sci* 41: 775-782.

Chen, Z. P., T. E. Milner, et al. (1997). "Optical Doppler tomographic imaging of fluid flow velocity in highly scattering media." *Optics Letters* 22(1): 64-66.

Chen, Z. P., T. E. Milner, et al. (1997). "Noninvasive imaging of in vivo blood flow velocity using optical Doppler tomography." *Optics Letters* 22(14): 1119-1121.

Chen, Z. P., Y. H. Zhao, et al. (1999). "Optical Doppler tomography." *Ieee Journal of Selected Topics in Quantum Electronics* 5(4): 1134-1142.

Cheong, W. F., S. A. Prahl, et al. (1990). "A Review of the Optical-Properties of Biological Tissues." *Ieee Journal of Quantum Electronics* 26(12): 2166-2185.

Chernikov, S. V., Y. Zhu, et al. (1997). "Supercontinuum self-Q-switched ytterbium fiber laser." *Optics Letters* 22(5): 298-300.

Cho, S. H., B. E. Bouma, et al. (1999). "Low-repetition-rate high-peak-power Kerr-lens mode-locked TiP:Al/sub 2/0/sub 3/ laser with a multiple-pass cavity." *Optics Letters* 24(6): 417-419.

Choma, M. A., M. V. Sarunic, et al. (2003). "Sensitivity advantage of swept source and Fourier domain optical coherence tomography." *Optics Express* 11(18): 2183-2189.

Choma, M. A., C. H. Yang, et al. (2003). "Instantaneous quadrature low-coherence interferometry with 3×3 fiber-optic couplers." *Optics Letters* 28(22): 2162-2164.

Choplin, N. T. and D. C. Lundy (2001). "The sensitivity and specificity of scanning laser polarimetry in the detection of glaucoma in a clinical setting." *Ophthalmology* 108 (5): 899-904.

Christens Barry, W. A., W. J. Green, et al. (1996). "Spatial mapping of polarized light transmission in the central rabbit cornea." *Experimental Eye Research* 62(6): 651-662.

Chvapil, M., D. P. Speer, et al. (1984). "Identification of the depth of burn injury by collagen stainability." *Plastic & Reconstructive Surgery* 73(3): 438-41.

Cioffi, G. A. (2001). "Three common assumptions about ocular blood flow and glaucoma." *Survey of Ophthalmology* 45: S325-S331.

Coleman, A. L. (1999). "Glaucoma." *Lancet* 354(9192): 1803-10.

Collaborative Normal-Tension Glaucoma Study Group (1998). "Comparison of Glaucomatous Progression Between Untreated Patients With Normal Tension Glaucoma and Patients with Therapeutically Reduced Intraocular Pressures." *Am J Ophthalmol* 126: 487-97.

Collaborative Normal-Tension Glaucoma Study Group (1998). "The effectiveness of intraocular pressure reduction in the treatment of normal-tension glaucoma." *Am J Ophthalmol* 126: 498-505.

Collaborative Normal-Tension Glaucoma Study Group (2001). "Natural History of Normal-Tension Glaucoma." *Ophthalmology* 108: 247-253.

Colston, B. W., M. J. Everett, et al. (1998). "Imaging of hard- and soft-tissue structure in the oral cavity by optical coherence tomography." *Applied Optics* 37(16): 3582-3585.

Colston, B. W., U. S. Sathyam, et al. (1998). "Dental OCT." *Optics Express* 3(6): 230-238.

Congdon, N. G., D. S. Friedman, et al. (2003). "Important causes of visual impairment in the world today." *Jama-Journal of the American Medical Association* 290(15): 2057-2060.

Cregan, R. F., B. J. Mangan, et al. (1999). "Single-mode photonic band gap guidance of light in air." *Science* 285(5433): 1537-1539.

DalMolin, M., A. Galtarossa, et al. (1997). "Experimental investigation of linear polarization in high-birefringence single-mode fibers." *Applied Optics* 36(12): 2526-2528.

Danielson, B. L. and C. D. Whittenberg (1987). "Guided-Wave Reflectometry with Micrometer Resolution." *Applied Optics* 26(14): 2836-2842.

Dave, D. P. and T. E. Milner (2000). "Doppler-angle measurement in highly scattering media." *Optics Letters* 25(2): 1523-1525.

de Boer, J. F., T. E. Milner, et al. (1998). *Two dimensional birefringence imaging in biological tissue using phase and polarization sensitive optical coherence tomography*. Trends in Optics and Photonics (TOPS): Advances in Optical Imaging and Photon Migration, Orlando, USA, Optical Society of America, Washington, DC 1998.

de Boer, J. F., C. E. Saxer, et al. (2001). "Stable carrier generation and phase-resolved digital data processing in optical coherence tomography." *Applied Optics* 40(31): 5787-5790.

Degroot, P. and L. Deck (1993). "3-Dimensional Imaging by Sub-Nyquist Sampling of White-Light Interferograms." *Optics Letters* 18(17): 1462-1464.

Denk, W., J. H. Strickler, et al. (1990). "2-Photon Laser Scanning Fluorescence Microscopy." *Science* 248(4951): 73-76.

Descour, M. R., A. H. O. Karkkainen, et al. (2002). "Toward the development of miniaturized Imaging systems for detection of pre-cancer." *Ieee Journal of Quantum Electronics* 38(2): 122-130.

Dettwiller, L. (1997). "Polarization state interference: A general investigation." *Pure and Applied Optics* 6(1): 41-53.

DiCarlo, C. D., W. P. Roach, et al. (1999). "Comparison of optical coherence tomography imaging of cataracts with histopathology." *Journal of Biomedical Optics* 4.

Ding, Z., Y. Zhao, et al. (2002). "Real-time phase-resolved optical coherence tomography and optical Doppler tomography." *Optics Express* 10(5): 236-245.

Dobrin, P. B. (1996). "Effect of histologic preparation on the cross-sectional area of arterial rings." *Journal of Surgical Research* 61(2): 413-5.

Donohue, D. J., B. J. Stoyanov, et al. (1995). "Numerical Modeling of the Corneas Lamellar Structure and Birefringence Properties." *Journal of the Optical Society of America a-Optics Image Science and Vision* 12(7): 1425-1438.

Doornbos, R. M. P., R. Lang, et al. (1999). "The determination of in vivo human tissue optical properties and absolute chromophore concentrations using spatially resolved steady-state diffuse reflectance spectroscopy." *Physics in Medicine and Biology* 44(4): 967-981.

Drexler, W., A. Baumgartner, et al. (1997). "Biometric investigation of changes in the anterior eye segment during accommodation." *Vision Research* 37(19): 2789-2800.

Drexler, W., A. Baumgartner, et al. (1997). "Submicrometer precision biometry of the anterior segment of the human eye." *Investigative Ophthalmology & Visual Science* 38(7): 1304-1313.

Drexler, W., A. Baumgartner, et al. (1998). "Dual beam optical coherence tomography: signal identification for ophthalmologic diagnosis." *Journal of Biomedical Optics* 3 (1): 55-65.

Drexler, W., O. Findl, et al. (1998). "Partial coherence interferometry: A novel approach to biometry in cataract surgery." *American Journal of Ophthalmology* 126(4): 524-534.

Drexler, W., O. Findl, et al. (1997). "Clinical feasibility of dual beam optical coherence topography and tomography for ophthalmologic diagnosis." *Investigative Ophthalmology & Visual Science* 38(4): 1038-1038.

Drexler, W., C. K. Hitzenberger, et al. (1998). "Investigation of dispersion effects in ocular media by multiple wavelength partial coherence interferometry." *Experimental Eye Research* 66(1): 25-33.

Drexler, W., C. K. Hitzenberger, et al. (1996). "(Sub)micrometer precision biometry of the human eye by optical coherence tomography and topography." *Investigative Ophthalmology & Visual Science* 37(3): 4374-4374.

Drexler, W., C. K. Hitzenberger, et al. (1995). "Measurement of the Thickness of Fundus Layers by Partial Coherence Tomography." *Optical Engineering* 34(3): 701-710.

Drexler, W., U. Morgner, et al. (2001). "Ultrahigh-resolution ophthalmic optical coherence tomography." *Nature Medicine* 7(4): 502-507.

Drexler, W., U. Morgner, et al. (2001). "Ultrahigh-resolution ophthalmic optical coherence tomography. [erratum appears in Nat Med May 2001;7(5):636.]." *Nature Medicine* 7(4): 502-7.

Drexler, W., H. Sattmann, et al. (2003). "Enhanced visualization of macular pathology with the use of ultrahigh-resolution optical coherence tomography." *Archives of Ophthalmology* 121(5): 695-706.

Drexler, W., D. Stamper, et al. (2001). "Correlation of collagen organization with polarization sensitive imaging of in vitro cartilage: implications for osteoarthritis." *Journal of Rheumatology* 28(6): 1311-8.

Droog, E. J., W. Steenbergen, et al. (2001). "Measurement of depth of burns by laser Doppler perfusion imaging." *Burns* 27(6): 561-8.

Dubois, A., K. Grieve, et al. (2004). "Ultrahigh-resolution full-field optical coherence tomography." *Applied Optics* 43(14): 2874-2883.

Dubois, A., L. Vabre, et al. (2002). "High-resolution full-field optical coherence tomography with a Linnik microscope." *Applied Optics* 41(4): 805-812.

Ducros, M., M. Laubscher, et al. (2002). "Parallel optical coherence tomography in scattering samples using a two-dimensional smart-pixel detector array." *Optics Communications* 202(1-3): 29-35.

Ducros, M. G., J. D. Marsack, et al. (2001). "Primate retina imaging with polarization-sensitive optical coherence tomography." *Journal of the Optical Society of America a-Optics Image Science and Vision* 18(12): 2945-2956.

Duncan, A., J. H. Meek, et al. (1995). "Optical Pathlength Measurements on Adult Head, Calf and Forearm and the Head of the Newborn-Infant Using Phase-Resolved Optical Spectroscopy." *Physics in Medicine and Biology* 40(2): 295-304.

Eigensee, A., G. Haeusler, et al. (1996). "New method of short-coherence interferometry in human skin (in vivo) and in solid volume scatterers." *Proceedings of SPIE—The International Society for Optical Engineering* 2925: 169-178.

Eisenbeiss, W., J. Marotz, et al. (1999). "Reflection-optical multispectral imaging method for objective determination of burn depth." *Burns* 25(8): 697-704.

Elbaum, M., M. King, et al. (1972). "Wavelength-Diversity Technique for Reduction of Speckle Size." *Journal of the Optical Society of America* 62(5): 732-&.

Ervin, J. C., H. G. Lemij, et al. (2002). "Clinician change detection viewing longitudinal stereophotographs compared to confocal scanning laser tomography in the LSU Experimental Glaucoma (LEG) Study." *Ophthalmology* 109(3): 467-81.

Essenpreis, M., C. E. Elwell, et al. (1993). "Spectral Dependence of Temporal Point Spread Functions in Human Tissues." *Applied Optics* 32(4): 418-425.

Eun, H. C. (1995). "Evaluation of skin blood flow by laser Doppler flowmetry. [Review] [151 refs]." *Clinics in Dermatology* 13(4): 337-47.

Evans, J. A., J. M. Poneros, et al. (2004). "Application of a histopathologic scoring system to optical coherence tomography (OCT) images to identify high-grade dysplasia in Barrett's esophagus." *Gastroenterology* 126(4): A51-A51.

Feldchtein, F. I., G. V. Gelikonov, et al. (1998). "In vivo OCT imaging of hard and soft tissue of the oral cavity." *Optics Express* 3(6): 239-250.

Feldchtein, F. I., G. V. Gelikonov, et al. (1998). "Endoscopic applications of optical coherence tomography." *Optics Express* 3(6): 257-270.

Fercher, A. F., W. Drexler, et al. (1997). "Optical ocular tomography." *Neuro-Ophthalmology* 18(2): 39-49.

Fercher, A. F., W. Drexler, et al. (1994). *Measurement of optical distances by optical spectrum modulation.* Proceedings of SPIE—The International Society for Optical Engineering.

Fercher, A. F., W. Drexler, et al. (2003). "Optical coherence tomography—principles and applications." *Reports on Progress in Physics* 66(2): 239-303.

Fercher, A. F., C. Hitzenberger, et al. (1991). "Measurement of Intraocular Optical Distances Using Partially Coherent Laser-Light." *Journal of Modern Optics* 38(7): 1327-1333.

Fercher, A. F., C. K. Hitzenberger, et al. (1996). *Ocular partial coherence interferometry.* Proceedings of SPIE—The International Society for Optical Engineering.

Fercher, A. F., C. K. Hitzenberger, et al. (1993). "In-Vivo Optical Coherence Tomography." *American Journal of Ophthalmology* 116(1): 113-115.

Fercher, A. F., C. K. Hitzenberger, et al. (1994). *In-vivo dual-beam optical coherence tomography.* Proceedings of SPIE—The International Society for Optical Engineering.

Fercher, A. F., C. K. Hitzenberger, et al. (1995). "Measurement of Intraocular Distances by Backscattering Spectral Interferometry." *Optics Communications* 117(1-2): 43-48.

Fercher, A. F., C. K. Hitzenberger, et al. (2000). "A thermal light source technique for optical coherence tomography." *Optics Communications* 185(1-3): 57-64.

Fercher, A. F., C. K. Hitzenberger, et al. (2001). "Numerical dispersion compensation for Partial Coherence Interferometry and Optical Coherence Tomography." *Optics Express* 9(12): 610-615.

Fercher, A. F., C. K. Hitzenberger, et al. (2002). "Dispersion compensation for optical coherence tomography depth—scan signals by a numerical technique." *Optics Communications* 204(1-6): 67-74.

Fercher, A. F., H. C. Li, et al. (1993). "Slit Lamp Laser-Doppler Interferometer." *Lasers in Surgery and Medicine* 13(4): 447-452.

Fercher, A. F., K. Mengedoht, et at. (1988). "Eye-Length Measurement by Interferometry with Partially Coherent-Light." *Optics Letters* 13(3): 186-188.

Ferro, P., M. Haelterman, et al. (1991). "All-Optical Polarization Switch with Long Low-Birefringence Fiber." *Electronics Letters* 27(16): 1407-1408.

Fetterman, M. R., D. Goswami, et al. (1998). "Ultrafast pulse shaping: amplification and characterization." *Optics Express* 3(10): 366-375.

Findl, O., W. Drexler, et al. (2001). "Improved prediction of intraocular lens power using partial coherence interferometry." *Journal of Cataract and Refractive Surgery* 27 (6): 861-867.

Fork, R. L., C. H. B. Cruz, et al. (1987). "Compression of Optical Pulses to 6 Femtoseconds by Using Cubic Phase Compensation." *Optics Letters* 12(7): 483-485.

Foschini, G. J. and C. D. Poole (1991). "Statistical-Theory of Polarization Dispersion in Single-Mode Fibers." *Journal of Lightwave Technology* 9(11): 1439-1456.

Francia, C., F. Bruyere, et al. (1998). "PMD second-order effects on pulse propagation in single-mode optical fibers." *Ieee Photonics Technology Letters* 10(12): 1739-1741.

Fried, D., R. E. Glena, et al. (1995). "Nature of Light-Scattering in Dental Enamel and Dentin at Visible and near-Infrared Wavelengths." *Applied Optics* 34(7): 1278-1285.

Fujimoto, J. G., M. E. Brezinski, et al. (1995). "Optical Biopsy and Imaging Using Optical Coherence Tomography." *Nature Medicine* 1(9): 970-972.

Fukasawa, A. and H. Iijima (2002). "Optical coherence tomography of choroidal osteoma." *American Journal of Ophthalmology* 133(3): 419-21.

Fymat, A. L. (1981). "High-Resolution Interferometric Spectrophotopolarimetry." *Optical Engineering* 20(1): 25-30.

Galtarossa, A., L. Palmieri, et al. (2000). "Statistical characterization of fiber random birefringence." *Optics Letters* 25(18): 1322-1324.

Galtarossa, A., L. Palmieri, et al. (2000). "Measurements of beat length and perturbation length in long single-mode fibers." *Optics Letters* 25(6): 384-386.

Gandjbakhche, A. H., P. Mills, et al. (1994). "Light-Scattering Technique for the Study of Orientation and Deformation of Red-Blood-Cells in a Concentrated Suspension." *Applied Optics* 33(6): 1070-1078.

Garcia, N. and M. Nieto-Vesperinas (2002). "Left-handed materials do not make a perfect lens." *Physical Review Letters* 88(20).

Gelikonov, V. M., G. V. Gelikonov, et al. (1995). "Coherent Optical Tomography of Microscopic Inhomogeneities in Biological tissues." *Jetp Letters* 61(2): 158-162.

George, N. and A. Jain (1973). "Speckle Reduction Using Multiple Tones of Illumination." *Applied Optics* 12(6): 1202-1212.

Gibson, G. N., R. Klank, et al. (1996). "Electro-optically cavity-dumped ultrashort-pulse Ti:sapphire oscillator." *Optics Letters* 21(14): 1055.

Gil, J. J. (2000). "Characteristic properties of Mueller matrices." *Journal of the Optical Society of America a-Optics Image Science and Vision* 17(2): 328-334.

Gil, J. J. and E. Bernabeu (1987). "Obtainment of the Polarizing and Retardation Parameters of a Nondepolarizing Optical-System from the Polar Decomposition of Its Mueller Matrix." *Optik* 76(2): 67-71.

Gladkova, N. D., G. A. Petrova, et al. (2000). "In vivo optical coherence tomography imaging of human skin: norm and pathology." *Skin Research and Technology* 6 (1): 6-16.

Glaessl, A., A. G. Schreyer, et al. (2001). "Laser surgical planning with magnetic resonance imaging-based 3-dimensional reconstructions for intralesional Nd : YAG laser therapy of a venous malformation of the neck." *Archives of Dermatology* 137(10): 1331-1335.

Gloesmann, M., B. Hermann, et al. (2003). "Histologic correlation of pig retina radial stratification with ultrahigh-resolution optical coherence tomography." *Investigative Ophthalmology & Visual Science* 44(4): 1696-1703.

Goldberg, L. and D. Mehuys (1994). "High-Power Superluminescent Diode Source." *Electronics Letters* 30(2): 1682-1684.

Goldsmith, J. A., Y. Li, et al. (2005). "Anterior chamber width measurement by high speed optical coherence tomography." *Ophthalmology* 112(2): 238-244.

Goldstein, L. E., J. A. Muffat, et al. (2003). "Cytosolic beta-amyloid deposition and supranuclear cataracts in lenses from people with Alzheimer's disease." *Lancet* 361(9365): 1258-1265.

Golubovic, B., B. E. Bouma, et al. (1996). "Thin crystal, room-temperature Cr/sup 4 +/:forstefite laser using near-infrared pumping." *Optics Letters* 21(24): 1993-1995.

Gonzalez, S. and Z. Tannous (2002). "Real-time, in vivo confocal reflectance microscopy of basal cell carcinoma." *Journal of the American Academy of Dermatology* 47(6): 869-874.

Gordon, M. O. and M. A. Kass (1999). "The Ocular Hypertension Treatment Study: design and baseline description of the participants." *Archives of Ophthalmology* 117(5): 573-83.

Grayson, T. P., J. R. Torgerson, et al. (1994). "Observation of a Nonlocal Pancharatnam Phase-Shift in the Process of Induced Coherence without Induced Emission." *Physical Review* A 49(1): 626-628.

Greaney, M. J., D. C. Hoffman, et al. (2002). "Comparison of optic nerve imaging methods to distinguish normal eyes from those with glaucoma." *Investigative Ophthalmology & Visual Science* 43(1): 140-5.

Greenfield, D. S., H. Bagga, et al. (2003). "Macular thickness changes in glaucomatous optic neuropathy detected using optical coherence tomography." *Archives of Ophthalmology* 121(1): 41-46.

Greenfield, D. S., R. W. Knighton, et al. (2000). "Effect of corneal polarization axis on assessment of retinal nerve fiber layer thickness by scanning laser polarimetry." *American Journal of Ophthalmology* 129(6): 715-722.

Griffin, R. A., D. D. Sampson, et al. (1995). "Coherence Coding for Photonic Code-Division Multiple-Access Networks." *Journal of Lightwave Technology* 13(9): 1826-1837.

Guedes, V., J. S. Schuman, et al. (2003). "Optical coherence tomography measurement of macular and nerve fiber layer thickness in normal and glaucomatous human eyes." *Ophthalmology* 110(1): 177-189.

Gueugniaud, P. Y., H. Carsin, et al. (2000). "Current advances in the initial management of major thermal burns. [Review] [76 refs]." *Intensive Care Medicine* 26(7): 848-56.

Guido, S. and R. T. Tranquillo (1993). "A Methodology for the Systematic and Quantitative Study of Cell Contact Guidance in Oriented Collagen Gels—Correlation of Fibroblast Orientation and Gel Birefringence." *Journal of Cell Science* 105: 317-331.

Gurses-Ozden, R., H. Ishikawa, et al. (1999). "Increasing sampling density improves reproducibility of optical coherence tomography measurements." *Journal of Glaucoma* 8(4): 238-41.

Guzzi, R. (1998). "Scattering Theory from Homogeneous and Coated Spheres." 1-11.

Haberland, U. B., Vladimir; Schmitt, Hans J. (1996). "Optical coherent tomography of scattering media using electrically tunable near-infrared semiconductor laser." *Applied Optics* Draft Copy.

Haberland, U. R., Walter; Blazek, Vladimir; Schmitt, Hans J. (1995). "Investigation of highly scattering media using near-infrared continuous wave tunable semiconductor laser." *Proc. SPIE*, 2389: 503-512.

Hale, G. M. and M. R. Querry (1973). "Optical-Constants of Water in 200-Nm to 200-Mum Wavelength Region." *Applied Optics* 12(3): 555-563.

Hammer, D. X., R. D. Ferguson, et al. (2002). "Image stabilization for scanning laser ophthalmoscopy." *Optics Express* 10(26): 1542.

Hara, T., Y. Ooi, et al. (1989). "Transfer Characteristics of the Microchannel Spatial Light-Modulator." *Applied Optics* 28(22): 4781-4786.

Harland, C. C., S. G. Kale, et al. (2000). "Differentiation of common benign pigmented skin lesions from melanoma by high-resolution ultrasound." *British Journal of Dermatology* 143(2): 281-289.

Hartl, I., X. D. Li, et al. (2001). "Ultrahigh-resolution optical coherence tomography using continuum generation in an air-silica microstructure optical fiber." *Optics Letters* 26(9): 608-610.

Hassenstein, A., A. A. Bialasiewicz, et al. (2000). "Optical coherence tomography in uveitis patients." *American Journal of Ophthalmology* 130(5): 669-70.

Hattenhauer, M. G., D. H. Johnson, et al. (1998). "The probability of blindness from open-angle glaucoma. [see comments]." *Ophthalmology* 105(11): 2099-104.

Hausler, G., J. M. Herrmann, et al. (1996). "Observation of light propagation in volume scatterers with 10(11)-fold slow motion." *Optics Letters* 21(14): 1087-1089.

Hazebroek, H. F. and A. A. Holscher (1973). "Interferometric Ellipsometry." *Journal of Physics E-Scientific Instruments* 6(9): 822-826.

Hazebroek, H. F. and W. M. Visser (1983). "Automated Laser Interferometric Ellipsometry and Precision Reflectometry." *Journal of Physics E-Scientific Instruments* 16(7): 654-661.

He, Z. Y., N. Mukohzaka, et al. (1997). "Selective image extraction by synthesis of the coherence function using two-dimensional optical lock-in amplifier with microchannel spatial light modulator." *Ieee Photonics Technology Letters* 9(4): 514-516.

Hee, M. R., J. A. Izatt, et al. (1993). "Femtosecond Transillumination Optical Coherence Tomography." *Optics Letters* 18(12): 950-952.

Hee, M. R., J. A. Izatt, et al. (1995). "Optical coherence tomography of the human retina." *Archives of Ophthalmology* 113(3): 325-32.

Hee, M. R., C. A. Puliafito, et al. (1998). "Topography of diabetic macular edema with optical coherence tomography." *Ophthalmology* 105(2): 360-70.

Hee, M. R., C. A. Puliafito, et al. (1995). "Quantitative assessment of macular edema with optical coherence tomography." *Archives of Ophthalmology* 113(8): 1019-29.

Hellmuth, T. and M. Welle (1998). "Simultaneous measurement of dispersion, spectrum, and distance with a fourier transform spectrometer." *Journal of Biomedical Optics* 3(1): 7-11.

Hemenger, R. P. (1989). "Birefringence of a medium of tenuous parallel cylinders." *Applied Optics* 28(18): 4030-4034.

Henry, M. (1981). "Fresnel-Arago Laws for Interference in Polarized-Light—Demonstration Experiment." *American Journal of Physics* 49(7): 690-691.

Herz, P. R., Y. Chen, et al. (2004). "Micromotor endoscope catheter for in vivo, ultrahigh-resolution optical coherence tomography." *Optics Letters* 29(19): 2261-2263.

Hirakawa, H., H. Iijima, et al. (1999). "Optical coherence tomography of cystoid macular edema associated with retinitis pigmentosa." *American Journal of Ophthalmology* 128(2): 185-91.

Hitzenberger, C. K., A. Baumgartner, et al. (1994). "Interferometric Measurement of Corneal Thickness with Micrometer Precision." *American Journal of Ophthalmology* 118(4): 468-476.

Hitzenberger, C. K., A. Baumgartner, et al. (1999). "Dispersion effects in partial coherence interferometry: Implications for Intraocular ranging." *Journal of Biomedical Optics* 4(1): 144-151.

Hitzenberger, C. K., A. Baumgartner, et al. (1998). "Dispersion induced multiple signal peak splitting in partial coherence interferometry." *Optics Communications* 154 (4): 179-185.

Hitzenberger, C. K., M. Danner, et al. (1999). "Measurement of the spatial coherence of superluminescent diodes." *Journal of Modern Optics* 46(12): 1763-1774.

Hitzenberger, C. K. and A. F. Fercher (1999). "Differential phase contrast in optical coherence tomography." *Optics Letters* 24(9): 622-624.

Hitzenberger, C. K., M. Sticker, et al. (2001). "Differential phase measurements in low-coherence interferometry without 2 pi ambiguity." *Optics Letters* 26(23): 1864-1866.

Hoeling, B. M., A. D. Fernandez, et al. (2000). "An optical coherence microscope for 3-dimensional imaging in developmental biology." *Optics Express* 6(7): 136-146.

Hoerauf, H., C. Scholz, et al. (2002). "Transscleral optical coherence tomography: a new imaging method for the anterior segment of the eye." *Archives of Ophthalmology* 120(6): 816-9.

Hoffmann, K., M. Happe, et al. (1998). "Optical coherence tomography (OCT) in dermatology." *Journal of Investigative Dermatology* 110(4): 583-583.

Hoh, S. T., D. S. Greenfield, et al. (2000). "Optical coherence tomography and scanning laser polarimetry in normal, ocular hypertensive, and glaucomatous eyes." *American Journal of Ophthalmology* 129(2): 129-35.

Hohenleutner, U., M. Hilbert, et al. (1995). "Epidermal Damage and Limited Coagulation Depth with the Flashlamp-Pumped Pulsed Dye-Laser—a Histochemical-Study." *Journal of Investigative Dermatology* 104(5): 798-802.

Holland, A. J. A., H. C. O. Martin, et al. (2002). "Laser Doppler imaging prediction of burn wound outcome in children." *Burns* 28(1): 11-17.

Hotate, K. and T. Okugawa (1994). "Optical Information-Processing by Synthesis of the Coherence Function." *Journal of Lightwave Technology* 12(7): 1247-1255.

Hourdakis, C. J. and A. Perris (1995). "A Monte-Carlo Estimation of Tissue Optical-Properties for Use in Laser Dosimetry." *Physics in Medicine and Biology* 40(3): 351-364.

Hu, Z., F. Li, et al. (2000). "Wavelength-tunable narrow-linewidth semiconductor fiber-ring laser." *IEEE Photonics Technology Letters* 12(8): 977-979.

Huang, F., W. Yang, et al. (2001). "Quadrature spectral interferometric detection and pulse shaping." *Optics Letters* 26(6): 382-384.

Huang, X. R. and R. W. Knighton (2002). "Linear birefringence of the retinal nerve fiber layer measured in vitro with a multispectral imaging micropolarimeter." *Journal of Biomedical Optics* 7(2): 199-204.

Huber, R., M. Wojtkowski, et al. (2005). "Amplified, frequency swept lasers for frequency domain reflectometry and OCT imaging: design and scaling principles." *Optics Express* 13(9): 3513-3528.

Hunter, D. G., J. C. Sandruck, et al. (1999). "Mathematical modeling of retinal birefringence scanning." *Journal of the Optical Society of America a-Optics Image Science and Vision* 16(9): 2103-2111.

Hurwitz, H. H. and R. C. Jones (1941). "A new calculus for the treatment of optical systems II. Proof of three general equivalence theorems." *Journal of the Optical Society of America* 31(7): 493-499.

Huttner, B., C. De Barros, et al. (1999). "Polarization-induced pulse spreading in birefringent optical fibers with zero differential group delay." *Optics Letters* 24(6): 370-372.

Huttner, B., B. Gisin, et al. (1999). "Distributed PMD measurement with a polarization-OTDR in optical fibers." *Journal of Lightwave Technology* 17(10): 1843-1848.

Huttner, B., J. Reecht, et al. (1998). "Local birefringence measurements in single-mode fibers with coherent optical frequency-domain reflectometry." *Ieee Photonics Technology Letters* 10(10): 1458-1460.

Hyde, S. C. W., N. P. Barry, et al. (1995). "Sub-100-Mu-M Depth-Resolved Holographic Imaging through Scattering Media in the near-Infrared." *Optics Letters* 20(22): 2330-2332.

Hyde, S. C. W., N. P. Barry, et al. (1995). "Depth-Resolved Holographic Imaging through Scattering Media by Photorefraction." *Optics Letters* 20(11): 1331-1333.

Iftimia, N. V., B. E. Bouma, et al. (2004). "Adaptive ranging for optical coherence tomography." *Optics Express* 12(17): 4025-4034.

Iida, T., N. Hagimura, et al. (2000). "Evaluation of central serous chorioretinopathy with optical coherence tomography." *American Journal of Ophthalmology* 129(1): 16-20.

Imai, M., H. Iijima, et al. (2001). "Optical coherence tomography of tractional macular elevations in eyes with proliferative diabetic retinopathy. [republished in Am J Ophthalmol. Sep. 2001;132(3):458-61 ; 11530091.]." *American Journal of Ophthalmology* 132(1): 81-4.

Indebetouw, G. and P. Klysubun (2000). "Imaging through scattering media with depth resolution by use of low-coherence gating in spatiotemporal digital holography." *Optics Letters* 25(4): 212-214.

Ip, M. S., B. J. Baker, et al. (2002). "Anatomical outcomes of surgery for idiopathic macular hole as determined by optical coherence tomography." *Archives of Ophthalmology* 120(1): 29-35.

Ismail, R., V. Tanner, et al. (2002). "Optical coherence tomography imaging of severe commotio retinae and associated macular hole." *British Journal of Ophthalmology* 86(4): 473-4.

Izatt, J. A., M. R. Hee, et al. (1994). "Optical Coherence Microscopy in Scattering Media." *Optics Letters* 19(8): 590-592.

Izatt, J. A., M. R. Hee, et al. (1994). "Micrometer-scale resolution imaging of the anterior eye in vivo with optical coherence tomography." *Archives of Ophthalmology* 112 (12): 1584-9.

Izatt, J. A., M. D. Kulkarni, et al. (1997). "In vivo bidirectional color Doppler flow imaging of picoliter blood volumes using optical coherence tomography." *Optics Letters* 22(18): 1439-1441.

Izatt, J. A., M. D. Kulkarni, et al. (1996). "Optical coherence tomography and microscopy in gastrointestinal tissues." *IEEE Journal of Selected Topics in Quantum Electronics* 2(4): 1017.

Jacques, S. L., J. S. Nelson, et al. (1993). "Pulsed Photothermal Radiometry of Port-Wine-Stain Lesions." *Applied Optics* 32(13): 2439-2446.

Jacques, S. L., J. R. Roman, et al. (2000). "Imaging superficial tissues with polarized light." *Lasers in Surgery and Medicine* 26(2): 119-129.

Jang, I. K., B. E. Bouma, et al. (2002). "Visualization of coronary atherosclerotic plaques in patients using optical coherence tomography: Comparison with intravascular ultrasound." *Journal of the American College of Cardiology* 39(4): 604-609.

Jang, I. K., B. D. MacNeill, et al. (2002). "In-vivo characterization of coronary plaques in patients with ST elevation acute myocardial infarction using optical coherence tomography (OCT)." *Circulation* 106(19): 698-698 3440 Suppl. S.

Jang, I. K., G. J. Tearney, et al. (2000). "Comparison of optical coherence tomography and intravascular ultrasound for detection of coronary plaques with large lipid-core in living patients." *Circulation* 102(18): 509-509.

Jeng, J. C., A. Bridgeman, et al. (2003). "Laser Doppler imaging determines need for excision and grafting in advance of clinical judgement: a prospective blinded trial." *Burns* 29(7): 665-670.

Jesser, C. A., S. A. Boppart, et al. (1999). "High resolution imaging of transitional cell carcinoma with optictal coherence tomography: feasibility for the evaluation of bladder pathology." *British Journal of Radiology* 72: 1170-1176.

Johnson, C. A., J. L. Keltner, et al. (2002). "Baseline visual field characteristics in the ocular hypertension treatment study." *Ophthalmology* 109(3): 432-7.

Jones, R. C. (1941). "A new calculus for the treatment of optical systems III. The Sohncke theory of optical activity." *Journal of the Optical Society of America* 31 (7): 500-503.

Jones, R. C. (1941). "A new calculus for the treatment of optical systems I. Description and discussion of the calculus." *Journal of the Optical Society of America* 31(7): 488-493.

Jones, R. C. (1942). "A new calculus for the treatment of optical systems. IV." *Journal of the Optical Society of America* 32(8): 486-493.

Jones, R. C. (1947). "A New Calculus for the Treatment of Optical Systems .6. Experimental Determination of the Matrix." *Journal of the Optical Society of America* 37(2): 110-112.

Jones, R. C. (1947). "A New Calculus for the Treatment of Optical Systems .5. A More General Formulation, and Description of Another Calculus." *Journal of the Optical Society of America* 37(2): 107-110.

Jones, R. C. (1948). "A New Calculus for the Treatment of Optical Systems .7. Properties of the N-Matrices." *Journal of the Optical Society of America* 38(8): 671-685.

Jones, R. C. (1956). "New Calculus for the Treatment of Optical Systems .8. Electromagnetic Theory." *Journal of the Optical Society of America* 46(2): 126-131.

Jopson, R. MThe ., L. E. Nelson, et al. (1999). "Measurement of second-order polarization-mode dispersion vectors in optical fibers." *Ieee Photonics Technology Letters* 11 (9): 1153-1155.

Jost, B. M., A. V. Sergienko, et al. (1998). "Spatial correlations of spontaneously down-converted photon pairs detected with a single-photon-sensitive CCD camera." *Optics Express* 3(2): 81-88.

Kaplan, B., E. Compain, et al. (2000). "Phase-modulated Mueller ellipsometry characterization of scattering by latex sphere suspensions." *Applied Optics* 39 (4): 629-636.

Kass, M. A., D. K. Heuer, et al. (2002). "The Ocular Hypertension Treatment Study: a randomized trial determines that topical ocular hypotensive medication delays or prevents the onset of primary open-angle glaucoma." *Archives of Ophthalmology* 120(6): 701-13; discussion 829-30.

Kasuga, Y., J. Arai, et al. (2000). "Optical coherence tomograghy to confirm early closure of macular holes." *American Journal of Ophthalmology* 130(5): 675-6.

Kaufman, T., S. N. Lusthaus, et al. (1990). "Deep Partial Skin Thickness Burns—a Reproducibile Animal-Model to Study Burn Wound-Healing." *Burns* 16(1): 13-16.

Kemp, N. J., J. Park, et al. (2005). "High-sensitivity determination of birefringence in turbid media with enhanced polarization-sensitive optical coherence tomography." *Journal of the Optical Society of America a-Optics Image Science and Vision* 22(3): 552-560.

Kerrigan-Baumrind, L. A., H. A. Quigley, et al. (2000). "Number of ganglion cells in glaucoma eyes compared with threshold visual field tests in the same persons." *Investigative Ophthalmology & Visual science* 41(3): 741-8.

Kesen, M. R., G. L. Spaeth, et al. (2002). "The Heidelberg Retina Tomograph vs clinical impression in the diagnosis of glaucoma." *American Journal of Ophthalmology* 133(5): 613-6.

Kienle, A. and R. Hibst (1995). "A New Optimal Wavelength for Treatment of Port-Wine Stains." *Physics in Medicine and Biology* 40(10): 1559-1576.

Kienle, A., L. Lilge, et al. (1996). "Spatially resolved absolute diffuse reflectance measurements for noninvasive determination of the optical scattering and absorption coefficients of biological tissue." *Applied Optics* 35(13): 2304-2314.

Kim, B. Y. and S. S. Choi (1981). "Analysis and Measurement of Birefringence in Single-Mode Fibers Using the Backscattering Method." *Optics Letters* 6(11): 578-580.

Kimel, S., L. O. Svaasand, et al. (1994). "Differential Vascular-Response to Laser Photothermolysis." *Journal of Investigative Dermatology* 103(5): 693-700.

Kloppenberg, F. W. H., G. Beerthuizen, et al. (2001). "Perfusion of burn wounds assessed by Laser Doppler Imaging is related to burn depth and healing time." *Burns* 27(4): 359-363.

Knighton, R. W. and X. R. Huang (2002). "Analytical methods for scanning laser polarimetry." *Optics Express* 10(21): 1179-1189.

Knighton, R. W., X. R. Huang, et al. (2002). "Analytical model of scanning laser polarimetry for retinal nerve fiber layer assessment." *Investigative Ophthalmology & Visual Science* 43(2): 383-392.

Knuettel, A. R. S., Joseph M.; Shay, M.; Knutson, Jay R. (1994). "Stationary low-coherence light imaging and spectroscopy using a CCD camera." *Proc. SPIE*, vol. 2135: p. 239-250.

Knuttel, A. and M. Boehlau-Godau (2000). "Spatially confined and temporally resolved refractive index and scattering evaluation in human skin performed with optical coherence tomography." *Journal of Biomedical Optics* 5(1): 83-92.

Knuttel, A. and J. M. Schmitt (1993). "Stationary Depth-Profiling Reflectometer Based on Low-Coherence Interferometry." *Optics Communications* 102(3-4): 193-198.

Knuttel, A., J. M. Schmitt, et al. (1994). "Low-Coherence Reflectometry for Stationary Lateral and Depth Profiling with Acoustooptic Deflectors and a Ccd Camera." *Optics Letters* 19(4): 302-304.

Kobayashi, M., H. Hanafusa, et al. (1991). "Polarization-Independent Interferometric Optical-Time-Domain Reflectometer." *Journal of Lightwave Technology* 9(5): 623-628.

Kolios, M. C., M. D. Sherar, et al. (1995). "Large Blood-Vessel Cooling in Heated Tissues—a Numerical Study." *Physics in Medicine and Biology* 40(4): 477-494.

Koozekanani, D., K. Boyer, et al. (2001). "Retinal thickness measurements from optical coherence tomography using a Markov boundary model." *Ieee Transactions on Medical Imaging* 20(9): 900-916.

Kop, R. H. J. and R. Sprik (1995). "Phase-sensitive interferometry with ultrashort optical pulses." *Review of Scientific Instruments* 66(12): 5459-5463.

Kramer, R. Z., J. Bella, et al. (1999). "Sequence dependent conformational variations of collagen triple-helical structure." *Nature Structural Biology* 6(5): 454-7.

Kulkarni, M. D., T. G. van Leeuwen, et al. (1998). "Velocity-estimation accuracy and frame-rate limitations in color Doppler optical coherence tomography." *Optics Letters* 23(13): 1057-1059.

Kwon, Y. H., C. S. Kim, et al. (2001). "Rate of visual field loss and long-term visual outcome in primary open-angle glaucoma." *American Journal of Ophthalmology* 132(1): 47-56.

Kwong, K. F., D. Yankelevich, et al. (1993). "400-Hz Mechanical Scanning Optical Delay-Line." *Optics Letters* 18(7): 558-560.

Landers, J., I. Goldberg, et al. (2002). "Analysis of risk factors that may be associated with progression from ocular hypertension to primary open angle glaucoma." *Clin Experiment Ophthalmogy* 30(4): 242-7.

Laszlo, A. and A. Venetianer (1998). Heat resistance in mammalian cells: Lessons and challenges. *Stress of Life*. 851: 169-178.

Laszlo, A. and A. Venetianer (1998). "Heat resistance in mammalian cells: lessons and challenges. [Review] [52 refs]." *Annals of the New York Academy of Sciences* 851: 169-78.

Laufer, J., R. Simpson, et al. (1998). "Effect of temperature on the optical properties of ex vivo human dermis and subdermis." *Physics in Medicine and Biology* 43(9): 2479-2489.

Lederer, D. E., J. S. Schuman, et al. (2003). "Analysis of macular volume in normal and glaucomatous eyes using optical coherence tomography." *American Journal of Ophthalmology* 135(6): 838-843.

Lee, P. P., Z. W. Feldman, et al. (2003). "Longitudinal prevalence of major eye diseases." *Archives of Ophthalmology* 121(9): 1303-1310.

Lehrer, M. S., T. T. Sun, et al. (1998). "Strategies of epithelial repair: modulation of stem cell and transit amplifying cell proliferation." *Journal of Cell Science* 111(Pt 19): 2867-75.

Leibowitz, H. M., D. E. Krueger, et al. (1980). "The Framingham Eye Study monograph: An ophthalmological and epidemiological study of cataract, glaucoma, diabetic retinopathy, macular degeneration, and visual acuity in a general population of 2631 adults, 1973-1975." *Survey of Ophthalmology* 24(Suppl): 335-610.

Leitgeb, R., C. K. Hitzenberger, et al. (2003). "Performance of fourier domain vs. time domain optical coherence tomography." *Optics Express* 11(8): 889-894.

Leitgeb, R., L. F. Schmetterer, et al. (2002). "Flow velocity measurements by frequency domain short coherence interferometry." *Proc. SPIE* 4619: 16-21.

Leitgeb, R. A., W. Drexler, et al. (2004). "Ultrahigh resolution Fourier domain optical coherence tomography." *Optics Express* 12(10): 2156-2165.

Leitgeb, R. A., C. K. Hitzenberger, et al. (2003). "Phase-shifting algorithm to achieve high-speed long-depth-range probing by frequency-domain optical coherence tomography." *Optics Letters* 28(22): 2201-2203.

Leitgeb, R. A., L. Schmetterer, et al. (2003). "Real-time assessment of retinal blood flow with ultrafast acquisition by color Doppler Fourier domain optical coherence tomography." *Optics Express* 11(23): 3116-3121.

Leitgeb, R. A., L. Schmetterer, et al. (2004). "Real-time measurement of in vitro flow by Fourier-domain color Doppler optical coherence tomography." *Optics Letters* 29 (2): 171-173.

LeRoyBrehonnet, F. and B. LeJeune (1997). "Utilization of Mueller matrix formalism to obtain optical targets depolarization and polarization properties." *Progress in Quantum Electronics* 21(2): 109-151.

Leske, M. C., A. M. Connell, et al. (1995). "Risk factors for open-angle glaucoma. The Barbados Eye Study. [see comments]." *Archives of Ophthalmology* 113(7): 918-24.

Leske, M. C., A. M. Connell, et al. (2001). "Incidence of open-angle glaucoma: the Barbados Eye Studies. The Barbados Eye Studies Group. [see comments]." *Archives of Ophthalmology* 119(1): 89-95.

Leske, M. C., A. Heijl, et al. (1999). "Early Manifest Glaucoma Trial. Design and Baseline Data." *Ophthalmology* 106(11): 2144-2153.

Lewis, S. E., J. R. DeBoer, et al. (2005). "Sensitive, selective, and analytical improvements to a porous silicon gas sensor." *Sensors and Actuators B: Chemical* 110(1): 54-65.

Lexer, F., C. K. Hitzenberger, et al. (1999). "Dynamic coherent focus OCT with depth-independent transversal resolution." *Journal of Modern Optics* 46(3): 541-553.

Li, X., C. Chudoba, et al. (2000). "Imaging needle for optical coherence tomography." *Optics Letters* 25: 1520-1522.

Li, X., T. H. Ko, et al. (2001). "Intraluminal fiber-optic Doppler imaging catheter for structural and functional optical coherence tomography." *Optics Letters* 26: 1906-1908.

Liddington, M. I. and P. G. Shakespeare (1996). "Timing of the thermographic assessment of burns." *Burns* 22(1): 26-8.

Lindmo, T., D. J. Smithies, et al. (1998). "Accuracy and noise in optical Doppler tomography studied by Monte Carlo simulation." *Physics in Medicine and Biology* 43(10): 3045-3064.

Liu, J., X. Chen, et al. (1999). "New thermal wave aspects on burn evaluation of skin subjected to instantaneous heating." *IEEE Transactions on Biomedical Engineering* 46(4): 420-8.

Luke, D. G., R. McBride, et al. (1995). "Polarization mode dispersion minimization in fiber-wound piezoelectric cylinders." *Optics Letters* 20(24): 2550-2552.

MacNeill, B. D., I. K. Jang, et al. (2004). "Focal and multi-focal plaque distributions in patients with macrophage acute and stable presentations of coronary artery disease." *Journal of the American College of Cardiology* 44(5): 972-979.

Mahgerefteh, D. and C. R. Menyuk (1999). "Effect of first-order PMD compensation on the statistics of pulse broadening in a fiber with randomly varying birefringence." *Ieee Photonics Technology Letters* 11(3): 340-342.

Maitland, D. J. and J. T. Walsh, Jr. (1997). "Quantitative measurements of linear birefringence during heating of native collagen." *Lasers in Surgery & Medicine* 20 (3): 310-8.

Majaron, B., S. M. Srinivas, et al. (2000). "Deep coagulation of dermal collagen with repetitive Er : YAG laser irradiation." *Lasers in Surgery and Medicine* 26(2): 215-222.

Mansuripur, M. (1991). "Effects of High-Numerical-Aperture Focusing on the State of Polarization in Optical and Magnetooptic Data-Storage Systems." *Applied Optics* 30(22): 3154-3162.

Marshall, G. W., S. J. Marshall, et al. (1997). "The dentin substrate: structure and properties related to bonding." *Journal of Dentistry* 25(6): 441-458.

Martin, P. (1997). "Wound healing—Aiming for perfect skin regeneration." *Science* 276 (5309): 75-81.

Martinez, O. E. (1987). "3000 Times Grating Compressor with Positive Group-Velocity Dispersion—Application to Fiber Compensation in 1.3-1.6 Mu-M Region." *Ieee Journal of Quantum Electronics* 23(1): 59-64.

Martinez, O. E., J. P. Gordon, et al. (1984). "Negative Group-Velocity Dispersion Using Refraction." *Journal of the Optical Society of America a-Optics Image Science and Vision* 1(10): 1003-1006.

McKinney, J. D., M. A. Webster, et al. (2000). "Characterization and imaging in optically scattering media by use of laser speckle and a variable-coherence source." *Optics Letters* 25(1): 4-6.

Miglior, S., M. Casula, et al. (2001). "Clinical ability of Heidelberg retinal tomograph examination to detect glaucomatous visual field changes." *Ophthalmology* 108 (9): 1621-7.

Milner, T. E., D. M. Goodman, et al. (1996). "Imaging laser heated subsurface chromophores in biological materials: Determination of lateral physical dimensions." *Physics in Medicine and Biology* 41(1): 31-44.

Milner, T. E., D. M. Goodman, et al. (1995). "Depth Profiling of Laser-Heated Chromophores in Biological Tissues by Pulsed Photothermal Radiometry." *Journal of the Optical Society of America a-Optics Image Science and Vision* 12 (7): 1479-1488.

Milner, T. E., D. J. Smithies, et al. (1996). "Depth determination of chromophores in human skin by pulsed photothermal radiometry." *Applied Optics* 35(19): 3379-3385.

Mishchenko, M. I. and J. W. Hovenier (1995). "Depolarization of Light Backscattered by Randomly Oriented Nonspherical Particles." *Optics Letters* 20(12): 1356-&.

Mistlberger, A., J. M. Liebmann, et al. (1999). "Heidelberg retina tomography and optical coherence tomography in normal, ocular-hypertensive, and glaucomatous eyes." *Ophthalmology* 106(10): 2027-32.

Mitsui, T. (1999). "High-speed detection of ballistic photons propagating through suspensions using spectral interferometry." *Japanese Journal of Applied Physics Part 1—Regular Papers Short Notes & Review Papers* 38(5A): 2978-2982.

Molteno, A. C., N. J. Bosma, et al. (1999). "Otago glaucoma surgery outcome study: long-term results of trabeculectomy—1976 to 1995." *Ophthalmology* 106(9): 1742-50.

Morgner, U., W. Drexler, et al. (2000). "Spectroscopic optical coherence tomography." *Optics Letters* 25(2): 111-113.

Morgner, U., F. X. Kartner, et al. (1999). "Sub-two-cycle pulses from a Kerr-lens mode-locked Ti : sapphire laser (vol. 24, p. 411, 1999)." *Optics Letters* 24(13): 920-920.

Mourant, J. R., A. H. Hielscher, et al. (1998). "Evidence of intrinsic differences in the light scattering properties of tumorigenic and nontumorigenic cells." *Cancer Cytopathology* 84(6): 366-374.

Muller, M., J. Squier, et al. (1998). "Dispersion pre-compensation of 15 femtosecond optical pulses for high-numerical-aperture objectives." *Journal of Microscopy-Oxford* 191: 141-150.

Muscat, S., N. McKay, et al. (2002). "Repeatability and reproducibility of corneal thickness measurements by optical coherence tomography." *Investigative Ophthalmology & Visual Science* 43(6): 1791-5.

Musch, D. C., P. R. Lichter, et al. (1999). "The Collaborative Initial Glaucoma Treatment Study. Study Design, MethodsR, and Baseline Characteristics of Enrolled Patients." *Ophthalmology* 106: 653-662.

Neerken, S., Lucassen, G.W., Bisschop, M.A., Lenderink, E., Nuijs, T.A.M. (2004). "Characterization of age-related effects in human skin: A comparative study that applies confocal laser scanning microscopy and optical coherence tomography." *Journal of Biomedical Optics* 9(2): 274-281.

Nelson, J. S., K. M. Kelly, et al. (2001). "Imaging blood flow in human port-wine stain in situ and in real time using optical Doppler tomography." *Archives of Dermatology* 137(6): 741-744.

Newson, T. P., F. Farahi, et al. (1988). "Combined Interferometric and Polarimetric Fiber Optic Temperature Sensor with a Short Coherence Length Source." *Optics Communications* 68(3): 161-165.

November, L. J. (1993). "Recovery of the Matrix Operators in the Similarity and Congruency Transformations—Applications in Polarimetry." *Journal of the Optical Society of America a-Optics Image Science and Vision* 10(4): 719-739.

Oh, W. Y., S. H. Yun, et al. (2005). "Wide tuning range wavelength-swept laser with two semiconductor optical amplifiers." *Ieee Photonics Technology Letters* 17(3): 678-680.

Oka, K. and T. Kato (1999). "Spectroscopic polarimetry with a channeled spectrum." *Optics Letters* 24(21): 1475-1477.

Okugawa, T. and K. Rotate (1996). "Real-time optical image processing by synthesis of the coherence function using real-time holography." *Ieee Photonics Technology Letters* 8(2): 257-259.

Oshima, M., R. Torii, et al. (2001). "Finite element simulation of blood flow in the cerebral artery." *Computer Methods in Applied Mechanics and Engineering* 191 (6-7): 661-671.

Pan, Y. T., H. K. Xie, et al. (2001). "Endoscopic optical coherence tomography based on a microelectromechanical mirror." *Optics Letters* 26(24): 1966-1968.

Parisi, V., G. Manni, et al. (2001). "Correlation between optical coherence tomography, pattern electroretinogram, and visual evoked potentials in open-angle glaucoma patients." *Ophthalmology* 108(5): 905-12.

Park, B. H., M. C. Pierce, et al. (2005). "Real-time fiber-based multi-functional spectral-domain optical coherence tomography at 1.3 mu m." *Optics Express* 13(11): 3931-3944.

Park, D. H., J. W. Hwang, et al. (1998). "Use of laser Doppler flowmetry for estimation of the depth of burns." *Plastic and Reconstructive Surgery* 101(6): 1516-1523.

Pendry, J. B., A. J. Holden, et al. (1999). "Magnetism from conductors and enhanced nonlinear phenomena." *Ieee Transactions on Microwave Theory and Techniques* 47(11): 2075-2084.

Penninckx, D. and V. Morenas (1999). "Jones matrix of polarization mode dispersion." *Optics Letters* 24(13): 875-877.

Pierce, M. C., M. Shishkov, et al. (2005). "Effects of sample arm motion in endoscopic polarization-sensitve optical coherence tomography." *Optics Express* 13(15): 5739-5749.

Pircher, M., E. Gotzinger, et al. (2003). "Measurement and imaging of water concentration in human cornea with differential absorption optical coherence tomography." *Optics Express* 11(18): 2190-2197.

Pircher, M., E. Gotzinger, et al. (2003). "Speckle reduction in optical coherence tomography by frequency compounding." *Journal of Biomedical Optics* 8(3): 565-569.

Podoleanu, A. G., G. M. Dobre, et al. (1998). "En-face coherence imaging using galvanometer scanner modulation." *Optics Letters* 23(3): 147-149.

Podoleanu, A. G. and D. A. Jackson (1999). "Noise analysis of a combined optical coherence tomograph and a confocal scanning ophthalmoscope." *Applied Optics* 38(10): 2116-2127.

Podoleanu, A. G., J. A. Rogers, et al. (2000). "Three dimensional OCT images from retina and skin." *Optics Express* 7(9): 292-298.

Podoleanu, A. G., M. Seeger, et al. (1998). "Transversal and longitudinal images from the retina of the living eye using low coherence reflectometry." *Journal of Biomedical Optics* 3(1): 12-20.

Poole, C. D. (1988). "Statistical Treatment of Polarization Dispersion in Single-Mode Fiber." *Optics Letters* 13(8): 687-689.

Povazay, B., K. Bizheva, et al. (2002). "Submicrometer axial resolution optical coherence tomography." *Optics Letters* 27(20): 1800-1802.

Qi, B., A. P. Himmer, et al. (2004). "Dynamic focus control in high-speed optical coherence tomography based on a microelectromechanical mirror." *Optics Communications* 232(1-6): 123-128.

Radhakrishnan, S., A. M. Rollins, et al. (2001). "Real-time optical coherence tomography of the anterior segment at 1310 nm." *Archives of Ophthalmology* 119(8): 1179-1185.

Rogers, A. J. (1981). "Polarization-Optical Time Domain Reflectometry—a Technique for the Measurement of Field Distributions." Applied Optics 20(6): 1060-1074.

Rollins, A. M. and J. A. Izatt (1999). "Optimal interferometer designs for optical coherence tomography." *Optics Letters* 24(21): 1484-1486.

Rollins, A. M., R. Ung-arunyawee, et al. (1999). "Real-time in vivo imaging of human gastrointestinal ultrastructure by use of endoscopic optical coherence tomography with a novel efficient interferometer design." *Optics Letters* 24(19): 1358-1360.

Rollins, A. M., S. Yazdanfar, et al. (2002). "Real-time in vivo colors Doppler optical coherence tomography." *Journal of Biomedical Optics* 7(1): 123-129.

Rollins, A. M., S. Yazdanfar, et al. (2000). "Imaging of human retinal hemodynamics using color Doppler optical coherence tomography." *Investigative Ophthalmology & Visual Science* 41(4): S548-S548.

Sandoz, P. (1997). "Wavelet transform as a processing tool in white-light interferometry." *Optics Letters* 22(14): 1065-1067.

Sankaran, V., M. J. Everett, et al. (1999). "Comparison of polarized-light propagation in biological tissue and phantoms." *Optics Letters* 24(15): 1044-1046.

Sankaran, V., J. T. Walsh, et al. (2000). "Polarized light propagation through tissue phanto, ehms containing densely packed scatterers." *Optics Letters* 25(4): 239-241.

Sarunic, M. V., M. A. Choma, et al. (2005). "Instantaneous complex conjugate resolved spectral domain and swept-source OCT using 3×3 fiber couplers." *Optics Express* 13(3): 957-967.

Sathyam, U. S., B. W. Colston, et al. (1999). "Evaluation of optical coherence quantitation of analytes in turbid media by use of two wavelengths." *Applied Optics* 38(10): 2097-2104.

Schmitt, J. M. (1997). "Array detection for speckle reduction in optical coherence microscopy." *Physics in Medicine and Biology* 42(7): 1427-1439.

Schmitt, J. M. (1999). "Optical coherence tomography (OCT): A review." *Ieee Journal of Selected Topics in Quantum Electronics* 5(4): 1205-1215.

Schmitt, J. M. and A. Knuttel (1997). "Model of optical coherence tomography of heterogeneous tissue." *Journal of the Optical Society of America a-Optics Image Science and Vision* 14(6): 1231-1242.

Schmitt, J. M., S. L. Lee, et al. (1997). "An optical coherence microscope with enhanced resolving power in thick tissue." *Optics Communications* 142(4-6): 203-207.

Schmitt, J. M., S. H. Xiang, et al. (1998). "Differential absorption imaging with optical coherence tomography." *Journal of the Optical Society of America a-Optics Image Science and Vision* 15(9): 2288-2296.

Schmitt, J. M., S. H. Xiang, et al. (1999). "Speckle in optical coherence tomography." *Journal of Biomedical Optics* 4(1): 95-105.

Schmitt, J. M., M. J. Yadlowsky, et al. (1995). "Subsurface Imaging of Living Skin with Optical Coherence Microscopy." *Dermatology* 191(2): 93-98.

Shi, H., J. Finlay, et al. (1997). "Multiwavelength 10-GHz picosecond pulse generation from a single-stripe semiconductor diode laser." *Ieee Photonics Technology Letters* 9(11): 1439-1441.

Shi, H., I. Nitta, et al. (1999). "Demonstration of phase correlation in multiwavelength mode-locked semiconductor diode lasers." *Optics Letters* 24(4): 238-240.

Simon, R. (1982). "The Connection between Mueller and Jones Matrices of Polarization Optics." *Optics Communications* 42(5): 293-297.

Smith, P. J. M., (2000) "Variable-Focus Microlenses as a Potential Technology for Endoscopy." *SPIE* (vol. 3919), USA pp. 187-192.

Smithies, D. J., T. Lindmo, et al. (1998). "Signal attenuation and localization in optical coherence tomography studied by Monte Carlo simulation." *Physics in Medicine and Biology* 43(10): 3025-3044.

Sorin, W. V. and D. F. Gray (1992). "Simultaneous Thickness and Group Index Measurement Using Optical Low-Coherence Reflectometry." *Ieee Photonics Technology Letters* 4(1): 105-107.

Sticker, M., C. K. Hitzenberger, et al. (2001). "Quantitative differential phase measurement and imaging in transparent and turbid media by optical coherence tomography." *Optics Letters* 26(8): 518-520.

Sticker, M., M. Pircher, et al. (2002). "En face imaging of single cell layers by differential phase-contrast optical coherence microscopy." *Optics Letters* 27(13): 1126-1128.

Stoller, P., B. M. Kim, et al. (2002). "Polarization-dependent optical second-harmonic imaging of a rat-tail tendon." *Journal of Biomedical Optics* 7(2): 205-214.

Sun, C. S. (2003). "Multiplexing of fiber-optic acoustic sensors in a Michelson interferometer configuration." *Optics Letters* 28(12): 1001-1003.

Swanson, E. A., J. A. Izatt, et al. (1993). "In-Vivo Retinal Imaging by Optical Coherence Tomography." *Optics Letters* 18(21): 1864-1866.

Takada, K., A. Himeno, et al. (1991). "Phase-Noise and Shot-Noise Limited Operations of Low Coherence Optical-Time Domain Reflectometry." *Applied Physics Letters* 59(20): 2483-2485.

Takenaka, H. (1973). "Unified Formalism for Polarization Optics by Using Group-Theory I (Theory)." *Japanese Journal of Applied Physics* 12(2): 226-231.

Tanno, N., T. Ichimura, et al. (1994). "Optical Multimode Frequency-Domain Reflectometer." *Optics Letters* 19(8): 587-589.

Tan-no, N., T. Ichimura, et al. (1994). "Optical Multimode Frequency-Domain Reflectometer." *Optics Letters* 19(8): 587-589.

Targowski, P., M. Wojtkowski, et al. (2004). "Complex spectral OCT in human eye imaging in vivo." *Optics Communications* 229(1-6): 79-84.

Tearney, G. J., S. A. Boppart, et al. (1996). "Scanning single-mode fiber optic catheter-endoscope for optical coherence tomography (vol. 21, p. 543, 1996)." *Optics Letters* 21(12): 912-912.

Tearney, G. J., B. E. Bouma, et al. (1996). "Rapid acquisition of in vivo biological images by use of optical coherence tomography." *Optics Letters* 21(17): 1408-1410.

Tearney, G. J., B. E. Bouma, et al. (1997). "In vivo endoscopic optical biopsy with optical coherence tomography." *Science* 276(5321): 2037-2039.

Tearney, G. J., M. E. Brezinski, et al. (1996). "Catheter-based optical imaging of a human coronary artery." *Circulation* 94(11): 3013-3013.

Tearney, G. J., M. E. Brezinski, et al. (1997). "In vivo endoscopic optical biopsy with optical coherence tomography." *Science* 276(5321): 2037-9.

Tearney, G. J., M. E. Brezinski, et al. (1997). "Optical biopsy in human gastrointestinal tissue using optical coherence tomography." *American Journal of Gastroenterology* 92(10): 1800-1804.

Tearney, G. J., M. E. Brezinski, et al. (1995). "Determination of the refractive index of highly scattering human tissue by optical coherence tomography." *Optics Letters* 20(21): 2258-2260.

Tearney, G. J., I. K. Jong, et al. (2000). "Porcine coronary imaging in vivo by optical coherence tomography." *Acta Cardiologica* 55(4): 233-237.

Tearney, G. J., R. H. Webb, et al. (1998). "Spectrally encoded confocal microscopy." *Optics Letters* 23(15): 1152-1154.

Tearney, G. J., H. Yabushita, et al. (2003). "Quantification of macrophage content in atherosclerotic plaques by optical coherence tomography." *Circulation* 107(1): 113-119.

Tower, T. T. and R. T. Tranquillo (2001). "Alignment maps of tissues: I. Microscopic elliptical polarimetry." *Biophysical Journal* 81(5): 2954-2963.

Tower, T. T. and R. T. Tranquillo (2001). "Alignment maps of tissues: II. Fast harmonic analysis for imaging." *Biophysical Journal* 81(5): 2964-2971.

Troy, T. L. and S. N. Thennadil (2001). "Optical properties of human skin in the near infrared wavelength range of 1000 to 2200 nm." *Journal of Biomedical Optics* 6 (2): 167-176.

Vabre, L., A. Dubois, et al. (2002). "Thermal-light full-field optical coherence tomography." *Optics Letters* 27(7): 530-532.

Vakhtin, A. B., D. J. Kane, et al. (2003). "Common-path interferometer for frequency-domain optical coherence tomography." *Applied Optics* 42(34): 6953-6958.

Vakhtin, A. B., K. A. Peterson, et al. (2003). "Differential spectral interferometry: an imaging technique for biomedical applications." *Optics Letters* 28(15): 1332-1334.

Vakoc, B. J., S. H. Yun, et al. (2005). "Phase-resolved optical frequency domain imaging." *Optics Express* 13(14): 5483-5493.

van Leeuwen, T. G., M. D. Kulkarni, et al. (1999). "High-flow-velocity and shear-rate imaging by use of color Doppler optical coherence tomography." *Optics Letters* 24(22): 1584-1586.

Vansteenkiste, N., P. Vignolo, et al. (1993). "Optical Reversibility Theorems for Polarization—Application to Remote-Control of Polarization." *Journal of the Optical Society of America a-Optics Image Science and Vision* 10(10): 2240-2245.

Vargas, O., E. K. Chan, et al. (1999). "Use of an agent to reduce scattering in skin." *Lasers in Surgery and Medicine* 24(2): 133-141.

Wang, R. K. (1999). "Resolution improved optical coherence-gated tomography for imaging through biological tissues." *Journal of Modern Optics* 46(13): 1905-1912.

Wang, X. J., T. E. Milner, et al. (1997). "Measurement of fluid-flow-velocity profile in turbid media by the use of optical Doppler tomography." *Applied Optics* 36(1): 144-149.

Wang, X. J., T. E. Milner, et al. (1995). "Characterization of Fluid-Flow Velocity by Optical Doppler Tomography." *Optics Letters* 20(11): 1337-1339.

Wang, Y. M., J. S. Nelson, et al. (2003). "Optimal wavelength for ultrahigh-resolution optical coherence tomography." *Optics Express* 11(12): 1411-1417.

Wang, Y. M., Y. H. Zhao, et al. (2003). "Ultrahigh-resolution optical coherence tomography by broadband continuum generation from a photonic crystal fiber." *Optics Letters* 28(3): 182-184.

Watkins, L. R., S. M. Tan, et al. (1999). "Determination of interferometer phase distributions by use of wavelets." *Optics Letters* 24(13): 905-907.

Wetzel, J. (2001). "Optical coherence tomography in dermatology: a review." *Skin Research and Technology* 7(1): 1-9.

Wentworth, R. H. (1989). "Theoretical Noise Performance of Coherence-Multiplexed Interferometric Sensors." *Journal of Lightwave Technology* 7(6): 941-956.

Westphal, V., A. M. Rollins, et al. (2002). "Correction of geometric and refractive image distortions in optical coherence tomography applying Fermat's principle." *Optics Express* 10(9): 397-404.

Westphal, V., S. Yazdanfar, et al. (2002). "Real-time, high velocity-resolution color Doppler optical coherence tomography." *Optics Letters* 27(1): 34-36.

Williams, P. A. (1999). "Rotating-wave-plate Stokes polarimeter for differential group delay measurments of polarization-mode dispersion." *Applied Optics* 38(31): 6508-6515.

Wojtkowski, M., T. Bajraszewski, et al. (2003). "Real-time in vivo imaging by high-speed spectral optical coherence tomography." *Optics Letters* 28(19): 1745-1747.

Wojtkowski, M., A. Kowalczyk, et al. (2002). "Full range complex spectral optical coherence tomography technique in eye imaging." *Optics Letters* 27(16): 1415-1417.

Wojtkowski, M., R. Leitgeb, et al. (2002). "In vivo human retinal imaging by Fourier domain optical coherence tomography." *Journal of Biomedical Optics* 7(3): 457-463.

Wojtkowski, M., R. Leitgeb, et al. (2002). "Fourier domain OCT imaging of the human eye in vivo." *Proc. SPIE* 4619: 230-236.

Wojtkowski, M., V. J. Srinivasan, et al. (2004). "Ultrahigh-resolution, high-speed, Fourier domain optical coherence tomography and methods for dispersion compensation." *Optics Express* 12(11): 2404-2422.

Wong, B. J. F., Y. H. Zhao, et al. (2004). "Imaging the internal structure of the rat cochlea using optical coherence tomography at 0.827 mu m and 1.3 mu m." *Otolaryngology-Head and Neck Surgery* 130(3): 334-338.

Yabushita, H. B., et al. (2002) "Measurement of Thin Fibrous Caps in Atherosclerotic Plaques by Optical Coherence Tomography." American Heart Association, Inc, Circulation 2002;106;1640.

Yang, C., A. Wax, et al. (2001). "Phase-dispersion optical tomography." *Optics Letters* 26(10): 686-688.

Yang, C., A. Wax, et al. (2001). "Phase-referenced interferometer with subwavelength and subhertz sensitivity applied to the study of cell membrane dynamics." *Optics Letters* 26(16): 1271-1273.

Yang, C. H., A. Wax, et al. (2001). "Phase-dispersion optical tomography." *Optics Letters* 26(10): 686-688.

Yang, C. H., A. Wax, et al. (2000). "Interferometric phase-dispersion microscopy." *Optics Letters* 25(20): 1526-1528.

Yang, V. X. D., M. L. Gordon, et al. (2002). "Improved phase-resolved optical Doppler tomography using the Kasai velocity estimator and histogram segmentation." *Optics Communications* 208(4-6): 209-214.

Yang, V. X. D., M. L. Gordon, et al. (2003). "High speed, wide velocity dynamic range Doppler optical coherence tomography (Part I): System design, signal processing, and performance." *Optics Express* 11(7): 794-809.

Yang, V. X. D., M. L. Gordon, et al. (2003). "High speed, wide velocity dynamic range Doppler optical coherence tomography (Part II): Imaging in vivo cardiac dynamics of *Xenopus laevis*." *Optics Express* 11(14): 1650-1658.

Yang, V. X. D., M. L. Gordon, et al. (2003). "High speed, wide velocity dynamic range Doppler optical coherence tomography (Part III): in vivo endoscopic imaging of blood flow in the rat and human gastrointestinal tracts." *Optics Express* 11(19): 2416-2424.

Yang, V. X. D., B. Qi, et al. (2003). "In vivo feasibility of endoscopic catheter-based Doppler optical coherence tomography." *Gastroenterology* 124(4): A49-A50.

Yao, G. and L. H. V. Wang (2000). "Theoretical and experimental studies of ultrasound-modulated optical tomography in biological tissue." *Applied Optics* 39(4): 659-664.

Yazdanfar, S. and J. A. Izatt (2002). "Self-referenced Doppler optical coherence tomography." *Optics Letters* 27(23): 2085-2087.

Yazdanfar, S., M. D. Kulkarni, et al. (1997). "High resolution imaging of in vivo cardiac dynamics using color Doppler optical coherence tomography." *Optics Express* 1 (13): 424-431.

Yazdanfar, S., A. M. Rollins, et al. (2000). "Imaging and velocimetry of the human retinal circulation with color Doppler optical coherence tomography." *Optics Letters* 25(19): 1448-1450.

Yazdanfar, S., A. M. Rollins, et al. (2000). "Noninvasive imaging and velocimetry of human retinal blood flow using color Doppler optical coherence tomography." *Investigative Ophthalmology & Visual Science* 41(4): S548-S548.

Yazdanfar, S., A. M. Rollins, et al. (2003). "In vivo imaging of human retinal flow dynamics by color Doppler optical coherence tomography." *Archives of Ophthalmology* 121(2): 235-239.

Yazdanfar, S., C. H. Yang, et al. (2005). "Frequency estimation precision in Doppler optical coherence tomography using the Cramer-Rao lower bound." *Optics Express* 13(2): 410-416.

Yun, S. H., C. Boudoux, et al. (2004). "Extended-cavity semiconductor wavelength-swept laser for biomedical imaging." *Ieee Photonics Technology Letters* 16(1): 293-295.

Yun, S. H., C. Boudoux, et al. (2003). "High-speed wavelength-swept semiconductor laser with a polygon-scanner-based wavelength filter." *Optics Letters* 28(20): 1981-1983.

Yun, S. H., G. J. Tearney, et al. (2004). "Pulsed-source and swept-source spectral-domain optical coherence tomography with reduced motion artifacts." *Optics Express* 12(23): 5614-5624.

Yun, S. H., G. J. Tearney, et al. (2004). "Removing the depth-degeneracy in optical frequency domain imaging with frequency shifting." *Optics Express* 12(20): 4822-4828.

Yun, S. H., G. J. Tearney, et al. (2004). "Motion artifacts in optical coherence tomography with frequency-domain ranging." *Optics Express* 12(13): 2977-2998.

Zhang, J., J. S. Nelson, et al. (2005). "Removal of a mirror image and enhancement of the signal-to-noise ratio in Fourier-domain optical coherence tomography using an electro-optic phase modulator." *Optics Letters* 30(2): 147-149.

Zhang, Y., M. Sato, et al. (2001). "Numerical investigations of optimal synthesis of several low coherence sources for resolution improvement." *Optics Communications* 192(3-6): 183-192.

Zhang, Y., M. Sato, et al. (2001). "Resolution improvement in optical coherence tomography by optimal synthesis of light-emitting diodes." *Optics Letters* 26(4): 205-207.

Zhao, Y., Z. Chen, et al. (2002). "Real-time phase-resolved functional optical coherence tomography by use of optical Hilbert transformation." *Optics Letters* 27(2): 98-100.

Zhao, Y. H., Z. P. Chen, et al. (2000). "Doppler standard deviation imaging for clinical monitoring of in vivo human skin blood flow." *Optics Letters* 25(18): 1358-1360.

Zhao, Y. H., Z. P. Chen, et al. (2000). "Phase-resolved optical coherence tomography and optical Doppler tomography for imaging blood flow in human skin with fast scanning speed and high velocity sensitivity." *Optics Letters* 25(2): 114-116.

Zhou, D., P. R. Prucnal, et al. (1998). "A widely tunable narrow linewidth semiconductor fiber ring laser." *IEEE Photonics Technology Letters* 10(6): 781-783.

Zuluaga, A. F. and R. Richards-Kortum (1999). "Spatially resolved spectral interferometry for determination of subsurface structure." *Optics Letters* 24(8): 519-521.

Zvyagin, A. V., J. B. FitzGerald, et al. (2000). "Real-time detection technique for Doppler optical coherence tomography." *Optics Letters* 25(22): 1645-1647.

Marc Nikles et al., "Brillouin gain spectrum characterization in single-mode optical fibers", *Journal of Lightwave Technology* 1997, 15 (10): 1842-1851.

Tsuyoshi Sonehara et al., "Forced Brillouin Spectroscopy Using Frequency-Tunable Continuous-Wave Lasers", *Physical Review Letters* 1995, 75 (23): 4234-4237.

Hajime Tanaka et al., "New Method of Superheterodyne Light Beating Spectroscopy for Brillouin-Scattering Using Frequency-Tunable Lasers", *Physical Review Letters* 1995, 74 (9): 1609-1612.

Webb RH et al. "Confocal Scanning Laser Ophthalmoscope", *Applied Optics* 1987, 26 (8): 1492-1499.

Andreas Zumbusch et al. "Three-dimensional vibrational imaging by coherent anti-Stokes Raman scattering", *Physical Review Letters* 1999, 82 (20): 4142-4145.

Katrin Kneipp et al., "Single molecule detection using surface-enhanced Raman scattering (SERS)", *Physical Review Letters* 1997, 78 (9): 1667-1670.

K.J. Koski et al., "Brillouin imaging" *Applied Physics Letters* 87, 2005.

Boas et al., "Diffusing temporal light correlation for burn diagnosis", *SPIE*, 1999, 2979:468-477.

David J. Briers, "Speckle fluctuations and biomedical optics: implications and applications", *Optical Engineering*, 1993, 32(2):277-283.

Clark et al., "Tracking Speckle Patterns with Optical Correlation", *SPIE*, 1992, 1772:77-87.

Facchini et al., "An endoscopic system for DSPI", *Optik*, 1993, 95(1):27-30.

Hrabovsky, M., "Theory of speckle displacement and decorrelation: application in mechanics", *SPIE*, 1998, 3479:345-354.

Sean J. Kirkpatrick et al., "Micromechanical behavior of cortical bone as inferred from laser speckle data", *Journal of Biomedical Materials Research*, 1998, 39(3):373-379.

Sean J. Kirkpatrick et al., "Laser speckle microstrain measurements in vascular tissue", *SPIE*, 1999, 3598:121-129.

Loree et al., "Mechanical Properties of Model Atherosclerotic Lesion Lipid Pools", *Arteriosclerosis and Thrombosis*, 1994, 14(2):230-234.

Podbielska, H. "Interferometric Methods and Biomedical Research", *SPIE*, 1999, 2732:134-141.

Richards-Kortum et al., "Spectral diagnosis of atherosclerosis using an optical fiber laser catheter", *American Heart Journal*, 1989, 118(2):381-391.

Ruth, B. "blood flow determination by the laser speckle method", *Int J Microcirc: Clin Exp*, 1990, 9:21-45.

Shapo et al., "Intravascular strain imaging: Experiments on an Inhomogeneous Phantom", *IEEE Ultrasonics Symposium* 1996, 2:1177-1180.

Shapo et al., "Ultrasonic displacement and strain imaging of coronary arteries with a catheter array", *IEEE Ultrasonics Symposium* 1995, 2:1511-1514.

Thompson et al., "Imaging in scattering media by use of laser speckle", *Opt. Soc. Am. A.*, 1997, 14(9):2269-2277.

Thompson et al., "Diffusive media characterization with laser speckle", *Applied Optics*, 1997, 36(16):3726-3724.

Tuchin, Valery V., "Coherent Optical Techniques for the Analysis of Tissue Structure and Dynamics," *Journal of Biomedical Optics*, 1999, 4(1):106-124.

M. Wussling et al., "Laser diffraction and speckling studies in skeletal and heart muscle", *Biomed, Biochim, Acta*, 1986, 45(1/2):S 23-S 27.

T. Yoshimura et al., "Statistical properties of dynamic speckles", *J. Opt. Soc. Am A*. 1986, 3(7):1032-1054.

Zimnyakov et al., "Spatial speckle correlometry in applications to tissue structure monitoring", *Applied Optics* 1997, 36(22): 5594-5607.

Zimnyakov et al., "A study of statistical properties of partially developed speckle fields as applied to the diagnosis of structural changes in human skin", *Optics and Spectroscopy*, 1994, 76(5): 747-753.

Zimnyakov et al., "Speckle patterns polarization analysis as an approach to turbid tissue structure monitoring", *SPIE* 1999, 2981:172-180.

Ramasamy Manoharan et al., "Biochemical analysis and mapping of atherosclerotic human artery using FT-IR microspectroscopy", *Atherosclerosis*, May 1993, 181-1930.

N.V. Salunke et al., "Biomechanics of Atherosclerotic Plaque" *Critical Reviews™ in Biomedical Engineering* 1997, 25(3):243-285.

D. Fu et al., "Non-invasive quantitative reconstruction of tissue elasticity using an iterative forward approach", Phys. Med. Biol. 2000 (45): 1495-1509.

S.B. Adams Jr. et al., "The use of polarization sensitive optical coherence tomography and elastography to assess connective tissue", Optical Soc. of American Washington 2002, p. 3.

International Search Report for International Patent application No. PCT/US2005/039740 published Feb. 21, 2006.

International Written Opinion for International Patent application No. PCT/US2005/039740 published Feb. 21, 2006.

International Search Report for International Patent application No. PCT/US2005/030294 published Aug. 22, 2006.

International Written Opinion for International Patent application No. PCT/US2005/043951 published Apr. 6, 2006.

International Search Report for International Patent application No. PCT/US2005/043951 published Apr. 6, 2006.

Erdelyi et al. "Generation of diffraction-free beams for applications in optical microlithography", J. Vac. Sci. Technol. B 15 (12), Mar./Apr. 1997, pp. 287-292.

International Search Report for International Patent application No. PCT/US2005/023664 published Oct. 12, 2005.

International Written Opinion for International Patent application No. PCT/US2005/023664 published Oct. 12, 2005.

Tearney et al., "Spectrally encoded miniature endoscopy" Optical Society of America; Optical Letters vol. 27, No. 6, Mar. 15, 2002; pp. 412-414.

Yelin et al., "Double-clad Fiber for Endoscopy" Optical Society of America; Optical Letters vol. 29, No. 20, Oct. 16, 2005; pp. 2408-2410.

International Search Report for International Patent application No. PCT/US2001/049704 published Dec. 10, 2002.

International Search Report for International Patent application No. PCT/US2004/039454 published May 11, 2005.

International Written Opinion for International Patent application No. PCT/US2004/039454 published May 11, 2005.

PCT International Preliminary Report on Patentability for International Application No. PCT/US2004/038404 dated Jun. 2, 2006.

Notice of Reasons for Rejection and English translation for Japanese Patent Application No. 2002-538830 dated May 12, 2008.

Office Action dated Aug. 24, 2006 for U.S. Appl. No. 10/137,749.

Barry Cense et al., "Spectral-domain polarization-sensitive optical coherence tomography at 850nm", Coherence Domain Optical Methods and Optical Coherence Tomography in Biomedicine IX, 2005, pp. 159-162.

A. Ymeti et al., "Integration of microfluidics with a four-channel integrated optical Young interferometer immunosensor", Biosensors and Bioelectronics, Elsevier Science Publishers, 2005, pp. 1417-1421.

PCT International Search Report for Application No. PCT/US2006/018865 filed May 5, 2006.

International Written Opinion for International Patent application No. PCT/US2006/018865 filed May 5, 2006.

John M. Poneros, "Diagnosis of Barrett's esophagus using optical coherence tomography", Gastrointestinal Endoscopy clinics of North America, 14 (2004) pp. 573-588.

P.F. Escobar et al., "Diagnostic efficacy of optical coherence tomography in the management of preinvasive and invasive cancer of uterine cervix and vulva", Int. Journal of Gynecological Cancer 2004, 14, pp. 470-474.

Ko T et al., "Ultrahigh resolution in vivo versus ex vivo OCT imaging and tissue preservation", Conference on Lasers and electro-optics, 2001, pp. 252-253.

Paul M. Ripley et al., "A comparison of Artificial Intelligence techniques for spectral classification in the diagnosis of human pathologies based upon optical biopsy", Journal of Optical Society of America, 2000, pp. 217-219.

Wolfgang Drexler et al., "Ultrahigh-resolution optical coherence tomography", Journal of Biomedical Optics Spie USA, 2004, pp. 47-74.

PCT International Search Report for Application No. PCT/US2006/016677 filed Apr. 28, 2006.

International Written Opinion for International Patent application No. PCT/US2006/016677 filed Apr. 28, 2006.

Office Action dated Nov. 13, 2006 for U.S. Appl. No. 10/501,268.

Office Action dated Nov. 20, 2006 for U.S. Appl. No. 09/709,162.

PCT International Search Report and Written Opinion for Application No. PCT/US2004/023585 filed Jul. 23, 2004.

Office Action dated Dec. 6, 2006 for U.S. Appl. No. 10/997,789.

Elliott, K. H. "The use of commercial CCD cameras as linear detectors in the physics undergraduate teaching laboratory", European Journal of Physics, 1998, pp. 107-117.

Lauer, V. "New approach to optical diffraction tomography yielding a vector equation of diffraction tomography and a novel tomographic microscope", Journal of Microscopy vol. 205, Issue 2, 2002, pp. 165-176.

Yu, P. et al. "Imaging of tumor necroses using full-frame optical coherence imaging", Proceedings of SPIE vol. 4956, 2003, pp. 34-41.

Zhao, Y. et al. "Three-dimensional reconstruction of in vivo blood vessels in human skin using phase-resolved optical Doppler tomography", IEEE Journal of Selected Topics in Quantum Electronics 7.6 (2001): 931-935.

Office Action dated Dec. 18, 2006 for U.S. Appl. No. 10/501,276.

Devesa, Susan S. et al. (1998) "Changing Patterns in the Incidence of Esophegeal and Gastric Carcinoma in the United States." *American Cancer Society* vol. 83, No. 10 pp. 2049-2053.

Barr, H et al. (2005) "Endoscopic Therapy for Barrett's Oesophaugs" *Gut* vol. 54:875-884.

Johnston, Mark H.(2005) "Technology Insight: Ablative Techniques for Barrett's Esophagus—Current and Emerging Trends" www.Nature.com/clinicalpractice/gasthep.

Falk, Gary W. et al. (1997) "Surveillance of Patients with Barrett's Esophagus for Dysplasia and Cancer with Ballon Cytology" *Gastrorenterology* vol. 112, pp. 1787-1797.

Sepchler, Stuart Jon. (1997) "Barrett's Esophagus: Should We Brush off this Balloning Problem?" *Gastroenterology* vol. 112, pp. 2138-2152.

Froehly, J. et al. (2003) "Multiplexed 3D Imaging Using Wavelength Encoded Spectral Interferometry: A Proof of Principle" *Optics Communications* vol. 222, pp. 127-136.

Kubba A.K. et al. (1999) "Role of p53 Assessment in Management of Barrett's Esophagus" *Digestive Disease and Sciences* vol. 44, No. 4. pp. 659-667.

Reid, Brian J. (2001) "p53 and Neoplastic Progression in Barrett's Esophagus" *The American Journal of Gastroenterology* vol. 96, No. 5, pp. 1321-1323.

Sharma, P. et al.(2003) "Magnification Chromoendoscopy for the Detection of Intestinal Metaplasia and Dysplasia in Barrett's Oesophagus" *Gut* vol. 52, pp. 24-27.

Kuipers E.J et al. (2005) "Diagnostic and Therapeutic Endoscopy" *Journal of Surgical Oncology* vol. 92, pp. 203-209.

Georgakoudi, Irene et al. (2001) "Fluorescence, Reflectance, and Light-Scattering Spectroscopy for Evaluating Dysplasia in Patients with Barrett's Esophagus" *Gastroenterology* vol. 120, pp. 1620-1629.

Adrain, Alyn L. et al. (1997) "High-Resolution Endoluminal Sonography is a Sensitive Modality for the Identification of Barrett's Meaplasia" *Gastrointestinal Endoscopy* vol. 46, No. 2, pp. 147-151.

Canto, Marcia Irene et al (1999) "Vital Staining and Barrett's Esophagus" *Gastrointestinal Endoscopy* vol. 49, No. 3, part 2, pp. 12-16.

Evans, John A. et al. (2006) "Optical Coherence Tomography to Identify Intramucosal Carcinoma and High-Grade Dysplasia in Barrett's Esophagus" *Clinical Gastroenterology and Hepatology* vol. 4, pp. 38-3.

Poneros, John M. et al. (2001) "Diagnosis of Specialized Intestinal Metaplasia by Optical Coherence Tomography" *Gastroenterology* vol. 120, pp. 7-12.

Ho, W. Y. et al. (2005) "115 KHz Tuning Repetition Rate Ultrahigh-Speed Wavelength-Swept Semiconductor Laser" *Optics Letters* col. 30, No. 23, pp. 3159-3161.

Brown, Stanley B. et al. (2004) "The Present and Future Role of Photodynamic Therapy in Cancer Treatment" *The Lancet Oncology* vol. 5, pp. 497-508.

Boogert, Jolanda Van Den et al. (1999) "Endoscopic Ablation Therapy for Barrett's Esophagua with High-Grade Dysplasia: A Review" *The American Journal of Gastroenterology* vol. 94, No. 5, pp. 1153-1160.

Sampliner, Richard E. et al. (1996) "Reversal of Barrett's Esophagus with Acid Suppression and Multipolar Electrocoagulation: Preliminary Results" *Gastrointestinal Endoscopy* vol. 44, No. 5, pp. 532-535.

Sampliner, Richard E. (2004) "Endoscopic Ablative Therapy for Barrett's Esophagus: Current Status" *Gastrointestinal Endoscopy* vol. 59, No. 1, pp. 66-69.

Soetikno, Roy M. et al. (2003) "Endoscopic Mucosal resection" *Gastrointestinal Endoscopy* vol. 57, No. 4, pp. 567-579.

Ganz, Robert A. et al. (2004) "Complete Ablation of Esophageal Epithelium with a Balloon-based Bipolar Electrode: A Phased Evaluation in the Porcine and in the Human Esophagus" *Gastrointestinal Endoscopy* vol. 60, No. 6, pp. 1002-1010.

Pfefer, Jorje at al. (2006) "Performance of the Aer-O-Scope, A Pneumatic, Self Propelling, Self Navigating Colonoscope in Animal Experiments" *Gastrointestinal Endoscopy* vol. 63, No. 5, pp. AB223.

Overholt, Bergein F. et al. (1999) "Photodynamic Therapy for Barrett's Esophagus: Follow-Up in 100 Patients" *Gastrointestinal Endoscopy* vol. 49, No. 1, pp. 1-7.

Vogel, Alfred et al. (2003) "Mechanisms of Pulsed Laser Ablation of Biological Tissues" *American Chemical Society* vol. 103, pp. 577-644.

McKenzie, A. L. (1990) "Physics of Thermal Processes in Laser-Tissue Interaction" *Phys. Med. Biol* vol. 35, No. 9, pp. 1175-1209.

Anderson, R. Rox et al. (1983) "Selective Photothermolysis" Precise Microsurgery by Selective Absorption of Pulsed Radiation *Science* vol. 220, No. 4596, pp. 524-527.

Jacques, Steven L. (1993) "Role of Tissue Optics and Pulse Duration on Tissue Effects During High-Power Laser Irradiation" *Applied Optics* vol. 32, No. 13, pp. 2447-2454.

Nahen, Kester et al. (1999) "Investigations on Acoustic On-Line Monitoring of IR Laser Ablation of burned Skin" *Lasers in Surgery and Medicine* vol. 25, pp. 69-78.

Jerath, Maya R. et al. (1993) "Calibrated Real-Time Control of Lesion Size Based on Reflectance Images" *Applied Optics* vol. 32, No. 7, pp. 1200-1209.

Jerath, Maya R. et al (1992) "Dynamic Optical Property Changes: Implications for Reflectance Feedback Control of Photocoagulation" *Journal of Photochemical,.Photobiology. B: Biol* vol. 16, pp. 113-126.

Deckelbaum, Lawrence I. (1994) "Coronary Laser Angioplasty" *Lasers in Surgery and Medicine* vol. 14, pp. 101-110.

Kim, B.M. et al. (1998) "Optical Feedback Signal for Ultrashort Laser Pulse Ablation of Tissue" *Applied Surface Science* vol. 127-129, pp. 857-862.

Brinkman, Ralf et al. (1996) "Analysis of Cavitation Dynamics During Pulsed Laser Tissue Ablation by Optical On-Line Monitoring" *IEEE Journal of Selected Topics in Quantum Electronics* vol. 2, No. 4, pp. 826-835.

Whelan, W.M. et al. (2005) "A novel Strategy for Monitoring Laser Thermal Therapy Based on Changes in Optothermal Properties of Heated Tissues" *International Journal of Thermophysics* vol. 26., No. 1, pp. 233-241.

Thomsen, Sharon et al. (1990) "Microscopic Correlates of Macroscopic Optical Property Changes During Thermal Coagulation of Myocardium" *SPIE* vol. 1202, pp. 2-11.

Khan, Misban Huzaira et al. (2005) "Intradermally Focused Infrared Laser Pulses: Thermal Effects at Defined Tissue Depths" *Lasers in Surgery and Medicine* vol. 36, pp. 270-280.

Neumann, R.A. et al. (1991) "Enzyme Histochemical Analysis of Cell Viability After Argon Laser-Induced Coagulation Necrosis of the Skin" *Journal of the American Academy of Dermatology* vol. 25, No. 6, pp. 991-998.

Nadkarni, Seemantini K. et al (2005) "Charaterization of Atherosclerotic Plaques by Laser Speckle Imaging" *Circulation* vol. 112, pp. 885-892.

Zimnyakov, Dmitry A. et al (2002) "Speckle-Contrast Monitoring of Tissue Thermal Modification" *Applied Optics* vol. 41, No. 28, pp. 5989-5996.

Morelli, J.G., et al (1986) "Tunable Dye Laser (577 nm) Treatment of Port Wine Stains" *Lasers in Surgery and Medicine* vol. 6, pp. 94-99.

French, P.M.W. et al. (1993) "Continuous-wave Mode-Locked $Cr^{4+}$: YAG Laser" *Optics Letters* vol. 18, No. 1, pp. 39-41.

Sennaroglu, Alphan at al. (1995) "Efficient Continuous-Wave Chromium-Doped YAG Laser" *Journal of Optical Society of America* vol. 12, No. 5, pp. 930-937.

Bouma, B et al. (1994) "Hybrid Mode Locking of a Flash-Lamp-Pumped Ti: $Al_2O_3$ Laser" *Optics Letters* vol. 19, No. 22, pp. 1858-1860.

Bouma, B et al. (1995) "High Resolution Optical Coherence Tomography Imaging Using a Mode-Locked Ti: $Al_2O_3$ Laser Source" *Optics Letters* vol. 20, No. 13, pp. 1486-1488.

Fernández, Cabrera Delia et al. "Automated detection of retinal layer structures on optical coherence tomography images", *Optics Express* vol. 13, No. 25, Oct. 4, 2005, pp. 10200-10216.

Ishikawa, Hiroshi et al. "Macular Segmentation with optical coherence tomography", Investigative Ophthalmology & Visual Science, vol. 46, No. 6, Jun. 2005, pp. 2012-2017.

Hariri, Lida P. et al. "Endoscopic Optical Coherence Tomography and Laser-Induced Fluorescence Spectroscopy in a Murine Colon Cancer Model", Laser in Surgery and Medicine, vol. 38, 2006, pp. 305-313.

PCT International Search Report and Written Opinion for Application No. PCT/US2006/031905 dated May 3, 2007.

PCT International Search Report and Written Opinion for Application No. PCT/US2007/060481 dated May 23, 2007.

PCT International Search Report and Written Opinion for Application No. PCT/US2007/060717 dated May 24, 2007.

PCT International Search Report and Written Opinion for Application No. PCT/US2007/060319 dated Jun. 6, 2007.

D. Yelin et al., "Three-dimensional imaging using spectral encoding heterodyne interferometry", Optics Letters, Jul. 15, 2005, vol. 30, No. 14, pp. 1794-1796.

Akiba, Masahiro et al. "En-face optical coherence imaging for three-dimensional microscopy", SPIE, 2002, pp. 8-15.

Office Action dated Aug. 10, 2007 for U.S. Appl. No. 10/997,789.

Office Action dated Feb. 2, 2007 for U.S. Appl. No. 11/174,425.

PCT International Search Report and Written Opinion for Application No. PCT/US2007/060657 dated Aug. 13, 2007.

Lewis, Neil E. et al., (2006) "Applications of Fourier Transform Infrared Imaging Microscopy in Neurotoxicity", Annals New York Academy of Sciences, Dec. 17, 2006, vol. 820, pp. 234-246.
Joo, Chulmin et al., Spectral-domain optical coherence phase microscopy for quantitative phase-contrast imaging, Optics Letters, Aug. 15, 2005, vol. 30, No. 16, pp. 2131-2133.
Guo, Bujin et al., "Laser-based mid-infrared reflectance imaging of biological tissues", Optics Express, Jan. 12, 2004, vol. 12, No. 1, pp. 208-219.
Office Action dated Mar. 28, 2007 for U.S. Appl. No. 11/241,907.
Office Action dated May 23, 2007 for U.S. Appl. No. 10/406,751.
Office Action dated May 23, 2007 for U.S. Appl. No. 10/551,735.
PCT International Search Report and Written Opinion for Application No. PCT/US2007/061815 dated Aug. 2, 2007.
Sir Randall, John et al., "Brillouin scattering in systems of biological significance", Phil. Trans. R. Soc. Lond. A 293, 1979, pp. 341-348.
Takagi, Yasunari, "Application of a microscope to Brillouin scattering spectroscopy", Review of Scientific Instruments, No. 12, Dec. 1992, pp. 5552-5555.
Lees, S. et al., "Studies of Compact Hard Tissues and Collagen by Means of Brillouin Light Scattering", Connective Tissue Research, 1990, vol. 24, pp. 187-205.
Berovic, N. "Observation of Brillion scattering from single muscle fibers", European Biophysics Journal, 1989, vol. 17, pp. 69-74.
PCT International Search Report and Written Opinion for Application No. PCT/US2007/062465 dated Aug. 8, 2007.
Pythila John W. et al., "Rapid, depth-resolved light scattering measurements using Fourier domain, angle-resolved low coherence interferometry", Optics Society of America, 2004.
Pyhtila John W. et al., "Determining nuclear morphology using an improved angle-resolved low coherence interferometry system", Optics Express, Dec. 15, 2003, vol. 11, No. 25, pp. 3473-3484.
Desjardins A.E., et al., "Speckle reduction in OCT using massively-parallel detection and frequency-domain ranging", Optics Express, May 15, 2006, vol. 14, No. 11, pp. 4736-4745.
Nadkarni, Seemantini K., et al., "Measurement of fibrous cap thickness in atherosclerotic plaques by spatiotemporal analysis of laser speckle images", Journal of Biomedical Optics, vol. 11 Marsh/Apr. 2006, pp. 021006-1-021008.
PCT International Search Report and Written Opinion for Application No. PCT/US2007/066017 dated Aug. 30, 2007.
Yamanari M. et al., "Polarization sensitive Fourier domain optical coherence tomography with continuous polarization modulation", Proc. of SPIE, vol. 6079, 2006.
Zhang Jun et al., "Full range polarization-sensitive Fourier domain optical coherence tomography", Optics Express, Nov. 29, 2004, vol. 12, No. 24, pp. 6033-6039.
European Patent Office Search report for Application No. 01991092.6-2305 dated Jan. 12, 2006.
PCT International Search Report and Written Opinion for Application No. PCT/US2007/060670 dated Sep. 21, 2007.
J. M. Schmitt et al., (1999) "Speckle in Optical Coherence Tomography: An Overview", SPIE vol. 3726, pp. 450-461.
Office Action dated Oct. 11, 2007 for U.S. Appl. No. 11/534,095.
Office Action dated Oct. 9, 2007 for U.S. Appl. No. 09/709,162.
Notice of Allowance dated Oct. 3, 2007 for U.S. Appl. No. 11/225,840.
Siavash Yazdanfar et al., "In Vivo imaging in blood flow in human retinal vessels using color Doppler optical coherence tomography", SPIE, 1999 vol. 3598, pp. 177-184.
Office Action dated Oct. 30, 2007 for U.S. Appl. No. 11/670,069.
Tang C. L. et al., "Wide-band electro-optical tuning of semiconductor lasers", Applied Physics Letters, vol. 30, No. 2, Jan. 15, 1977, pp. 113-116.
Tang C. L. et al., "Transient effects in wavelength-modulated dye lasers", Applied Physics Letters, vol. 26, No. 9, May 1, 1975, pp. 534-537.
Telle M. John, et al., "Very rapid tuning of cw dye laser", Applied Physics Letters, vol. 26, No. 10, May 15, 1975, pp. 572-574.
Telle M. John, et al., "New method for electro-optical tuning of tunable lasers", Applied Physics Letters, vol. 24, No. 2, Jan. 15, 1974, pp. 85-87.

Schmitt M. Joseph et al. "OCT elastography: imaging microscopic deformation and strain of tissue", Optics Express, vol. 3, No. 6, Sep. 14, 1998, pp. 199-211.
M. Gualini Muddassir et al., "Recent Advancements of Optical Interferometry Applied to Medicine", IEEE Transactions on Medical Imaging, vol. 23, No. 2, Feb. 2004, pp. 205-212.
Maurice L. Roch et al. "Noninvasive Vascular Elastography: Theoretical Framework", IEEE Transactions on Medical Imaging, vol. 23, No. 2, Feb. 2004, pp. 164-180.
Kirkpatrick J. Sean et al. "Optical Assessment of Tissue Mechanical Properties", Proceedings of the SPIE—The International Society for Optical Engineering SPIE—vol. 4001, 2000, pp. 92-101.
Lisauskas B. Jennifer et al., "Investigation of Plaque Biomechanics from Intravascular Ultrasound Images using Finite Element Modeling", Proceedings of the 19$^{th}$ International Conference—IEEE Oct. 30-Nov. 2, 1997, pp. 887-888.
Parker K. J. et al., "Techniques for Elastic Imaging: A Review", IEEE Engineering in Medicine and Biology, Nov./Dec. 1996, pp. 52-59.
European Patent Office Search Report dated Nov. 20, 2007 for European Application No. 05791226.3.
Dubois Arnaud et al., "Ultrahigh-resolution OCT using white-light interference microscopy", Proceedings of SPIE, 2003, vol. 4956, pp. 14-21.
Office Action dated Jan. 3, 2008 for U.S. Appl. No. 10/997,789.
Office Action dated Dec. 21, 2007 for U.S. Appl. No. 11/264,655.
Office Action dated Dec. 18, 2007 for U.S. Appl. No. 11/288,994.
Office Action dated Jan. 10, 2008 for U.S. Appl. No. 11/435,228.
Office Action dated Jan. 10, 2008 for U.S. Appl. No. 11/410,937.
Office Action dated Jan. 11, 2008 for U.S. Appl. No. 11/445,990.
Office Action dated Feb. 4, 2008 for U.S. Appl. No. 10/861,179.
PCT International Search Report and Written Opinion for Application No. PCT/US2007/061463 dated Jan. 23, 2008.
PCT International Search Report and Written Opinion for Application No. PCT/US2007/061481 dated Mar. 17, 2008.
PCT International Search Report and Written Opinion for Application No. PCT/US2007/078254 dated Mar. 28, 2008.
Sadhwani, Ajay et al., "Determination of Teflon thickness with laser speckle I. Potential for burn depth diagnosis", Optical Society of America, 1996, vol. 35, No. 28, pp. 5727-5735.
C.J. Stewart et al., "A comparison of two laser-based methods for determination of burn scar perfusion: Laser Doppler versus laser speckle imaging", Elsevier Ltd., 2005, vol. 31, pp. 744-752.
G. J. Tearney et al., "Atherosclerotic plaque characterization by spatial and temporal speckle pattern analysis", CLEO 2001, vol. 56, pp. 307-307.
PCT International Search Report for Application No. PCT/US2007/068233 dated Feb. 21, 2008.
PCT International Search Report for Application No. PCT/US2007/060787 dated Mar. 18, 2008.
Statement under Article 19 and Reply to PCT Written Opinion for PCT International Application No. PCT/US2005/043951 dated Jun. 6, 2006.
PCT International Preliminary Report on Patentability for Application No. PCT/US2005/043951 dated Jun. 7, 2007.
R. Haggitt et al., "Barrett's Esophagus Correlation Between Mucin Histochemistry, Flow Cytometry, and Histological Diagnosis for Predicting Increased Cancer Risk," Apr. 1988, American Journal of Pathology, vol. 131, No. 1, pp. 53-61.
R.H. Hardwick et al., (1995) "c-erbB-2 Overexpression in the Dysplasia/Carcinoma Sequence of Barrett's Oesophagus," Journal of Clinical Pathology, vol. 48, No. 2, pp. 129-132.
W. Polkowski et al, (1998) Clinical Decision making in Barrett's Oesophagus can be supported by Computerized Immunoquantitation and Morphometry of Features Associated with Proliferation and Differentiation, Journal of pathology, vol. 184, pp. 161-168.
J.R. Turner et al., MN Antigen Expression in Normal Preneoplastic, and Neoplastic Esophagus: A Clinicopathological Study of a New Cancer-Associated Biomarker,: Jun. 1997, Human Pathology, vol. 28, No. 6, pp. 740-744.
D.J. Bowery et al., (1999) "Patterns of Gastritis in Patients with Gastro-Oesophageal Reflux Disease,", Gut, vol. 45, pp. 798-803.

O'Reich et al., (2000) "Expression of Oestrogen and Progesterone Receptors in Low-Grade Endometrial Stromal Sarcomas,", British Journal of Cancer, vol. 82, No. 5, pp. 1030-1034.
M.I. Canto et al., (1999) "Vital Staining and Barrett's Esophagus," Gastrointestinal Endoscopy, vol. 49, No. 3, Part 2, pp. S12-S16.
S. Jackle et al., (2000) "In Vivo Endoscopic Optical Coherence Tomography of the Human Gastrointestinal Tract-Toward Optical Biopsy," Encoscopy, vol. 32, No. 10, pp. 743-749.
E. Montgomery et al., "Reproducibility of the Diagnosis of Dysplasia in Barrett Esophagus: A Reaffirmation," Apr. 2001, Human Pathology, vol. 32, No. 4, pp. 368-378.
H. Geddert et al., "Expression of Cyclin B1 in the Metaplasia—Dysphasia—Carcinoma Sequence of Barrett Esophagus," Jan. 2002, Cancer, vol. 94, No. 1, pp. 212-218.
P. Pfau et al., (2003) "Criteria for the Diagnosis of Dysphasia by Endoscopic Optical Coherence Tomography," Gastrointestinal Endoscopy, vol. 58, No. 2, pp. 196-2002.
R. Kiesslich et al., (2004) "Confocal Laser Endoscopy for Diagnosing Intraepithelial Neoplasias and Colorectal Cancer in Vivo," Gastroenterology, vol. 127, No. 3, pp. 706-713.
X. Qi et al., (2004) "Computer Aided Diagnosis of Dysphasia in Barrett's Esophagus Using Endoscopic Optical Coherence Tomography," SPIE, Coherence Domain Optical Methods and Optical Coherence Tomography in Biomedicine VIII. Proc. of Conference on., vol. 5316, pp. 33-40.
Seltzer et al., (1991) "160 nm Continuous Tuning of a MQW Laser in an External Cavity Across the Entire 1.3 μm Communications Window," Electronics Letters, vol. 27, pp. 95-96.
Office Action dated Jan. 25, 2010 for U.S. Appl. No. 11/537,048.
International Search Report dated Jan. 27, 2010 for PCT/US2009/050553.
International Search Report dated Jan. 27, 2010 for PCT/US2009/047988.
International Search Report dated Feb. 23, 2010 for U.S. Appl. No. 11/445,131.
Office Action dated Mar. 18, 2010 of U.S. Appl. No. 11/844,454.
Office Action dated Apr. 8, 2010 of U.S. Appl. No. 11/414,564.
Japanese Office Action dated Apr. 13, 2010 for Japanese Patent application No. 2007-515029.
International Search Report dated May 27, 2010 for PCT/US2009/063420.
Office Action dated May 28, 2010 for U.S. Appl. No. 12/015,642.
Office Action dated Jun. 2, 2010 for U.S. Appl. No. 12/112,205.
Office Action dated Jul. 7, 2010 for U.S. Appl. No. 11/624,277.
Montag Ethan D., "Parts of the Eye" online textbook for JIMG 774: Vision & Psycophysics, download on Jun. 23, 2010 from http://www.cis.rit.edu/people/faculty/montag/vandplite/pages/chap_8/ch8p3.html.
Office Action dated Jul. 16, 2010 for U.S. Appl. No. 11/445,990.
Office Action dated Jul. 20, 2010 for U.S. Appl. No. 11/625,135.
Office Action dated Aug. 5, 2010 for U.S. Appl. No. 11/623,852.
Chinese office action dated Aug. 4, 2010 for CN 200780005949.9.
Chinese office action dated Aug. 4, 2010 for CN 200780016266.3.
Zhang et al., "Full Range Polarization-Sensitive Fourier Domain Optical Coherence Tomography" Optics Express, Nov. 29, 2004, vol. 12, No. 24.
Office Action dated Aug. 27, 2010 for U.S. Appl. No. 11/569,790.
Office Action dated Aug. 31, 2010 for U.S. Appl. No. 11/677,278.
Office Action dated Sep. 3, 2010 for U.S. Appl. No. 12/139,314.
Yong Zhao et al: "Virtual Data Grid Middleware Services for Data-Intensive Science", Concurrency and Computation: Practice and Experience, Wiley, London, GB, Jan. 1, 2000, pp. 1-7, pp. 1532-0626.
Swan et al., "Toward Nanometer-Scale Resolution in Fluorescence Microscopy using Spectral Self-Inteference" IEEE Journal. Selected Topics in Quantum Electronics 9 (2) 2003, pp. 294-300.
Moiseev et al., "Spectral Self-Interfence Fluorescence Microscopy", J. Appl. Phys. 96 (9) 2004, pp. 5311-5315.
Hendrik Verschueren, "Interference Reflection Microscopy in Cell Biology", J. Cell Sci. 75, 1985, pp. 289-301.
Park et al., "Diffraction Phase and Fluorescence Microscopy", Opt. Expr. 14 (18) 2006, pp. 8263-8268.

Swan et al. "High Resolution Spectral Self-Interference Fluorescence Microscopy", Proc. SPIE 4621, 2002, pp. 77-85.
Sanchez et al., "Near-Field Fluorscence Microscopy Based on Two-Photon Excvitation with Metal Tips", Phys. Rev. Lett. 82 (20) 1999, pp. 4014-4017.
Wojtkowski, Maciej, Ph.D. "Three-Dimensional Retinal Imaging with High-Speed Ultrahigh-Resolution Optical Coherence Tomography" Ophthalmology, Oct. 2005, 112(10): 1734-1746.
Vaughan, J.M. et al., "Brillouin Scattering, Density and Elastic Properties of the Lens and Cornea of the Eye", Nature, vol. 284, Apr. 3, 1980, pp. 489-491.
Hess, S.T. et al. "Ultra-high Resolution Imaging by Fluorescence Photoactivation Localization Microscopy" Biophysical Journal vol. 91, Dec. 2006, 4258-4272.
Fernandez-Suarez, M. et al., "Fluorescent Probes for Super-Resolution Imaging in Living Cells" Nature Reviews Molecular Cell Biology vol. 9, Dec. 2008.
Extended European Search Report mailed Dec. 14, 2010 for EP 10182301.1.
S. Hell et al., "Breaking the diffraction resolution limit by stimulated-emission—stimulated-emission-depletion fluorescence microscopy," Optics Letters. 19:495 (1995) and Ground State Depletion (GSD).
S. Hell et al. "Ground-State-Depletion fluorescence microscopy—a concept for breaking the diffraction resolution limit," Applied Physics B. 60:780 (1994)) fluorescence microscopy, photo-activated localization microscopy (PALM).
E. Betzig et al. "Imaging intracellular fluorescent proteins at nanometer resolution," Science 313:1642 (2006), stochastic optical reconstruction microscopy (STORM).
M. Rust et al. "Sub-diffraction-limited imaging by stochastic optical reconstruction microscopy (STORM)," Nature Methods 3:783 (2006), and structured illumination microscopy (SIM).
B. Bailey et al. "Enhancement of Axial Resolution in Fluorescence Microscopy by Standing-Wave Excitation," Nature 366:44 (1993).
M. Gustafsson "Surpassing the lateral resolution limit by a factor of two using structured illumination microscopy," Journal of Microscopy 198:82 (2000).
M. Gustafsson "Nonlinear structured illumination microscopy: Wide-field fluorescence imaging with theoretically unlimited resolution," PNAS 102:13081 (2005)).
R. Thompson et al. "Precise nanometer localization analysis for individual fluorescent probes," Biophysical Journal 82:2775 (2002).
K. Drabe et al. "Localization of Spontaneous Emission in front of a mirror," Optics Communications 73:91 (1989).
Swan et al. "Toward nanometer-scale resolution in fluorescence microscopy using spectral self-interference," IEEE Quantum Electronics 9:294 (2003).
C. Joo, et al. "Spectral Domain optical coherence phase and multiphoton microscopy," Optics Letters 32:623 (2007).
Liptak David C. et al., (2007) "On the Development of a Confocal Rayleigh-Brillouin Microscope" *American Institute of Physics* vol. 78, 016106.
Office Action mailed Oct. 1, 2008 for U.S. Appl. No. 11/955,986.
Invitation of Pay Additional Fees mailed Aug. 7, 2008 for International Application No. PCT/US2008/062354.
Invitation of Pay Additional Fees mailed Jul. 20, 2008 for International Application No. PCT/US2007/081982.
International Search Report and Written Opinion mailed Mar. 7, 2006 for PCT/US2005/035711.
International Search Report and Written Opinion mailed Jul. 18, 2008 for PCT/US2008/057533.
Aizu, Y et al. (1991) "Bio-Speckle Phenomena and Their Application to the Evaluation of Blood Flow" Optics and Laser Technology, vol. 23, No. 4, Aug. 1, 1991.
Richards G.J. et al. (1997) "Laser Speckle Contrast Analysis (LASCA): A Technique for Measuring Capillary Blood Flow Using the First Order Statistics of Laser Speckle Patterns" Apr. 2, 1997.
Gonick, Maria M., et al (2002) "Visualization of Blood Microcirculation Parameters in Human Tissues by Time Integrated Dynamic Speckles Analysis" vol. 972, No. 1, Oct. 1, 2002.
International Search Report and Written Opinion mailed Jul. 4, 2008 for PCT/US2008/051432.

Jonathan, Enock (2005) "Dual Reference Arm Low-Coherence Interferometer-Based Reflectometer for Optical Coherence Tomography (OCT) Application" *Optics Communications* vol. 252.
Motaghian Nezam, S.M.R. (2007) "increased Ranging Depth in optical Frequency Domain Imaging by Frequency Encoding" *Optics Letters*, vol. 32, No. 19, Oct. 1, 2007.
Office Action dated Jun. 30, 2008 for U.S. Appl. No. 11/670,058.
Office Action dated Jul. 7, 2008 for U.S. Appl. No. 10/551,735.
Australian Examiner's Report mailed May 27, 2008 for Australian patent application No. 2003210669.
Notice of Allowance mailed Jun. 4, 2008 for U.S. Appl. No. 11/174,425.
European communication dated May 15, 2008 for European patent application No. 05819917.5.
International Search Report and Written Opinion mailed Jun. 10, 2008 for PCT/US2008/051335.
Oh. W.Y. et al (2006) "Ultrahigh-Speed Optical Frequency Domain Imaging and Application to laser Ablation Monitoring" *Applied Physics Letters*, vol. 88.
Office Action dated Aug. 21, 2008 for U.S. Appl. No. 11/505,700.
Sticker, Markus (2002) En Face Imaging of Single Cell layers by Differential Phase-Contrast Optical Coherence Microscopy) *Optics Letters*, col. 27, No. 13, Jul. 1, 2002.
International Search Report and Written Opinion dated Jul. 17, 2008 for International Application No. PCT/US2008/057450.
International Search Report and Written Opinion dated Aug. 11, 2008 for International Application No. PCT/US2008/058703.
US National Library of Medicine (NLM), Bethesda, MD, US; Oct. 2007, "Abstracts of the 19$^{th}$ Annual Symposium of Transcatheter Cardiovascular Therapeutics, Oct. 20-25, 2007, Washington, DC, USA."
International Search Report and Written Opinion dated May 26, 2008 for International Application No. PCT/US2008/051404.
Office Action dated Aug. 25, 2008 for U.S. Appl. No. 11/264,655.
Office Action dated Sep. 11, 2008 for U.S. Appl. No. 11/624,334.
Office Action dated Aug. 21, 2008 for U.S. Appl. No. 11/956,079.
Gelikono, V. M. et al. Oct. 1, 2004 "Two-Wavelength Optical Coherence Tomography" Radio physics and Quantum Electronics, Kluwer Academic Publishers-Consultants. vol. 47, No. 10-1.
International Search Report and Written Opinion for PCT/US2007/081982 dated Oct. 19, 2007.
Database Compendex Engineering Information, Inc., New York, NY, US; Mar. 5, 2007, Yelin, Dvir et al: "Spectral-Domain Spectrally-Encoded Endoscopy".
Database Biosis Biosciences Information Service, Philadelphia, PA, US; Oct. 2006, Yelin D. et al: "Three-Dimensional Miniature Endoscopy".
International Search Report and Written Opinion mailed Mar. 14, 2005 for PCT/US2004/018045.
Notification of the international Preliminary Report on Patentability mailed Oct. 21, 2005.
Shim M.G. et al., "Study of Fiber-Optic Probes for In vivo Medical Raman Spectroscopy" Applied Spectroscopy. vol. 53, No. 6, Jun. 1999.
Bingid U. et al., "Fibre-Optic Laser-Assisted Infrared Tumour Diagnostics (FLAIR); Infrared Tomour Diagnostics" Journal of Physics D. Applied Physics, vol. 38, No. 15, Aug. 7, 2005.
Jun Zhang et al. "Full Range Polarization-Sensitive Fourier Domain Optical Coherence Tomography" Optics Express, vol. 12, No. 24. Nov. 29, 2004.
Yonghua et al., "Real-Time Phase-Resolved Functional Optical Hilbert Transformation" Optics Letters, vol. 27, No. 2, Jan. 15, 2002.
Siavash et al., "Self-Referenced Doppler Optical Coherence Tomography" Optics Letters, vol. 27, No. 23, Dec. 1, 2002.
International Search Report and Written Opinion dated Dec. 20, 2004 for PCT/US04/10152.
Notification Concerning Transmittal of International Preliminary Report on Patentability dated Oct. 13, 2005 for PCT/US04/10152.
International Search Report and Written Opinion dated Mar. 23, 2006 for PCT/US2005/042408.
International Preliminary Report on Patentability dated Jun. 7, 2007 for PCT/US2005/042408.
International Search Report and Written Opinion dated Feb. 28, 2007 for International Application No. PCT/US2006/038277.
International Search Report and Written Opinion dated Jan. 30, 2009 for International Application No. PCT/US2008/081834.
Fox, J.A. et al; "A New Galvanometric Scanner for Rapid tuning of C02 Lasers" New York, IEEE, US vol. Apr. 7, 1991.
Motaghian Nezam, S.M. et al: "High-speed Wavelength-Swept Semiconductor laser using a Diffrection Grating and a Polygon Scanner in Littro Configuration" *Optical Fiber Communication and the National Fiber Optic Engineers Conference* Mar. 29, 2007.
International Search Report and Written Opinion dated Feb. 2, 2009 for International Application No. PCT/US2008/071786.
Bilenca A et al: "The Role of Amplitude and phase in Fluorescence Coherence Imaging: From Wide Filed to Nanometer Depth Profiling", *Optics IEEE*, May 5, 2007.
Inoue, Yusuke et al: "Varible Phase-Contrast Fluorescence Spectrometry for Fluorescently Strained Cells", *Applied Physics Letters*, Sep. 18, 2006.
Bernet, S et al: "Quantitative Imaging of Complex Samples by Spiral Phase Contrast Microscopy", *Optics Express*, May 9, 2006.
International Search Report and Written Opinion dated Jan. 15, 2009 for International Application No. PCT/US2008/074863.
Office Action dated Feb. 17, 2009 for U.S. Appl. No. 11/211,483.
Notice of Reasons for Rejection mailed Dec. 2, 2008 for Japanese patent application No. 2000-533782.
International Search Report and Written Opinion dated Feb. 24, 2009 for PCT/US2008/076447.
European Official Action dated Dec. 2, 2008 for EP 07718117.0.
Barfuss et al (1989) "Modified Optical Frequency Domain Reflectometry with High spatial Resolution for Components of integrated optic Systems", Journal of Lightwave Technology, IEEE vol. 7., No. 1.
Yun et al., (2004) "Removing the Depth-Degeneracy in Optical Frequency Domain Imaging with Frequency Shifting", Optics Express, vol. 12, No. 20.
International Search Report and Written Opinion dated Jun. 10, 2009 for PCT/US08/075456.
European Search Report issued May 5, 2009 for European Application No. 01991471.2.
Motz, J.T. et al: "Spectral-and Frequency-Encoded Fluorescence Imaging" Optics Letters, OSA, Optical Society of America, Washington, DC, US, vol. 30, No. 20, Oct. 15, 2005, pp. 2760-2762.
Japanese Notice of Reasons for Rejection dated Jul. 14, 2009 for Japanese Patent application No. 2006-503161.
Office Action dated Aug. 18, 2009 for U.S. Appl. No. 12/277,178.
Office Action dated Aug. 13, 2009 for U.S. Appl. No. 10/136,813.
Office Action dated Aug. 6, 2009 for U.S. Appl. No. 11/624,455.
Office Action dated May 15, 2009 for U.S. Appl. No. 11/537,123.
Office Action dated Apr. 17, 2009 for U.S. Appl. No. 11/537,343.
Office Action dated Apr. 15, 2009 for U.S. Appl. No. 12/205,775.
Office Action dated Dec. 9, 2008 for U.S. Appl. No. 09/709,162.
Office Action dated Dec. 23, 2008 for U.S. Appl. No. 11/780,261.
Office Action dated Jan. 9, 2010 for U.S. Appl. No. 11/624,455.
Office Action dated Feb. 18, 2009 for U.S. Appl. No. 11/285,301.
Beddow et al, (May 2002) "Improved Performance Interferomater Designs for Optical Coherence Tomography", IEEE Optical Fiber Sensors Conference, pp. 527-530.
Yaqoob et al., (Jun. 2002) "High-Speed Wavelength-Multiplexed Fiber-Optic Sensors for Biomedicine," Sensors Proceedings of the IEEE, pp. 325-330.
Office Action dated Feb. 18, 2009 for U.S. Appl. No. 11/697,012.
Zhang et al, (Sep. 2004), "Fourier Domain Functional Optical Coherence Tomography", Saratov Fall Meeting 2004, pp. 8-14.
Office Action dated Feb. 23, 2009 for U.S. Appl. No. 11/956,129.
Office Action dated Mar. 16, 2009 for U.S. Appl. No. 11/621,694.
Office Action dated Oct. 1, 2009 for U.S. Appl. No. 11/677,278.
Office Action dated Oct. 6, 2009 for U.S. Appl. No. 12/015,642.
Lin, Stollen et al., (1977) "A CW Tunable Near-infrared (1.085-1.175-um) Raman Oscillator," Optics Letters, vol. 1, 96.
Summons to attend Oral Proceedings dated Oct. 9, 2009 for European patent application No. 06813365.1.
Office Action dated Dec. 15, 2009 for U.S. Appl. No. 11/549,397.

\* cited by examiner

SPECKLE REDUCTION IN OPTICAL COHERENCE TOMOGRAPHY BY PATH LENGTH ENCODED ANGULAR COMPOUNDING

CROSS REFERENCE TO RELATED APPLICATIONS

The present application is a continuation of U.S. patent application Ser. No. 10/551,735 filed Sep. 29, 2005, now U.S. Pat. No. 7,567,349. This application also claims priority from U.S. provisional application No. 60/514,769 filed on Oct. 23, 2003, International Application No PCT/US03/02349 filed on Jan. 24, 2003, and U.S. Application Ser. Nos. 60/476,600 and 60/514,769, filed on Jun. 6, 2003 and Oct. 27, 2003. Thus, the entire disclosures of these application are incorporated herein by reference.

FIELD OF THE INVENTION

The present invention relates to optical imaging methods and apparatus useful in medical diagnosis and imaging. In particular, the present invention relates to a high speed method for implementing angular compounding, e.g., angular compounding by path length encoding ("ACPE") for reducing speckle in optical coherence tomography images.

BACKGROUND INFORMATION

Optical coherence tomography ("OCT") is a technique for obtaining high resolution cross-sectional images of biological tissues. Clinical OCT studies conducted in the gastrointestinal tract and cardiovascular system have shown that OCT is capable of providing images of the architectural (>20 µm) microanatomy of a variety of epithelial tissues, including the layered structure of squamous epithelium and arterial vessels. However, for certain medical applications, such as the early detection of high-grade dysplasia in Barrett's esophagus and the identification of inflammation within atherosclerotic plaques, visualization of structures that are on a size scale of <20 µm may be preferable. OCT systems, with typical axial resolutions ranging from 8-12 µm, have the potential to resolve many of these structures, including nuclei, individual glands, and macrophages. Unfortunately, speckle, which occurs on the same size scale as these features, may prohibit unambiguous including nuclei, individual glands, and macrophages. Unfortunately, speckle, which occurs on the same size scale as these features, may prohibit unambiguous identification of the cellular and subcellular tissue components required for widespread clinical utilization of such technology.

Catheter or endoscope access and high-speed imaging is used in order to perform OCT in the internal organs of patients. In order to minimize diameter, most catheter-based OCT probes employ a single optical fiber to illuminate the sample and detect the signal from the tissue. High frame rates (typically 4-10 frames per second) are preferred for performing OCT imaging while minimizing artifacts caused by patient motion. A way to reduce speckle in OCT images that does not significantly increase the complexity of single optical fiber probe designs while maintaining high frame rates may be beneficial for applying OCT to accurately detect and quantify key microscopic tissue structures in patients.

The reduction of speckle in the OCT images speckle has been previously described. A publication by J. M. Schmitt, "Array Detection for Speckle Reduction in Optical Coherence Microscopy," Phys. Med. Biol. 42, 1427-1429, 1997, the entire disclosure of which is incorporated herein by reference, describes a procedure for a speckle reduction by averaging multiple images acquired at different angles, known as angular compounding. In this publication, multiple (N) detectors receive images that have been acquired from different angles. The images are averaged incoherently, providing an improvement ($\sqrt{N}$) in the signal to noise ratio ("SNR"). While this technique has the advantage that the measurements may be performed in real-time, the experimental apparatus as described therein would not be compatible with a single fiber optic catheter.

Another publication, M. Bashkansky and J. Reintjes, "Statistics and reduction of Speckle in Optical Coherence Tomography," Opt. Lett. 25, 545-547, 2000, the entire disclosure of which is incorporated herein by reference, describes an alternative technique for angular compounding to reduce speckle. In this method, a retroreflector apparatus is translated in front of the objective lens to change the angle of the incident beam on the tissue. N successive images are acquired and added incoherently to reduce speckle, again improving the SNR by a factor of $\sqrt{N}$. While this method may be less complex than the use of multiple detectors, the time needed thereby to acquire the images is increased by N. In addition, the implementation of this method within the confines of a small diameter catheter or endoscope could be difficult.

SUMMARY OF THE INVENTION

According to one exemplary embodiment of the present invention, a method for performing angular compounding to reduce speckle within OCT images is provided, which may use angular compounding by path length encoding ("ACPE"). With ACPE, a high-speed acquisition can be maintained, and modifications to standard OCT catheter optics are likely to be minimal. In another exemplary embodiment according to the present invention, an apparatus for imaging is provided that uses ACPE.

Accordingly, apparatus probe catheter, and method according to exemplary embodiments of the present invention are provided for irradiating a sample. In particular, an interferometer may forward forwarding an electromagnetic radiation. in addition, a sample arm may receive the electromagnetic radiation, and can include an arrangement which facilitates a production of at least two radiations from the electromagnetic radiation so as to irradiate the sample. Such arrangement can be configured to delay a first radiation of the at least two radiations with respect to a second radiation of the at least two radiations.

According to another exemplary embodiment of the present invention, a reference arm provides a further electromagnetic radiation. In particular, the interferometer receives the first, second and further radiations, and forms a resultant signal based on the first, second and further radiations. A processing arrangement may also be provided for generating a first image based on the first radiation and a second image based on the second radiation, such that the first and second images are different from one another. The further image may be generated based on the first and second images. In addition, the further image may have a noise that is smaller than a noise of the first image and a noise of the second image. Also, the further image may have a signal to noise ratio that is improved according to the equation:

$$SNR_{ACPE} = \frac{\langle S_{OCT} \rangle}{\sqrt{\text{var}[S_{OCT}]}} \propto \frac{\sum_{i=1}^{N} u_i}{\sqrt{\sum_{i=1}^{N} u_i^2}},$$

where SNRACPE is the signal to noise ratio, SOCT is an amplitude of a high-pass filtered OCT signal, m is a thickness of the arrangement, ui is an amplitude of a demodulated OCT signal at a spatial location, and N===2m−1. Further, m=2 and N=3 images associated with the at least two radiations may be obtained. The further image may also be generated based on a mathematical combination of the first and second images.

According to yet another exemplary embodiment of the present invention, the sample can be irradiated by the first irradiation at a first angle, and by the second radiation at a second angle, such that the first and second angles different from one another. For example, the first and second angle may be different from one another based on the delay and at least one of a phase and a incident angle of each of the first and second radiations. It is also possible to utilize a detector which detects the first electromagnetic energy, and forwards the detected energy to the processing arrangement.

In still another exemplary embodiment of the present invention, the arrangement can include two sections, each being configured to delay a respective one of the first and second radiations. In particular, a delay of the first radiation is preferably greater than a delay of the second radiation. In addition, the delay of a path of the first radiation compared to a path of the second radiation is at least 500 µm in air. Further, the delay of a path of the first radiation compared to a path of the second radiation is at least 1 mm in air. The arrangement may have a refractive index of at least 1.5 or at least 3.0. The arrangement can include silicon and/or an anti-reflective coating on at least one surface thereof. Such arrangement can be an anti-reflection-coated BK 7 glass. The glass may have a thickness of from about 1.6 mm to about 7.7 mm, and a refractive index of from about 1.51 to about 3.5.

According to yet another exemplary embodiment of the present invention, an apparatus for imaging is provided. The apparatus includes a sample arm that receive an electromagnetic radiation. The sample arm includes an arrangement which facilitates a production of at least two radiations from the electromagnetic radiation so as to irradiate a sample. The arrangement is configured to delay a first radiation of the at least two radiations with respect to a second radiation of the at least two radiations. The apparatus also includes a device for receiving the first and second radiations from the sample arm and at least one third radiation from a reference arm, such that the first and second radiations interfere with the third radiation. Further, the apparatus includes at least one of spectral separating unit which separates spectrum of at least one of the first, second and third radiations into frequency components, and at least one detection arrangement including a plurality of detectors. Each detector is capable of detecting at least a portion of at least one of the frequency components.

In a further exemplary embodiment of the present invention, an apparatus is provided. Such apparatus includes at least one first arrangement that provides at least one first electro-magnetic radiation to a sample arm and at least one second electro-magnetic radiation to a non-reflective reference arm. A frequency of radiation provided by the first arrangement varies over time. The sample arm receives the first electromagnetic radiation, and includes an arrangement which facilitates a production of at least two radiations from the electromagnetic radiation so as to irradiate a sample. The arrangement is configured to delay a first radiation of the at least two radiations with respect to a second radiation of the at least two radiations. The apparatus also includes at least one second arrangement detecting an interference between the first and second radiations generated at the sample arm and the second electro-magnetic radiations generated at the reference.

In still another exemplary embodiment of the present invention, an apparatus is provided. The apparatus includes a. at least one first arrangement providing at least one first electro-magnetic radiation to a sample arm and at least one second electro-magnetic radiation to a reference arm. The first and/or second electro-magnetic radiation have a spectrum which changes over time. The spectrum contains multiple frequencies at a particular time. The sample arm receives the first electromagnetic radiation, and includes an arrangement which facilitates a production of at least two radiations from the electromagnetic radiation so as to irradiate a sample. The arrangement is configured to delay a first radiation of the at least two radiations with respect to a second radiation of the at least two radiations. The apparatus also includes at least one second arrangement detecting an interference between the first and second radiations generated at the sample arm and the second electro-magnetic radiations generated at the reference.

Other features and advantages of the present invention will become apparent upon reading the following detailed description of embodiments of the invention, when taken in conjunction with the appended claims.

BRIEF DESCRIPTION OF THE DRAWINGS

The invention is illustrated in the drawings in which like reference characters designate the same or similar parts throughout the figures of which.

RETAILED DESCRIPTION

I. Materials and Methods

Figure 1:
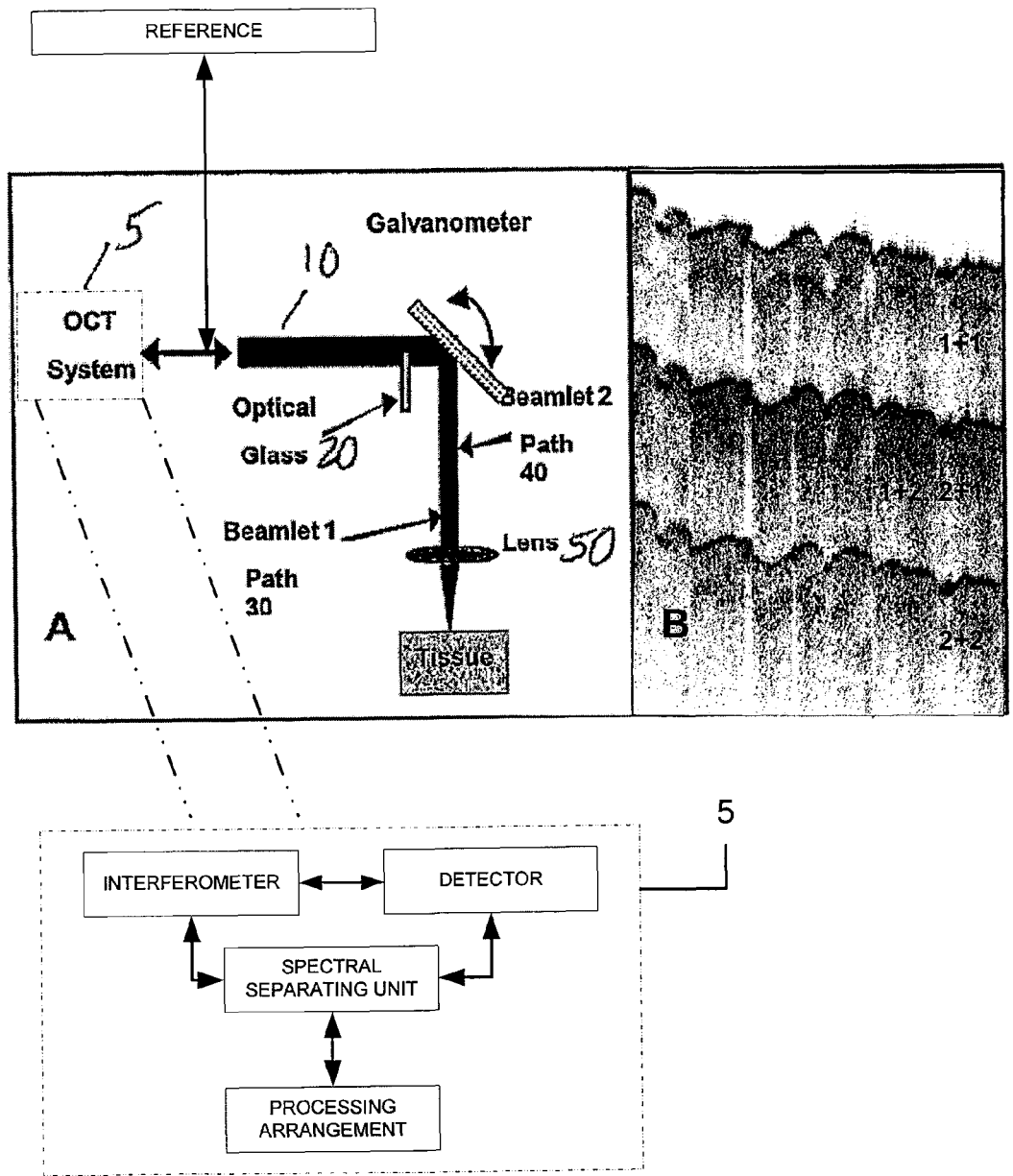
FIG. 1A is a schematic diagram of an exemplary embodiment of an ACPE-OCT apparatus according to the present invention.
FIG. 1B is a black diagram of an exemplary OCT system shown in FIG. 2D.

FIG. 1A shows an exemplary embodiment of an apparatus according to the present invention which uses ACPE. An optical glass 20 is placed in an imaging path 10 of a conventional OCT imaging apparatus 5, splitting the incident field into two beamlets 1 and 2 which are provided on beam paths 30 and 40, respectively. For the purpose of the present discussion, a beamlet can be defined as a portion of a beam. An optical element (e.g., the optical glass 20) causes a portion of the incident beam (beamlet 2) to experience a greater path length delay than beamlet 1. In addition, beamlet 2 illuminates the sample at a different angle than beamlet 1. A lens may be provided to converge the beamlets 1 and 2 onto the sample (e.g., a tissue). As a result, multiple OCT images of a specimen in or on the sample, each acquired at a different angle, can appear simultaneously on the OCT display (see FIG. 1B). In particular, FIG. 1B shows that the top image (i.e., labeled as 1+1) corresponds to the image formed from path 1 (i.e., incident and reflected), the middle image (i.e., labeled as 1+2, 2+1) corresponds to the image formed from path 1 incident, path 2 reflected and path 2 incident, path 1 reflected. Further, the bottom image (i.e., 2+2) of FIG. 1B corresponds to the image formed from path 2 (incident and reflected).

These beamlets 1 and 2, thus encoded by optical path length, also illuminate the sample at different angles. As a result, multiple OCT images, each acquired at different angles, are preferably present in a single OCT frame (as shown in FIG. 1B). For example, when the optical element contains in distinct thicknesses of glass, with each optical thickness a multiple of the others, 2m−1 OCT images can be obtained in one OCT frame. Each image may be separated by a group delay of D(n−1)/2, where D is the thickness and n is the refractive index of the optical material. The distinct OCT images are then averaged to produce a composite OCT image with significantly reduced speckle. Since all of the images are acquired in one OCT frame, single frame acquisition time can be maintained. In addition, the modifications to the OCT probe may involve only the insertion of at least one small optical element in the beam path of the distal optics. These advantages of ACPE allow speckle averaging to be performed within the confines of a small diameter catheter or endoscope, and without compromising the acquisition speed.

Previous attempts of utilizing OCT speckle reduction by image compounding has shown that the addition of N images of the same intensity provides an SNR increase by a factor of $\sqrt{N}$. For example, the Bashkansky publication described above describes that the speckle distribution in OCT takes the form of the probability density function:

$$p(S_{OCT}) = \frac{1}{\sqrt{2\pi\kappa}} \exp\left(\frac{-S_{OCT}^2}{2\kappa^2}\right) \quad (1)$$

where $\kappa=2A_R\sigma$, with $A_R$ is the amplitude of the reference field, $S_{OCT}$ is the amplitude of the high-pass filtered OCT signal, and axis its standard deviation. For this probability density function, it can be demonstrated that the SNR improvement obtained by averaging N images of the same amplitude is also a factor of $\sqrt{N}$, a result that has been experimentally described in the Schmitt and Bashkansky publications. For ACPE, the distinct OCT subimages generally may not have equal amplitudes. However, with the assumption of isotropic backscattering, these subimages are related to the original OCT image, $S0_{OCT}$, by $\beta/m^2$, where $\beta$ is the number of path length combinations that contribute to a distinct subimage. As a result, the SNR for ACPE may be defined as $$SNR_{ACPE} = \frac{\langle S_{OCT}\rangle}{\sqrt{\mathrm{var}[S_{OCT}]}} \propto \frac{\sum_{i=1}^{N} u_i}{\sqrt{\sum_{i=1}^{N} u_i^2}}, \quad (2)$$

where $u_i$ is the amplitude of the demodulated OCT signal at a spatial location, and N=2m−1. In the case of m=2, N=3 images are obtained and the relationships between the amplitudes of the ACPE OCT subimages are $S1_{OCT}=S3_{OCT}=\frac{1}{4}S0_{OCT}$ and $S2_{OCT}=2S1_{OCT}=\frac{1}{2}S0_{OCT}$. The potential SNR improvement of the compounded m=2 ACPE image can then become $SNR_{ACPE}/SNR_0=1.63$, where $SNR_0$ is the signal to noise ratio of $S0_{OCT}$.

EXAMPLES

II. Example 1

An exemplary polarization-diverse OCT system according to the present invention can be utilized for the examplary apparatus (e.g., as shown in FIG. 1A) that implements ACPE. Using such exemplary system according to the present invention, OCT images may be acquired at 2 frames per second (e.g., 500 axial pixels×500 transverse pixels), which may be displayed with an inverse gray-scale lookup table, and digitally archived. The optical source which can be used in such exemplary OCT system may have a center wavelength of 1310 nm and a bandwidth of 70 nm, and thus providing an axial resolution of approximately 8 μm in the tissue.

A modified hand-held galvanometer probe (e.g., the apparatus of FIG. 1A) can be inserted in the sample arm of the OCT system 5. The objective lens 50 may have a focal length of 25 mm and a numerical aperture (NA) of 0.11, providing a measured $1/e_2$ focal spot diameter of 23 μm. A square, anti-reflection-coated D=3.1 mm BK7 glass (n=1.51) (e.g., the optical glass 20, may be inserted between the optical fiber collimator and the objective lens 50 (see FIG. 1A) so that overlaps with half of the illuminating beam. With this exemplary configuration, an OCT image separation of approximately 800 [tm can be achieved. When the glass plate is inserted, the spot diameter perpendicular to the glass edge may increase by a factor of two (46 μm). In the plane of the OCT image, however, the transverse resolution is likely preserved.

III. Example 2

Figure 2:
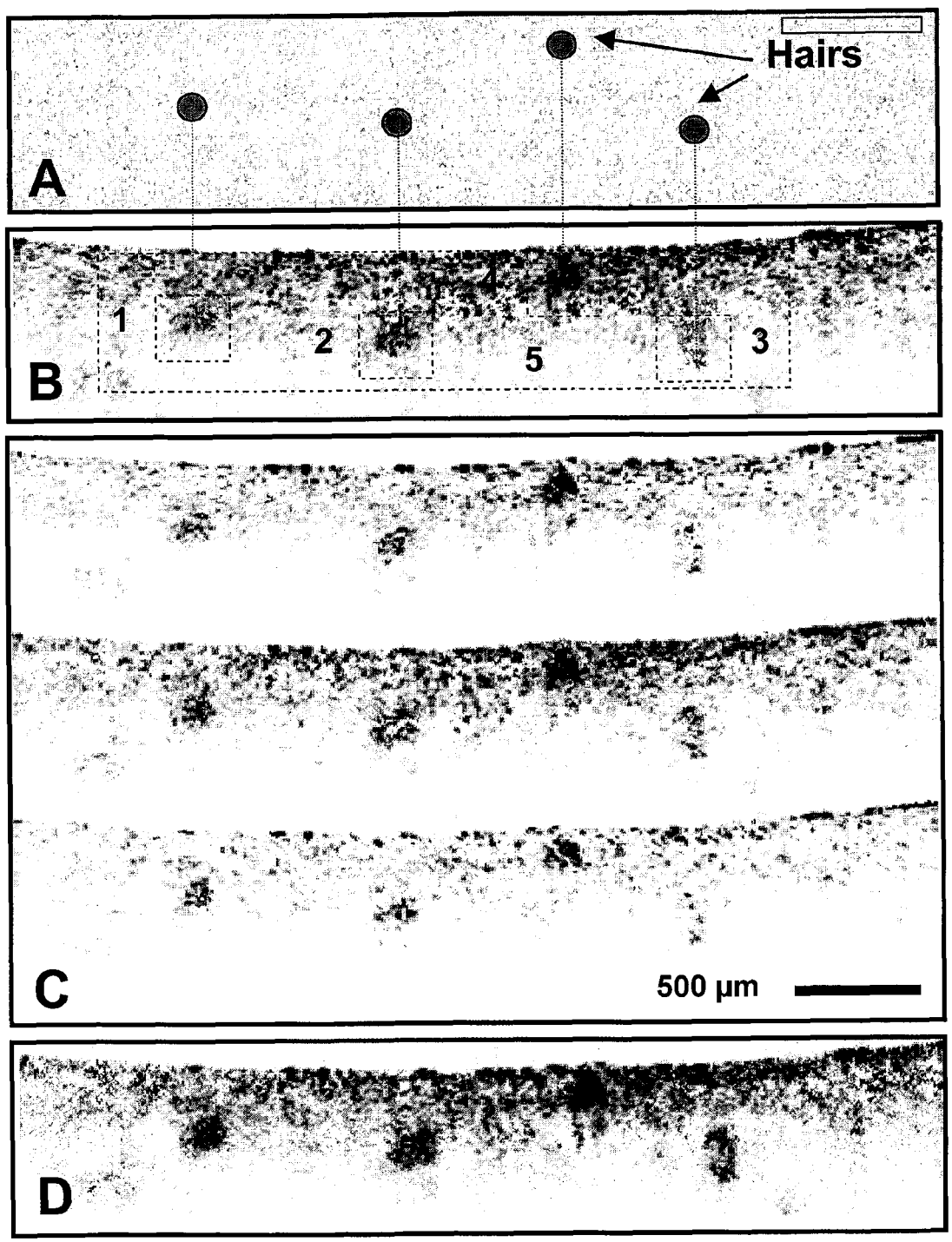
FIG. 2A is a schematic diagram of an exemplary embodiment of an Intralipid-Agar phantom according to the present invention.
FIG. 2B is an exemplary OCT image of the phantom of FIG. 2A without the insertion of a BK7 ACPE element.
FIG. 2C is an illustration of exemplary ACPE OCT images obtained by splitting a sample beam in two parts using an exemplary 3.1 mm BK7 glass element.
FIG. 2D is an illustration of an exemplary compound image in which speckle is reduced.

A solid phantom consisting of 1% Intralipid solution and Agar can be used to measure a reduction in speckle provided by ACPE. For example, four (4) hairs can be embedded in the Intralipid-Agar gel at different transverse positions and depths. A schematic of the phantom is depicted in FIG. 2A. The corresponding OCT images with and without the BK7 glass plate are shown in FIGS. 2B and 2C, respectively. ROI's labeled 1-5 represent exemplary locations where the SNR improvement by ACPE is preferably measured. The insertion of the BK7 glass plate 20 (with a 3.1 mm BK7 glass element) in the sample arm can produce three copies of the original OCT image (see FIG. 2C), with each image being acquired at a different illumination angles and separated by group delay increments of, e.g., 800 μ,m. The amplitudes of the signals in the top and bottom images of FIG. 2C can be approximately half of the center image ($S1_{OCT}/S2_{OCT}=S3_{OCT}=S3_{OCT}/S2_{OCT}=1:2$). The compounded ACPE image shown in FIG.

2D can bes obtained by incoherently averaging the three images that are shown in FIG. 2C, A substantial reduction of speckle in the compounded image can be visualized in FIG. 2D. Compared to the original OCT image, the average ACPE SNR improvement for the five regions depicted in FIG. 2B is preferably 1.54±0.12 (mean±standard deviation).

IV. Example 3

Figure 3:
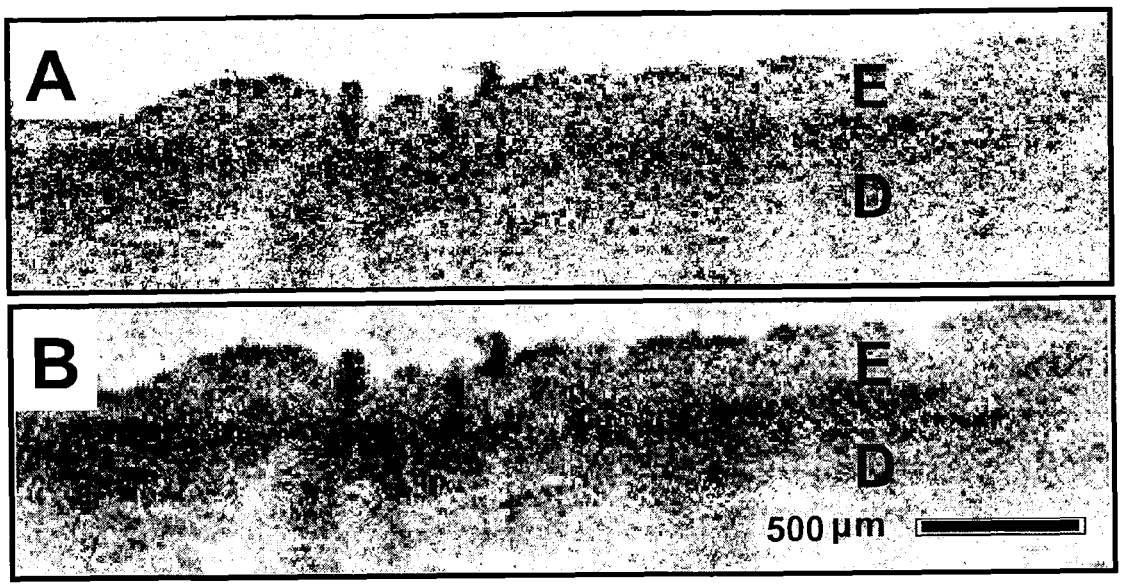
FIG. 3A is an exemplary OCT image of a ventral forearm obtained in vivo prior to the insertion of the BK7 ACPE element.
FIG. 3B is an exemplary compounded ACPE OCT image of the skin acquired at the same location as that in FIG. 3A.

In order to demonstrate SNR improvement in vivo, ACPE OCT imaging can be performed on a ventral forearm of a subject. FIGS. 3A and 3B shows one representative set of images. FIG. 3A shows an exemplary OCT image of the ventral forearm obtained in vivo prior to the insertion of the BK7 ACPE element. Visual assessment of these pictures demonstrates a qualitative improvement in the compounded ACPE image (FIG. 3B). The boundary between the epidermis (E) and dermis (D) is more clearly demarcated with ACPE as shown in FIG. 3B. In addition, horizontal structures consistent with dermal vasculature are more readily identified in the ACPE image of FIG. 3B. The SNR can be measured for the ACPE and original OCT images in FIG. 3B, providing an exemplary SNR improvement of 1.56.

The apparatus and method according to the exemplary embodiments of the present invention are provide to reduce speckle in OCT images that does not decrease the OCT frame rate and requires only minor modifications to the OCT probe. The implementation of ACPE, implements potential compromises between speckle reduction and three other OCT system parameters: a) sample arm transverse resolution, b) total reference arm path length, and c) OCT image sensitivity. In particular, for any given objective lens, ACPE may compromise the transverse resolution in one dimension by underfilling the lens aperture for each individual beamlet. In most cases, increasing the numerical aperture (NA) of the objective can compensate for this resolution loss.

Speckle averaged ACPE-OCT images can be obtained at the same rate as conventional OCT images by scanning an increased reference arm path length delay at substantially the same frequency. In order to acquire each of the individual OCT subimages, the new scan length of the ACPE-OCT system can preferably be L(2m−1), where L is the original scan length of the OCT system. Using phase control RSOD lines, scan ranges up to 10 mm are possible, thus enabling m=3, L=2 mm, and a maximum predicted SNR improvement of ~2.1.

Increasing the reference arm path length scan range while maintaining the scan rate, may increase the electronic bandwidth and decrease the sensitivity of the OCT system. Also, because ACPE splits the sample arm power into 2m−1 subimages, each subimage contains a fraction of the original sample arm power. When imaging a human tissue, these losses may primarily affect the penetration depth of the OCT image. Since many features of clinical relevance, such as nuclei in patients with Barrett's esophagus or macrophages in atherosclerotic plaques, may bee present at tissue surfaces, for modest m, the improvements in image quality provided by ACPE likely outweigh sensitivity losses. Moreover, ongoing technical developments towards more efficient interferometer designs and higher power, clinically viable OCT sources may render ACPE sensitivity losses a non-issue.

The thickness of the path length encoding optical element described herein in the above-referenced Examples (3.1 mm BK7) may not be sufficient for OCT imaging in some tissues since the provide 800 µm separation between individual subimages. Increasing the thickness of the BK7 glass to 7.7 mm may allow a path length separation of 2 mm. This thickness may be adequate for a free-space, hand-held OCT probes, but can be problematic in small diameter, flexible catheters, where minimizing the rigid length can be important. In order to increase the optical thickness of the path length encoding element, a higher refractive index material such as silicon (n=3.5) may be used. To create a 2 mm delay with silicon, preferably approximately 1.6 mm of the material can be used. When using high refractive index glass, dispersion imbalances between the reference and sample arms should be considered. For high-resolution OCT imaging ($\Delta\lambda\lambda > 10\%$), appropriate selection of the optical material used for path length encoding will depend on the center wavelength and bandwidth of the source.

Advantages of the exemplary embodiment of the method and apparatus according to the present invention may include the fact that the OCT frame rate is not increased, and the addition of only a single passive element in the OCT probe should be implemented. These features of ACPE make the system and method of the present invention compatible with OCT imaging in internal organ systems in patients. While implementation of ACPE may facilitate tradeoffs between speckle reduction and system sensitivity, the problems caused by speckle noise are likely more significant for clinical diagnosis than the penetration depth of modern OCT systems, especially at 1300 nm. Since difficulties in interpreting features on the size scale of 20 um or less is in part a result of speckle noise in OCT images, ACPE would likely significantly improve the capabilities of OCT for the diagnosis of important diseases such as, but not limited to, dysplasia and inflammation in atherosclerosis.

Although only particular exemplary embodiments of the present invention have been described in detail herein above, those skilled in the art will readily appreciate and understand that many modifications are possible in the exemplary embodiments without materially departing from the novel teachings and advantages of this invention. Accordingly, all such modifications are intended to be included within the scope of the present invention as defined in the following claims.

The invention claimed is:

1. An apparatus for irradiating a structure, comprising:
a sample arm configuration configured to receive an electromagnetic radiation and including an arrangement, the arrangement being configured to produce at least two radiations from the electromagnetic radiation so as to irradiate the structure and delay a first radiation of the radiations with respect to a second radiation of the radiations, wherein the arrangement including at least one of:
a first optical section with a refractive index of at least 1.5, the first section being structured to propagate the radiations, and
a second section which has silicon, the second section being structured to propagate the radiations.

2. The apparatus according to claim 1, wherein the refractive index of the optical section is at least 3.0.

3. The apparatus according to claim 1, wherein at least one of the first section or the second section comprises an anti-reflection-coated BK 7 glass.

4. The apparatus according to claim 3, wherein the glass has a thickness of from about 1.6 mm to about 7.7 mm.

5. The apparatus according to claim 1, wherein at least one of the first section or the second section comprises an anti-reflection-coated glass that has a refractive index of from about 1.51 to about 3.5.

6. An apparatus for obtaining information associated with a structure, comprising;

a first arrangement configured to received first and second radiations from the structure associated with particular radiations forwarded to the structure which have different path lengths and a third radiation received from a reference, and generate at least one interference signal as a function of the first, second and third radiations;

a second arrangement configured to generate:
first data associated with the first radiation which includes a first speckle pattern and second data associated with the second radiation which includes a second speckle pattern, and
third data associated with the structure based on the first and second data that has a speckle pattern the amount of which is smaller that the amount of at least one of the first speckle pattern or the second speckle pattern.

7. The apparatus according to claim 6, further comprising a further arrangement configured to forward the particular radiations to the structure, wherein the further arrangement includes an optical section with a refractive index of at least 1.5, the optical section being structured to propagate the first and second radiations.

8. The apparatus according to claim 6, further comprising a further arrangement configured to forward the particular radiations to the structure, wherein the further arrangement includes a section which has silicon that is structured to propagate the first and second radiations.

9. The apparatus according to claim 6, further comprising a further arrangement configured to forward the particular radiations to the structure, wherein the further arrangement includes a section which has an anti-reflective coating on at least one surface thereof, the section being structured to propagate the first and second radiations.

10. The apparatus according to claim 6, wherein the second arrangement is further configured to generate third data corresponding to an amount of a ranging depth within the structure associated with the first arrangement, wherein a difference between the path lengths of the first and second radiations is equal or greater than the ranging depth, and wherein the ranging depth is a penetration depth in the structure which includes an anatomical structure.

11. The apparatus according to claim 6, wherein the first, second and the third data are images, the third image data having a noise that is smaller than a noise of the first image data and a noise of the second image data.

12. The apparatus according to claim 6, wherein the first, second and the third data are images, and wherein the third arrangement is configured to generate the third image data based on a mathematical combination of the first and second image data.

13. The apparatus according to claim 6, further comprising an additional arrangement which is configured to irradiate the structure by a first irradiation of the particular radiations at a first angle, and by a second radiation of the particular radiations at a second angle, the first and second angles being different from one another.

14. The apparatus according to claim 13, wherein the first and second angle are different from one another as a function of a delay between the first and second radiations and at least one of a phase or a incident angle of each of the first and second radiations.

15. The apparatus according to claim 6, further comprising a detection arrangement which is configured to detect the first radiation, and forwards the detected energy to the second arrangement.

16. The apparatus according to claim 6, further comprising a third arrangement which includes two sections, each section being configured to delay a respective one of the first and second radiations, and wherein a delay of the first radiation is greater than a delay of the second radiation.

17. The apparatus according to claim 6, further comprising a further arrangement configured to receive a plurality of radiation and irradiate the structure and delay at least one radiation of the radiations with respect to at least another one radiation of the radiations, wherein the arrangement including at least one of:
a first optical section with a refractive index of at least 1.5, the first section being structured to propagate the radiations, and
a second section which has silicon, the second section being structured to propagate the radiations.

18. The apparatus according to claim 17, wherein the refractive index of the optical section is at least 3.0.

19. The apparatus according to claim 17, wherein at least one of the first section or the second section comprises an anti-reflection-coated BK 7 glass.

20. The apparatus according to claim 19, wherein the glass has a thickness of from about 1.6 mm to about 7.7 mm.

21. The apparatus according to claim 17, wherein at least one of the first section or the second section comprises an anti-reflection-coated glass that has a refractive index of from about 1.51 to about 3.5.

22. An apparatus for obtaining information associated with a structure, comprising;
a first arrangement configured to separate at least one first electro-magnetic radiation into a first radiation and a second radiation forwarded to the structure, wherein the first and second radiations have different path lengths;
a second arrangement configured to received third and fourth radiations from the structure associated with the first and second radiations and a fifth radiation received from a reference; and
a third arrangement configured to generate data corresponding to an amount of a ranging depth within the structure associated with the second arrangement, wherein a difference between the path lengths of the first and second radiations is equal or greater than the ranging depth.

* * * * *